US011993670B2

(12) United States Patent
Cheng et al.

(10) Patent No.: US 11,993,670 B2
(45) Date of Patent: May 28, 2024

(54) ZWITTERIONIC BIOCOMPATIBLE POLYMERS, METHODS, AND USES THEREOF

(71) Applicant: THE BOARD OF TRUSTEES OF THE UNIVERSITY OF ILLINOIS, Urbana, IL (US)

(72) Inventors: Gang Cheng, Chicago, IL (US); Huifeng Wang, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 712 days.

(21) Appl. No.: 15/734,686

(22) PCT Filed: Jun. 6, 2019

(86) PCT No.: PCT/US2019/035809
§ 371 (c)(1),
(2) Date: Dec. 3, 2020

(87) PCT Pub. No.: WO2019/236858
PCT Pub. Date: Dec. 12, 2019

(65) Prior Publication Data
US 2021/0228737 A1 Jul. 29, 2021

Related U.S. Application Data

(60) Provisional application No. 62/681,124, filed on Jun. 6, 2018.

(51) Int. Cl.
C08F 220/36 (2006.01)
A61K 47/69 (2017.01)
C08G 73/02 (2006.01)

(52) U.S. Cl.
CPC ........ *C08F 220/36* (2013.01); *A61K 47/6939* (2017.08); *C08G 73/0226* (2013.01)

(58) Field of Classification Search
USPC .......................................................... 528/422
See application file for complete search history.

(56) References Cited

U.S. PATENT DOCUMENTS

| 8,404,224 | B2 | 3/2013 | Jiang et al. |
| 9,180,202 | B2 | 11/2015 | Hoogenboom |
| 9,533,006 | B2 * | 1/2017 | Jiang ................... C09D 151/085 |
| 9,695,275 | B2 | 7/2017 | Cheng |
| 10,010,627 | B2 | 7/2018 | Boday et al. |
| 10,058,620 | B2 | 8/2018 | Cheng et al. |
| 2009/0105375 | A1 | 4/2009 | Lynn et al. |
| 2013/0030119 | A1 | 1/2013 | Wang et al. |
| 2017/0174907 | A1 * | 6/2017 | Jiang ..................... C09D 183/04 |

FOREIGN PATENT DOCUMENTS

| WO | WO-99/22744 A1 | 5/1999 |
| WO | WO-2016/007424 A2 | 1/2016 |

OTHER PUBLICATIONS

Aumelas et al., Nanoparticles of hydrophobically modified dextrans as potential drug carrier systems. Colloid Surface B 2007, 59 (1), 74-80.
Allen, Ligand-targeted therapeutics in anticancer therapy, Nat. Rev. Cancer, 2(10):750-63 (2002).
Bontempo et al., Cysteine-reactive polymers synthesized by atom transfer radical polymerization for conjugation to proteins. J Am Chem Soc 2004, 126 (47), 15372-15373.
Borgman et al., Tumor-targeted HPMA copolymer-(RGDfK)-(CHX-A "-DTPA) conjugates show increased kidney accumulation. J Control Release 2008, 132 (3), 193-199.
Brissault et al., Synthesis of linear polyethylenimine derivatives for DNA transfection. Bioconjug Chem 2003, 14 (3), 581-7.
Burke et al., Liposomal Stabilization of Camptothecins Lactone Ring. J Am Chem Soc 1992, 114 (21), 8318-8319.
Cao et al., Nanoparticles for Drug Delivery Prepared from Amphiphilic PLGA Zwitterionic Block Copolymers with Sharp Contrast in Polarity between Two Blocks. Angew Chem Int Edit 2010, 49 (22), 3771-3776.
Chen et al., Functionalized single-walled carbon nanotubes as rationally designed vehicles for tumor-targeted drug delivery. J Am Chem Soc 2008, 130 (49), 16778-85.
Cheng et al., Functionalizable and Ultrastable Zwitterionic Nanogels. Langmuir 2010, 26 (10), 6883-6886.
Duke, Synthesis and Development of zwitterionic PEI (zPEI) for optimized delivery of nucleic acids, A thesis submitted in partial fulfillment of the requirements for the degree of Master of Science in the College of Arts and Sciences at hte University of Kentucky (2017).
Duncan, Polymer conjugates as anticancer nanomedicines. Nat Rev Cancer 2006, 6 (9), 688-701.
Ferguson et al., Studies on the mechanism of action of dextrin-phospholipase A2 and its suitability for use in combination therapy. Mol Pharm 2010, 7 (2), 510-21.
Fosgerau et al., Peptide therapeutics: current status and future directions, Drug Discov. Today, 20(1):122-8 (2015).
Gaberc-Porekar et al., Obstacles and pitfalls in the PEGylation of therapeutic proteins. Curr Opin Drug Disc 2008, 11 (2), 242-250.
Ganson et al., Pre-existing anti-polyethylene glycol antibody linked to first-exposure allergic reactions to pegnivacogin, a PEGylated RNA aptamer. J Allergy Clin Immunol 2016, 137 (5), 1610-1613 e7.
Goldberg, Nanostructured materials for applications in drug delivery and tissue engineering. J Biomat Sci-Polym E 2007, 18 (3), 241-268.
Harris et al., Effect of pegylation on pharmaceuticals. Nature Reviews Drug Discovery 2003, 2 (3), 214-221.

(Continued)

Primary Examiner — Terressa Boykin
(74) Attorney, Agent, or Firm — MARSHALL, GERSTEIN & BORUN LLP

(57) ABSTRACT

Provided herein are biocompatible polymers having a polymer backbone and one or more repeating units, and methods of making and using the same. The repeating units can each be individually selected from a zwitterionic precursor repeating unit of Formula (1). Also provided are systems for nucleic acid delivery including the biocompatible polymers, the systems having a cationic core and a polysaccharide-anionic peptide conjugate adsorbed to the cationic core.

20 Claims, 6 Drawing Sheets

(56) References Cited

OTHER PUBLICATIONS

He et al., Molecular simulation studies of protein interactions with zwitterionic phosphorylcholine self-assembled monolayers in the presence of water. Langmuir 2008, 24 (18), 10358-10364.
He et al., Origin of repulsive force and structure/dynamics of interfacial water in OEG-protein interactions: a molecular simulation study. Physical Chemistry Chemical Physics 2008, 10 (36), 5539-5544.
Hoogenboom, Poly(2-oxazoline)s: A Polymer Class with Numerous Potential Applications. Angew Chem Int Edit 2009, 48 (43), 7978-7994.
Huo et al., A new class of silica cross-linked micellar core-shell nanoparticles. J Am Chem Soc 2006, 128 (19), 6447-6453.
Kataoka et al., Block copolymer micelles for drug delivery: design, characterization and biological significance. Adv Drug Deliver Rev 2001, 47 (1), 113-131.
Keefe et al., Poly(zwitterionic)protein conjugates offer increased stability without sacrificing binding affinity or bioactivity. Nat Chem 2012, 4 (1), 60-64.
Langer, Drug delivery: Drugs on target. Science 2001, 293 (5527), 58-59.
Lee et al., A single dose of doxorubicin-functionalized bow-tie dendrimer cures mice bearing C-26 colon carcinomas. P Natl Acad Sci USA 2006, 103 (45), 16649-16654.
Lee et al., Polymer-caged lipsomes: a pH-responsive delivery system with high stability. J Am Chem Soc 2007, 129 (49), 15096-7.
McSweeney et al., Physician Awareness of Immune Responses to Polyethylene Glycol-Drug Conjugates. Clin Transl Sci 2018, 11 (2), 162-165.
Qi et al., Protein-polymer conjugation-moving beyond PEGylation, Curr. Opin. Chem. Biol., 28:181-93 (2015).
Raemdonck et al., Advanced nanogel engineering for drug delivery. Soft Matter 2009, 5 (4), 707-715.
Sapra et al., Ligand-targeted liposomes for cancer treatment. Curr Drug Deliv 2005, 2 (4), 369-81.
Satchi-Fainaro et al., Polymer therapeutics for cancer: Current status and future challenges. Polymer Therapeutics Ii: Polymers as Drugs, Conjugates and Gene Delivery Systems 2006, 193, 1-65.
Soppimath et al., Multifunctional core/shell nanoparticles self-assembled from pH-induced thermosensitive polymers for targeted intracellular anticancer drug delivery. Adv Funct Mater 2007, 17 (3), 355-362.
Soussan et al., Drug Delivery by Soft Matter: Matrix and Vesicular Carriers. Angew Chem Int Edit 2009, 48 (2), 274-288.
Tong et al., Anticancer polymeric nanomedicines. Polymer Reviews 2007, 47 (3), 345-381.
Veronese, Peptide and protein PEGylation: a review of problems and solutions. Biomaterials 2001, 22 (5), 405-417.
Wileman, Properties of Asparaginase-Dextran Conjugates. Adv Drug Deliver Rev 1991, 6 (2), 167-180.
Yang et al., Anti-PEG immunity: emergence, characteristics, and unaddressed questions. Wires Nanomed Nanobi 2015, 7 (5), 655-677.
Yang et al., Functionalizable and ultra stable nanoparticles coated with zwitterionic poly(carboxybetaine) in undiluted blood serum. Biomaterials 2009, 30 (29), 5617-5621.
International Application No. PCT/US2019/035809, International Search Report and Written Opinion, dated Oct. 22, 2019.

* cited by examiner (a) PEI/pDNA (b) Dex20k-LipE5H/PEI/pDNA (c) CDex20k-LipE5H/PEI/pDNA (d) CDex20k-LipE5H/PEI/pDNA with excess DTT

ZWITTERIONIC BIOCOMPATIBLE POLYMERS, METHODS, AND USES THEREOF

CROSS-REFERENCE TO RELATED APPLICATION

This is the U.S. national phase of International Application No. PCT/US2019/035809, filed Jun. 6, 2019, which claims the benefit of priority to U.S. Provisional Patent Application 62/681,124, filed Jun. 6, 2018, and the entire respective disclosure of which are each is incorporated herein by reference.

BACKGROUND

Field of the Disclosure

The disclosure relates to biocompatible polymers that include zwitterionic repeating units or zwitterionic precursor repeating units that convert to zwitterionic moieties upon exposure to certain environmental stimuli.

BRIEF DESCRIPTION OF RELATED TECHNOLOGY

Nanomedicine utilizing nucleic acids, proteins, and small molecule drugs holds great promise as therapeutic agents. Protein and peptide drugs, however, can be degraded by proteolytic enzymes, can be rapidly cleared by the kidneys, generate neutralizing antibodies, and have a short circulating half-life.

Further, the use of gene therapy as a strategy for the treatment of genetic disorders or acquired diseases that are currently considered "incurable" has drawn significant interest. The success of gene therapy relies on safe and efficient gene delivery systems. These systems must provide DNA protection, cellular uptake, endosomal escape, and low toxicity to overcome obstacles in gene therapy. So far, various delivery systems have been developed, and they can be grouped into two general categories: viral and non-viral vectors. Non-viral vectors are not as efficient as viral vectors, but provide safer delivery strategies since they could avoid the problems associated with viruses, including complexity of production, immunogenicity and mutagenesis. Currently, the majority of non-viral vectors are made of synthetic materials such as cationic lipids, polymers, and dendrimers. However, many of these have high toxicity, low transfection efficiency, low biodegradability, and poor compatibility in vivo.

Natural materials, such as cationic polysaccharides and peptides, have been studied as potential gene delivery carriers to avoid the chronic toxicity associated with carriers based on synthetic materials. Chitosan has been studied as a gene delivery carrier due to its biocompatibility, but its transfection efficiency and solubility are unsatisfactory. Peptide vectors, composed of natural amino acids, are compatible with biological environments, are less cytotoxic and biodegradable. However, major obstacles for the further development of natural polymer-based gene carriers include low gene transfection efficiency, poor loading efficiency, and poor blood circulation.

Currently, PEGylation, the process by which polyethylene glycol (PEG) chains are attached to protein and peptide drugs, can overcome these and other shortcomings. By increasing the molecular mass of proteins and peptides and shielding them from proteolytic enzymes, PEGylation improves pharmacokinetics. However, several recent studies reported the anti-PEG antibody led the fast clearance of PEG prodrug. For example, a Phase II clinical trial discovered the preexisting anti-PEG antibody and lead to the failure of the trial. PEG was found to reduce the activity of the conjugated protein/peptide, due to its amphiphilic characteristics.

SUMMARY

In embodiments, a biocompatible polymer can include a polymer backbone including one or more repeating units, wherein the one or more repeating units are each individually selected from a zwitterionic precursor repeating unit of Formula (I):

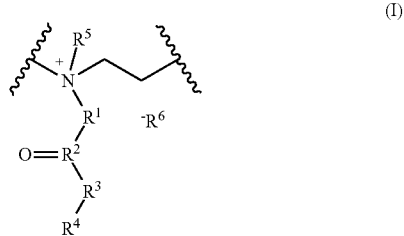

(I)

wherein $R^1$ is $-(CH_2)_n-$, $-(CH_2)_nO(CH_2)_m-$, $-(CH_2CH_2OCH_2CH_2)_n-$, $-(CH_2CH_2O)_nCH_2CH_2-$, $-(CH_2CH_2O)_n(CH_2)_m-$, $-(CH_2)_n(CH_2CH_2O)_m(CH_2)_p-$, $-((CH_2)_{1-8}C(O)O)_n(CH_2)_m-$, $-((CH_2)_{1-8}C(O)O)_n(CH_2CH_2)_m(OC(O)(CH_2)_{1-8})_p-$, $-((CH_2)_{1-8}C(O)O)_n(CH_2CH_2)_m(OC(O)(CH_2)_{1-8})_p-$, $-(CH_2C(O)O)_n(CH_2CH_2)_m(OC(O)CH_2)_p-$, $-(CH(CH_3)C(O)O)_n(CH_2CH_2)_m(OC(O)CH(CH_3))_p-$, $-(CH(CH_3)C(O)O)_n(CH_2CH_2)_m(OC(O)CH(CH_3))_p-$, $-((CH_2)_nOC(O)O)(CH_2CH_2)_m-$, $-(CH_2)_nNHC(O)(CH_2)_m-$, $-(CH_2)_nC(O)NH(CH_2)_m-$, $-(CH_2)_nS(O_2)(CH_2)_m-$, $-(CH_2)_nS(O_2)(CH_2)_mO(CH_2)_t-$, $-(CH_2)_nO-$, $-(CH_2)_nO(CH_2)_mO-$, $-(CH_2CH_2OCH_2CH_2)_nO-$, $-(CH_2CH_2O)_nCH_2CH_2O-$, $-(CH_2CH_2O)_n(CH_2)_mO-$, $-(CH_2)_n(CH_2CH_2O)_m(CH_2)_pO-$, $-((CH_2)_{1-8}C(O)O)_n(CH_2)_mO-$, $-((CH_2)_{1-8}C(O)O)_n(CH_2CH_2)_m(OC(O)(CH_2)_{1-8})_pO-$, $-((CH_2)_{1-8}C(O)O)_n(CH_2CH_2)_m(OC(O)(CH_2)_{1-8})_pO-$, $-(CH_2C(O)O)_n(CH_2CH_2)_m(OC(O)CH_2)_pO-$, $-(CH(CH_3)C(O)O)_n(CH_2CH_2)_m(OC(O)CH(CH_3))_pO-$, $-(CH(CH_3)C(O)O)_n(CH_2CH_2)_m(OC(O)CH(CH_3))_pO-$, $-((CH_2)_nOC(O)O)(CH_2CH_2)_m-$, $-(CH_2)_nNHC(O)(CH_2)_mO-$, $-(CH_2)_nC(O)NH(CH_2)_mO-$, $-(CH_2)_nS(O_2)(CH_2)_mO-$, or $-(CH_2)_nS(O_2)(CH_2)_mO(CH_2)_tO-$; $R^2$ is C, P(OR$^7$), or S(=O); $R^3$ is O, NH, or OC(=O); $R^4$, $R^5$ and $R^7$ are each independently H, $-CH_3$, $-(CH_2)_nCH_3$, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, $-(CH_2)_nC(O)NH(CH_2)_mOH$, $C_{1-n}$ alkenyl, $C_{1-n}$ alkynyl, $C_{6-10}$ aryl, pentafluorophenyl, or succinimidyl; $R^6$ is F, Cl, Br, I, acetate, citrate, bicarbonate, carbonate, chlorate, dihydrogen phosphate, hydrogen phosphate, hydrogen sulfate, hydroxide, nitrate, nitride, nitrite, phosphate, sulfate, sulfide, sulfite, thiocyanate, thiosulfate, oxalate, perchlorate, chlorite, hypochlorite, periodate, iodate, hypoiodate, bromate, hypobromate, hypobromite, hydrogen carbonate, hydrogen sulfate, hydrogen sulfite, hydrogen oxalate, borate, tetraborate, hexfluorosilicate, tartrate, silicate, selenite, arsenate, ethanedioate, oxoethanoate, 2-hydroxyethanoate, propanoate, butanoate, pentanoate, butyrate, formate, lactate, maleate, oleate, oxalate, stearate, tarterate, urate, acrylate, glutamate, malonate, phthalate, barbiturate, cinnamate, hexanoate, folate, propionate, stearate, ascorbate, glutarate, azelate, benzilate, fumarate, gluconate, propiolate, tannate, gallate, titanate, trifluoroacetate, or diuranate; each n, m, p, q, and r is independently 1 to 10,000; and, t is 0 to 10,000.

In embodiments, a nanoparticle can include a biocompatible polymer, as disclosed herein, and a drug, wherein the drug can be a peptide, a protein, a nucleic acid, a small molecule drug, a prodrug, and any combination thereof.

In accordance with embodiments a method can include (i) reacting a polyethyleneimine having a structure of:

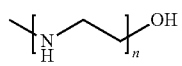

with an α,β-unsaturated ester having a structure of

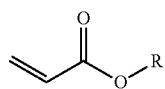

to form an N-alkylated polyethyleneimine having a structure of

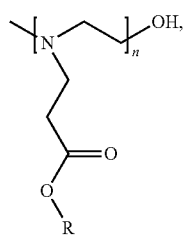

wherein n is from 1 to 10,000 and R is H, —$CH_3$, —$(CH_2)_n$$CH_3$, —$(CH_2CH_2O)_n CH_3$, —$(CH_2CH_2O)_n(CH_2)_m CH_3$, —$(CH_2CH_2O)_n(CH_2)_m OH$, —$((CH_2)_n O)_m((CH_2)_p O)_q (CH_2)_r OH$, —$(CH_2CH_2O)_n H$, —$(CH_2)_n OH$, —$(CH_2)_n O(CH_2)_m OH$, —$(CH_2CH_2OCH_2CH_2)_n OH$, —$(CH_2CH_2O)_n CH_2CH_2OH$, —$((CH_2)_{1-8}C(O)O)_n(CH_2)_m OH$, —$((CH_2)_{1-8}C(O)O)_n(CH_2CH_2O)_m(OC(O)(CH_2)_{1-8})_p OH$, —$((CH_2)_{1-8}C(O)O)_n(CH_2CH_2)_m(OC(O)(CH_2)_{1-8})_p OH$, —$(CH_2C(O)O)_n(CH_2CH_2)_m(OC(O)CH_2)_p OH$, —$(CH(CH_3)C(O)O)_n(CH_2CH_2)_m(OC(O)CH(CH_3))_p OH$, —$((CH_2)_n OC(O)O)(CH_2CH_2)_m OH$, —$(CH_2)_n NHC(O)(CH_2)_m OH$, —$(CH_2)_n C(O)NH(CH_2)_m OH$, $C_{1-n}$ alkenyl, $C_{1-n}$ alkynyl, $C_{6-10}$ aryl, pentafluorophenyl ester or succinimidyl; (ii) hydrolyzing the N-alkylated polyethyleneimine to provide a zwitterionic N-alkylated polyethyleneimine; (iii) reacting the zwitterionic N-alkylated polyethyleneimine with a compound having a functional group capable of conjugating to a peptide, a protein, a monosaccharide, a disaccharide, an oligo/polysaccharide, a lipid, a nucleic acid, a polymer, a targeting ligand molecule, a prodrug, a small molecule drug, or any combination thereof to form a biocompatible zwitterionic polymer.

In embodiments, a polysaccharide-anionic peptide conjugate for nucleic acid delivery can include a polysaccharide polymer, and an anionic peptide bonded to the polysaccharide polymer as a side chain.

In accordance with embodiments, a system for nucleic acid delivery can include a cationic core including a cationic compound and nucleic acid, and the polysaccharide-anionic peptide conjugate of described herein adsorbed the cationic core.

In embodiments, a system for nucleic acid delivery can include a cationic core including a cationic compound and nucleic acid; and, a polysaccharide-anionic peptide conjugate comprising an anionic peptide physically bound to a polysaccharide, wherein the polysaccharide-anionic peptide is adsorbed to the cationic core, and the biocompatible polymer as described herein can be associated with the cationic core or the polysaccharide-anionic peptide conjugate.

Further aspects and advantages of the disclosure will be apparent to those of ordinary skill in the art from a review of the following detailed description. While the compositions, systems, and methods are susceptible to embodiments in various forms, the description hereafter includes specific embodiments, with the understanding that the disclosure is illustrative, and is not intended to limit the scope of the disclosure to the specific embodiments described herein.

DETAILED DESCRIPTION

Biocompatible Polymer

Figure 1:
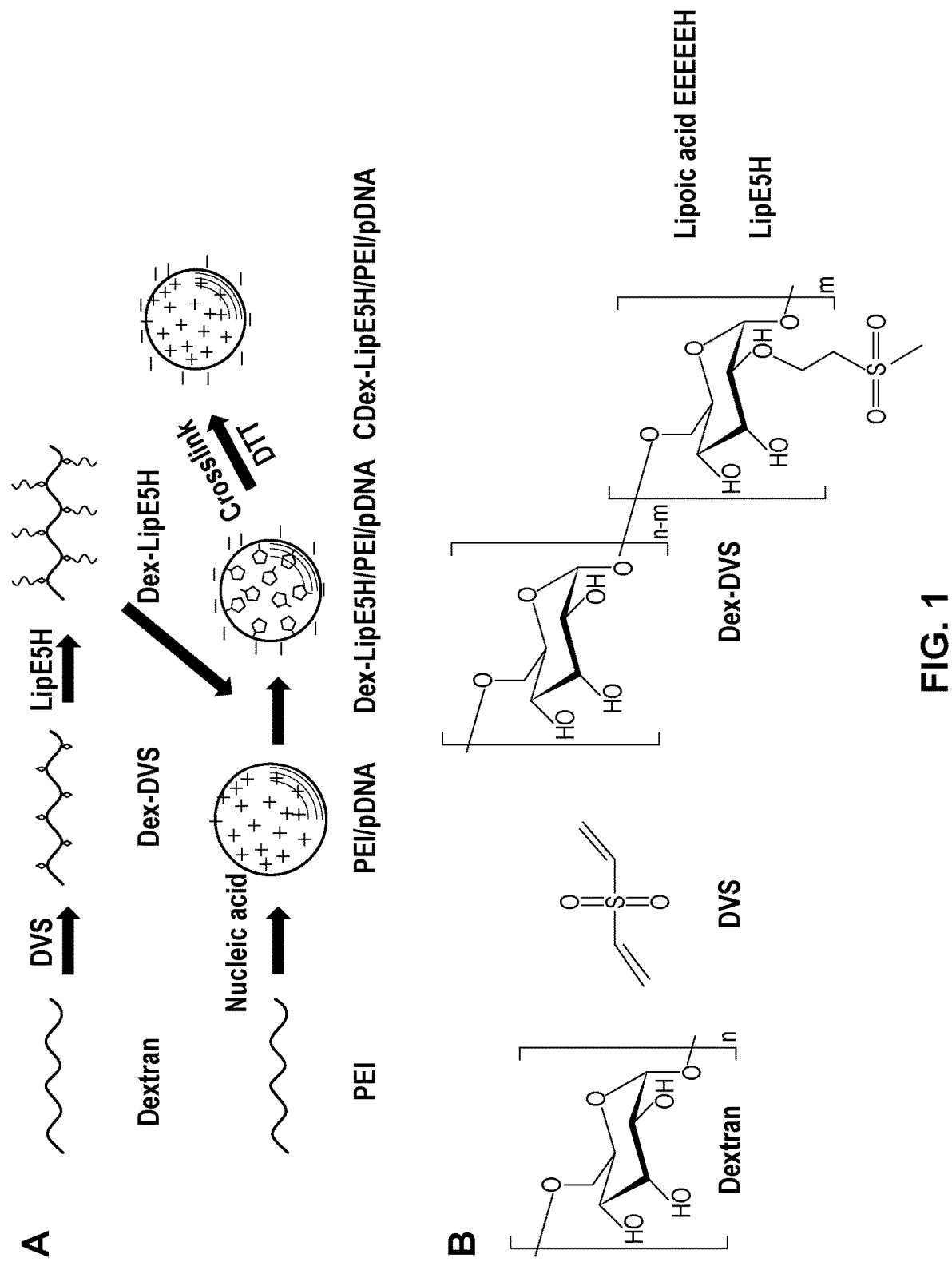
FIG. 1A is a scheme illustrating the preparation process of a system for nucleic acid delivery according to the disclosure.
FIG. 1B is a scheme showing the structures of each of the shorthand references in FIG. 1A.

In accordance with embodiments, a biocompatible polymer is provided with a polymer backbone including one or more repeating units, with at least one of the repeating units being a zwitterionic precursor unit or a zwitterionic unit.

Advantageously, the biocompatible polymers of the disclosure can be used for protein conjugation, drug delivery, and/or gene delivery. Embodiments of the polymers of the disclosure can have improved solubility and biocompatibility which, when conjugated to the polymers, can significantly increase the stability and/or half-life of a protein, a peptide, a drug, or genetic material in the blood, and can reduce its renal clearance and immune response. Furthermore, the biocompatible polymers of the disclosure do not substantially compromise the activity of the protein, peptide, drug, or genetic material. Still further, the biocompatible polymers can have superior antifouling properties to resist protein adsorption.

In embodiments, the biocompatible polymer includes a polymer backbone including one or more repeating units, wherein the one or more repeating units are each individually selected from a zwitterionic precursor repeating unit. Zwitterionic precursor repeating units are capable of being converted to zwitterionic repeating units—repeating units having at least one positively charged functional group and at least one negatively charged functional group, such that the repeating unit has a net charge of zero at a specific pH or has a balanced charge.

The zwitterionic precursor repeating unit can be converted to a zwitterionic repeating unit through the use of hydrolysis, chemical agents, heat, radiation, electricity, oxidation, reduction, acid, and/or base. In embodiments, the zwitterionic precursor repeating unit is hydrolyzed to provide a zwitterionic repeating unit.

In embodiments, the zwitterionic precursor repeating unit has a structure of Formula (I):

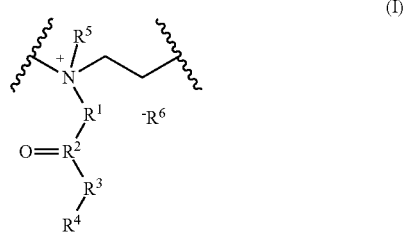

(I)

wherein the substituents are described in detail, below.

$R^1$ can be $-(CH_2)_n-$, $-(CH_2)_nO(CH_2)_m-$, $-(CH_2CH_2OCH_2CH_2)_n-$, $-(CH_2CH_2O)_nCH_2CH_2-$, $-(CH_2CH_2O)_n(CH_2)_m-$, $-(CH_2)_n(CH_2CH_2O)_m(CH_2)_p-$, $-((CH_2)_{1-8}C(O)O)_n(CH_2)_m-$, $-((CH_2)_{1-8}C(O)O)_n(CH_2CH_2)_m(OC(O)(CH_2)_{1-8})_p-$, $-((CH_2)_{1-8}C(O)O)_n(CH_2CH_2)_m(OC(O)(CH_2)_{1-8})_p-$, $-(CH_2C(O)O)_n(CH_2CH_2)_m(OC(O)CH_2)_p-$, $-(CH(CH_3)C(O)O)_n(CH_2CH_2)_m(OC(O)CH(CH_3))_p-$, $-(CH(CH_3)C(O)O)_n(CH_2CH_2)_m(OC(O)CH(CH_3))_p-$, $-((CH_2)_nOC(O)O)(CH_2CH_2)_m-$, $-(CH_2)_nNHC(O)(CH_2)_m-$, $-(CH_2)_nC(O)NH(CH_2)_m-$, $-(CH_2)_nS(O_2)(CH_2)_m-$, $-(CH_2)_nS(O_2)(CH_2)_mO(CH_2)_t-$, $-(CH_2)_nO-$, $-(CH_2)_nO(CH_2)_mO-$, $-(CH_2CH_2OCH_2CH_2)_nO-$, $-(CH_2CH_2O)_nCH_2CH_2O-$, $-(CH_2CH_2O)_n(CH_2)_mO-$, $-(CH_2)_n(CH_2CH_2O)_m(CH_2)_pO-$, $-((CH_2)_{1-8}C(O)O)_n(CH_2)_mO-$, $-((CH_2)_{1-8}C(O)O)_n(CH_2CH_2)_m(OC(O)(CH_2)_{1-8})_pO-$, $-((CH_2)_{1-8}C(O)O)_n(CH_2CH_2)_m(OC(O)(CH_2)_{1-8})_pO-$, $-(CH_2C(O)O)_n(CH_2CH_2)_m(OC(O)CH_2)_pO-$, $-(CH(CH_3)C(O)O)_n(CH_2CH_2)_m(OC(O)CH(CH_3))_pO-$, $-(CH(CH_3)C(O)O)_n(CH_2CH_2)_m(OC(O)CH(CH_3))_pO-$, $-((CH_2)_nOC(O)O)(CH_2CH_2)_mO-$, $-(CH_2)_nNHC(O)(CH_2)_mO-$, $-(CH_2)_nC(O)NH(CH_2)_mO-$, $-(CH_2)_nS(O_2)(CH_2)_mO-$, or $-(CH_2)_nS(O_2)(CH_2)_mO(CH_2)_tO-$. In some embodiments, $R^1$ is $-(CH_2)_n-$, $-(CH_2)_nO(CH_2)_m-$, $-(CH_2CH_2OCH_2CH_2)_n-$, $-(CH_2CH_2O)_nCH_2CH_2-$, $-(CH_2CH_2O)_n(CH_2)_m-$, $-(CH_2)_n(CH_2CH_2O)_m(CH_2)_p-$, $-((CH_2)_{1-8}C(O)O)_n(CH_2)_m-$, $-((CH_2)_{1-8}C(O)O)_n(CH_2CH_2)_m(OC(O)(CH_2)_{1-8})_p-$, $-((CH_2)_{1-8}C(O)O)_n(CH_2CH_2)_m(OC(O)(CH_2)_{1-8})_p-$, $-(CH_2C(O)O)_n(CH_2CH_2)_m(OC(O)CH_2)_p-$, $-(CH(CH_3)C(O)O)_n(CH_2CH_2)_m(OC(O)CH(CH_3))_p-$, $-(CH(CH_3)C(O)O)_n(CH_2CH_2)_m(OC(O)CH(CH_3))_p-$, $-((CH_2)_nOC(O)O)(CH_2CH_2)_m-$, $-(CH_2)_nNHC(O)(CH_2)_m-$, $-(CH_2)_nC(O)NH(CH_2)_m-$, $-(CH_2)_nS(O_2)(CH_2)_m-$, or $-(CH_2)_nS(O_2)(CH_2)_mO(CH_2)_t-$.

$R^2$ can be C, P(OR$^7$), or S(=O). In some embodiments, $R^2$ is C. In some embodiments, $R^2$ is P(OR$^7$). In some embodiments, $R^2$ is S(=O).

$R^3$ can be O, NH, or O—C(=O)—. In some embodiments, $R^3$ is O. In some embodiments, $R^3$ is NH. In some embodiments, $R^3$ is O—C(=O)—.

$R^4$ can be H, $-CH_3$, $-(CH_2)_nCH_3$, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-(CH(CH_3)C(O)O)_n$ $-((CH_2)_nOC(O)O)(CH_2CH_2)_mOH$, $-(CH_2)_nNHC(O)(CH_2)_mOH$, $-(CH_2)_nC(O)NH(CH_2)_mOH$, $C_{1-n}$ alkenyl, $C_{1-n}$ alkynyl, $C_{6-10}$ aryl, pentafluorophenyl, or succinimidyl.

$R^5$ can be H, $-CH_3$, $-(CH_2)_nCH_3$, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-(CH(CH_3)C(O)O)_n$ $-((CH_2)_nOC(O)O)(CH_2CH_2)_mOH$, $-(CH_2)_nNHC(O)(CH_2)_mOH$, $-(CH_2)_nC(O)NH(CH_2)_mOH$, $C_{1-n}$ alkenyl, $C_{1-n}$ alkynyl, $C_{6-10}$ aryl, pentafluorophenyl, or succinimidyl.

$R^6$ can be F, Cl, Br, I, acetate, citrate, bicarbonate, carbonate, chlorate, dihydrogen phosphate, hydrogen phosphate, hydrogen sulfate, hydroxide, nitrate, nitride, nitrite, phosphate, sulfate, sulfide, sulfite, thiocyanate, thiosulfate, oxalate, perchlorate, chlorite, hypochlorite, periodate, iodate, hypoiodate, bromate, hypobromate, hypobromite, hydrogen carbonate, hydrogen sulfate, hydrogen sulfite, hydrogen oxalate, borate, tetraborate, hexfluorosilicate, tartrate, silicate, selenite, arsenate, ethanedioate, oxoethanoate, 2-hydroxyethanoate, propanoate, butanoate, pentanoate, butyrate, formate, lactate, maleate, oleate, oxalate, stearate, tarterate, urate, acrylate, glutamate, malonate, phthalate, barbiturate, cinnamate, hexanoate, folate, propionate, stearate, ascorbate, glutarate, azelate, benzilate, fumarate, gluconate, propiolate, tannate, gallate, titanate, trifluoroacetate or diuranate.

$R^7$ can be H, $-CH_3$, $-(CH_2)_nCH_3$, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n$ —(CH$_2$CH$_2$)$_m$(OC(O)(CH$_2$)$_{1-8}$)$_p$OH, —(CH$_2$C(O)O)$_n$
—(CH$_2$CH$_2$)$_m$(OC(O)CH$_2$)$_p$OH, —(CH(CH$_3$)C(O)O)$_n$
—(CH$_2$CH$_2$)$_m$(OC(O)CH(CH$_3$))$_p$OH, —((CH$_2$)$_n$OC(O)O)
—(CH$_2$CH$_2$)$_m$OH, —(CH$_2$)$_n$NHC(O)(CH$_2$)$_m$OH, —(CH$_2$)$_n$C(O)NH(CH$_2$)$_m$OH, C$_{1-n}$ alkenyl, C$_{1-n}$ alkynyl, C$_{6-10}$ aryl, pentafluorophenyl, or succinimidyl.

Each n, m, p, q, and r can be independently 1 to 10,000. For example, each of n, m, p, q, and r can be at least 1, 10, 100, 1000, 2000, 5000, or 7000, and/or up to 10,000, 7000, 5000, 2000, 1000, 100, or 10.

t can be 0 to 10,000. For example, t can be at least 0, 1, 10, 100, 1000, 2000, 5000, or 7000, and/or up to 10,000, 7000, 5000, 2000, 1000, 100, or 10.

The biocompatible polymer can include a zwitterionic unit in the polymer backbone as one or more of the repeating units. For example, in embodiments, the zwitterionic repeating unit can have a structure of Formula (II):

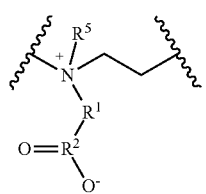

(II)

wherein the substituents are described in detail, above.

In embodiments, the polymer includes one or more zwitterionic repeating units having a structure selected from:

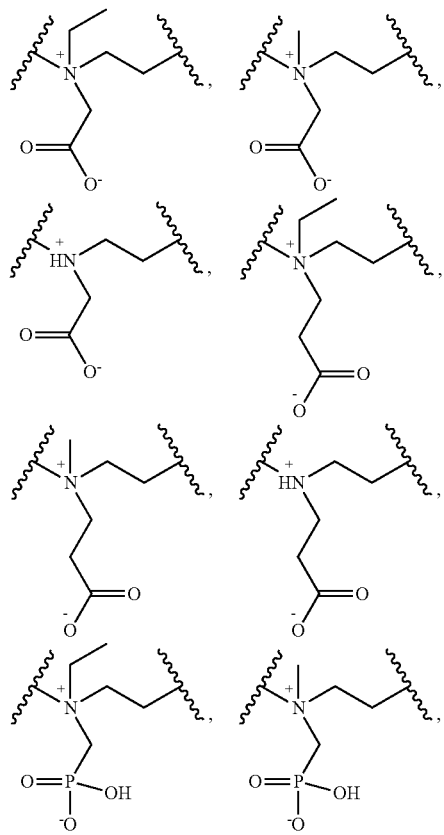

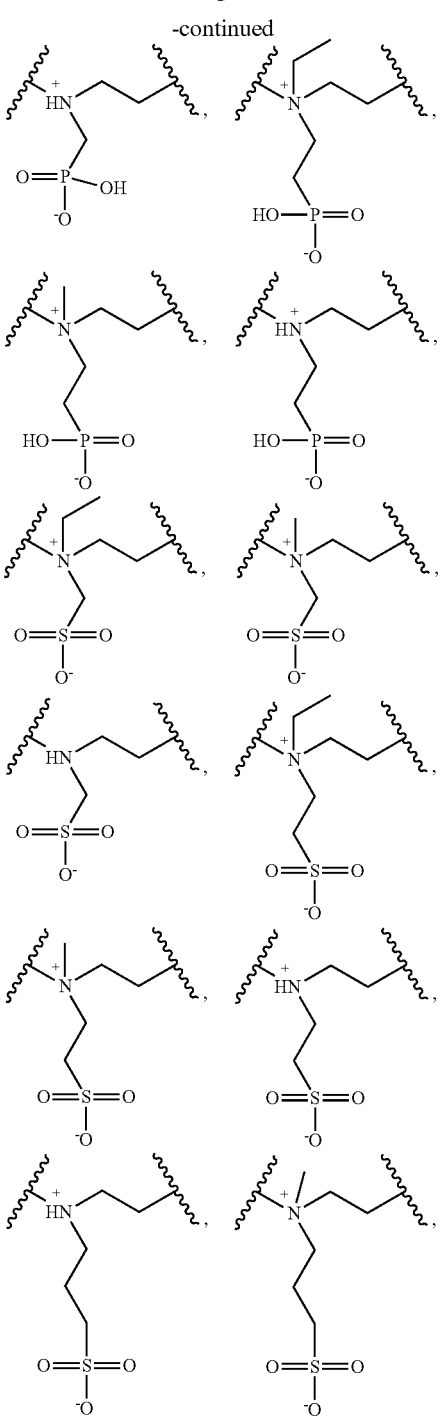

and any combination thereof.

In some embodiments, the polymer is a copolymer. The copolymer can be an alternating copolymer, a block copolymer, a random copolymer, or a graft copolymer. In some embodiments, the polymer includes one or more zwitterionic precursor repeating units having a structure of Formula (I), and one or more zwitterionic repeating units having a structure of Formula (II).

In embodiments, the polymer includes at least a first and a second zwitterionic precursor repeating unit of Formula (I), and one or more of R$^1$, R$^2$, R$^3$, R$^4$, R$^5$, R$^6$, and R$^7$ of the first zwitterionic precursor repeating unit of Formula (I) is different than one or more of $R^1$, $R^2$, $R^3$, $R^4$, $R^5$, $R^6$, and $R^7$ of the second zwitterionic precursor repeating unit of formula (I). Any number of different zwitterionic precursor repeating units can be included (e.g., a third, fourth, fifth, sixth, seventh, etc. zwitterionic precursor repeating unit). In embodiments, the polymer is an alternating copolymer. For example, in embodiments, the polymer includes alternating first and second zwitterionic precursor repeating units (e.g. in an -ABABABAB- pattern, wherein A is the first zwitterionic precursor repeating unit, and B is the second zwitterionic precursor repeating unit). In some embodiments, the polymer is a block copolymer. For example, the polymer can include alternating blocks of the first and the second zwitterionic precursor repeating unit (e.g., in an -AAABB-BAAABBB- pattern). In some embodiments, the polymer is a random copolymer. For example, in embodiments, the polymer can include a random arrangement of the first and the second zwitterionic precursor repeating units (e.g., -AABABBBABAA-).

In embodiments, the polymer includes at least a first and a second zwitterionic repeating units of Formula (II), and one or more of $R^1$, $R^2$, $R^3$, $R^4$, $R^5$, $R^6$, and $R^7$ of the first zwitterionic repeating unit of Formula (II) is different than one or more of $R^1$, $R^2$, $R^3$, $R^4$, $R^5$, $R^6$, and $R^7$ of the second zwitterionic repeating unit of Formula (II). Any number of different zwitterionic repeating units can be included (e.g., a third, fourth, fifth, sixth, seventh, etc. zwitterionic repeating unit). In embodiments, the polymer is an alternating copolymer. For example, in embodiments, the polymer includes alternating first and second zwitterionic repeating units (e.g. in an -CDCDCDCD- pattern, wherein C is the first zwitterionic repeating unit, and D is the second zwitterionic repeating unit). In some embodiments, the polymer is a block copolymer. For example, the polymer can include alternating blocks of the first and the second zwitterionic repeating unit (e.g., in an -CCCDDDCCCDDD- pattern).

In some embodiments, the polymer is a random copolymer. For example, in embodiments, the polymer can include a random arrangement of the first and the second zwitterionic precursor repeating units (e.g., -CCDCDDDCDCC-).

In some embodiments, the polymer is an alternating copolymer, for example, the polymer can include alternating zwitterionic precursor repeating units having a structure of Formula (I) and zwitterionic repeating units having a structure of Formula (II). In some cases, the polymer is a block copolymer, for example, the polymer can include alternating blocks of one or more zwitterionic precursor repeating units having a structure of Formula (I) and blocks of one or more zwitterionic repeating units having a structure of Formula (II). In some cases, the polymer is a random copolymer.

In some embodiments, the polymer is a homopolymer. That is, each of the repeating units of the polymer is the same.

Any of the polymers described herein can be further polymerized with one or more secondary repeating units and/or polymers to provide copolymers and/or hybrid polymers. That is, any of the polymers described herein can include one or more secondary repeating units. The one or more secondary repeating units can include or be derived from, for example, lactic acid, glycolic acid, caproic acid, or a combination thereof.

In some embodiments, the one or more secondary repeating units can have a structure of Formula (III):

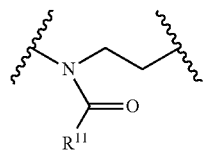

(III)

wherein $R^{11}$ is H, $-CH_3$, $-(CH_2)_nCH_3$, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-((CH_2)_nOC(O)O)(CH_2)_mOH$, $-(CH_2)_nNHC(O)(CH_2)_mOH$, $-(CH_2)_nC(O)NH(CH_2)_mOH$, $C_{1-n}$ alkenyl, $C_{1-n}$ alkynyl, $C_{6-10}$ aryl, or succinimidyl.

Any of the polymers described herein can further include a functional group capable of conjugation. Specifically, any of the polymers can include a functional group capable of conjugating to a peptide, a protein, a monosaccharide, a disaccharide, an oligo/polysaccharide, a lipid, a nucleic acid, a polymer, a target ligand molecule, a prodrug, a small molecule drug, or any combination thereof. The functional group can include, but is not limited to, acyl halide, alcohol, aldehyde, amide, amine, azo, anhydride, azide, hydrazide, toluene derivative, biotin, disulfide, carbonate, carboxylic acid, cyanate, haloalkane, ether, ester, hydroperoxide, hydrazine, isocyanide, imine, isocyanate, ketone, nitrate, nitrile, nitrite, nitro, nitroso, peroxide, benzyl, phosphodiester, vinyl sulfone, thiol, hydroxyl, imidoester, pyridylthiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, succinimidyl ester, any derivative of the any foregoing, or any combination of any of the foregoing.

In embodiments of the disclosure, the biocompatible polymer has a structure of Formula (IV):

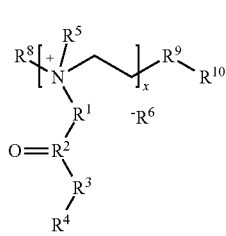

(IV)

wherein x is 1 to 10,000, and the substituents are described in detail below.

In embodiments, x can be at least 1, 10, 100, 1000, 2000, 5000, or 7000, and/or up to 10,000, 7000, 5000, 2000, 1000, 100, or 10.

Each of $R^1$, $R^2$, $R^3$, $R^4$, $R^5$, $R^6$, and $R^7$ are described above.

$R^8$ can be $-CH_3$, $-CH_2CH=CH_2$, $-(CH_2)_nCH=CH_2$, $-(CH_2)_nCH=CH_2(CH_2)_rCH_3$, $-CH_2C\equiv CH$, —

$-(CH_2)_nC\equiv CH$, $-(CH_2)_nC\equiv C(CH_2)_tCH_3$, $-(CH_2)_nCH_3$, $-(CH_2)_n CH_2N_3$, $-(CH_2)_nNH_2$, $-(CH_2)_nCH_2SH$, $-(CH_2CH_2O)_n CH_3$, $-(CH_2CH_2O)_n(CH_2)_mCH_3$, $-(CH_2CH_2O)_n(CH_2)_m N_3$, $-(CH_2CH_2O)_n(CH_2)_mSH$, $-(CH_2CH_2O)_n(CH_2)_m OH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, $-(CH_2)_nC(O)NH(CH_2)_mOH$, $C_{1-n}$ alkenyl, $C_{1-n}$ alkynyl, or $C_{6-10}$ aryl. In some embodiments, $R^3$ is $CH_3$.

$R^9$ can be O, NH, S, Se, $CH_2$, $-C(=O)O-$ or $-N=N-$. In some embodiments, $R^9$ is O. In some embodiments, $R^9$ is NH. In some embodiments, $R^9$ is S. In some embodiments, $R^9$ is Se. In some embodiments, $R^9$ is $CH_2$. In some embodiments, $R^9$ is $-N=N-$ (i.e. each of the nitrogen atoms is a part of the polymer backbone). In some embodiments, $R^9$ is $-C(=O)O-$ (i.e., each of the carbon of the carbonyl and the second oxygen is a part of the polymer backbone).

$R^{10}$ can be $-H$, $-N$, $=N$, $-CH_3$, $-CH_2CH=CH_2$, $-(CH_2)_nCH=CH_2$, $-(CH_2)_nCH=CH_2(CH_2)_tCH_3$, $-CH_2C\equiv CH$, $-(CH_2)_nC\equiv CH$, $-(CH_2)_nC\equiv C(CH_2)_tCH_3$, $-(CH_2)_nCH_3$, $-(CH_2)_nCH_2N_3$, $-(CH_2CH_2O)_nCH_3$, $-(CH_2CH_2O)_n(CH_2)_mCH_3$, $-(CH_2CH_2O)_n(CH_2)_mN_3$, $-(CH_2CH_2O)_n(CH_2)_mOH$, $-((CH_2)_nO)_m((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, $-(CH_2)_nC(O)NH(CH_2)_mOH$, vinyl sulfone, succinimidyl ester, pentafluorophenyl ester, $-(CH_2)_nC(=O)$ succinimidyl ester, $-(CH_2)_nC(=O)$ pentafluorophenyl ester, $-(CH_2CH_2O)_n(CH_2)_mC(=O)$ succinimidyl ester, $-(CH_2CH_2O)_n(CH_2)_mC(=O)$ pentafluorophenyl ester, $-SH$, $-(CH_2)_nNH_2$, $-(CH_2)_nCOOH$, $-(CH_2)_nSH$, $-(CH_2)_nNH(CH_2)_mCH_3$, $-(CH_2)_nNHCH_3$, $-(CH_2CH_2O)_n(CH_2)_mNH_2$, $-(CH_2CH_2O)_n(CH_2)_mSH$, $-(CH_2CH_2O)_n(CH_2)_mCOOH$, $C_{1-n}$ alkenyl, $C_{1-n}$ alkynyl, $C_{6-10}$ aryl, $C_{1-n}$ alkylene-SH,

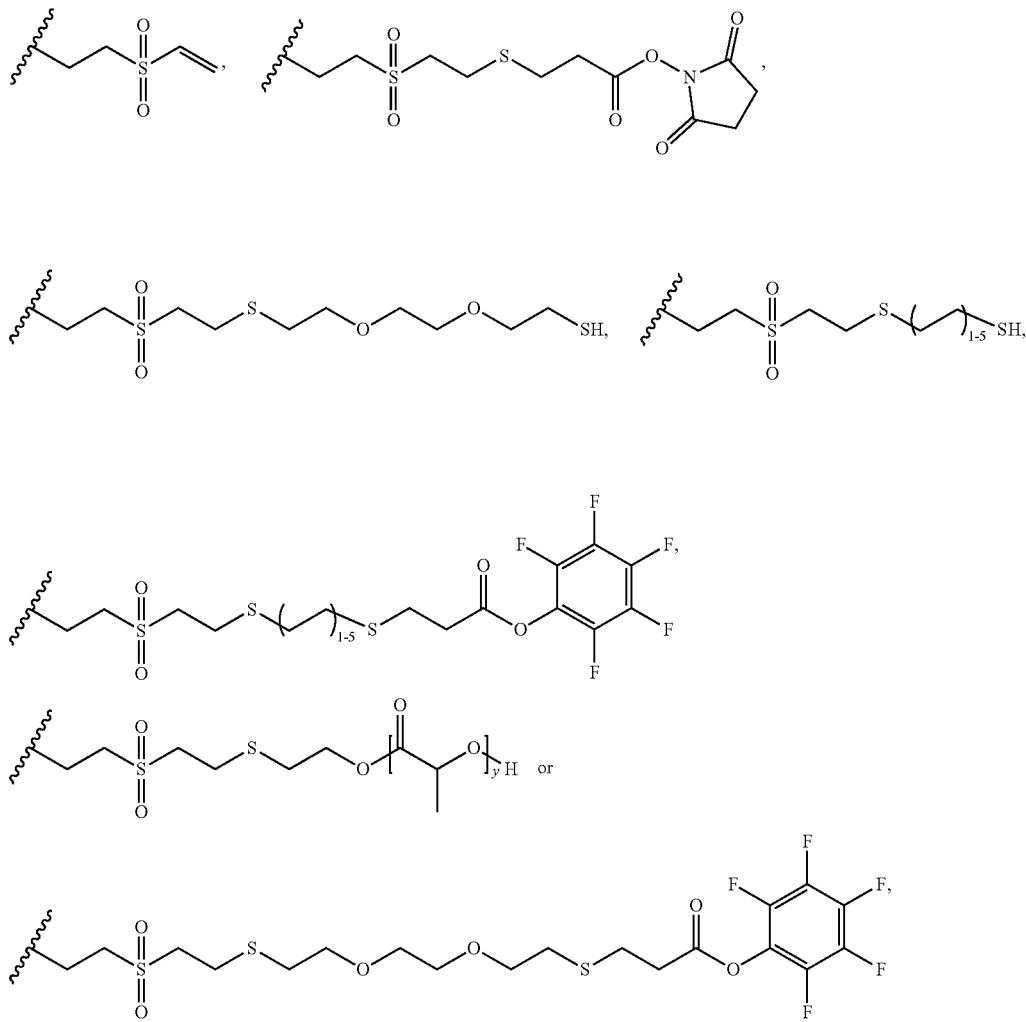

wherein y is 1 to 10,000. In embodiments, y can be at least 1, 10, 100, 1000, 2000, 5000, or 7000, and/or up to 10,000, 7000, 5000, 2000, 1000, 100, or 10. In some embodiments, $R^{10}$ is H. In some embodiments, $R^{10}$ has a structure of:

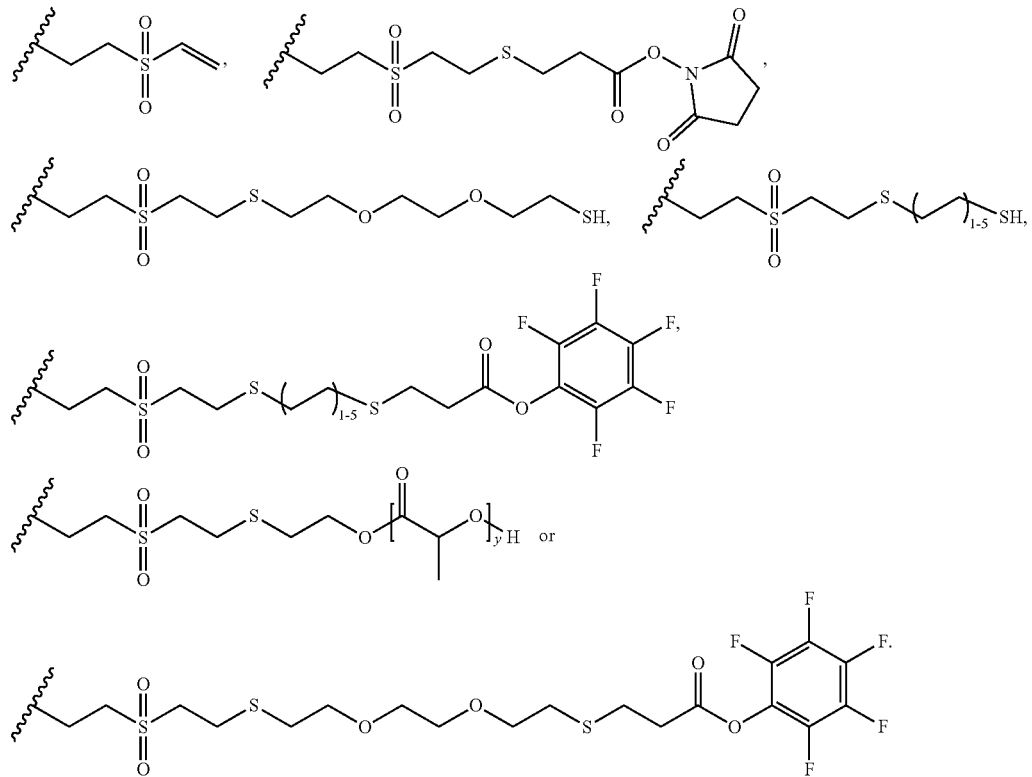

In embodiments, the biocompatible polymer can be converted to a zwitterionic biocompatible polymer through the use of hydrolysis, chemical agents, heat, radiation, electricity, oxidation, reduction, acid, and/or base. In embodiments, the polymer is hydrolyzed, giving a zwitterionic biocompatible polymer. For example, in embodiments, the hydrolyzed polymer has a structure according to Formula (V):

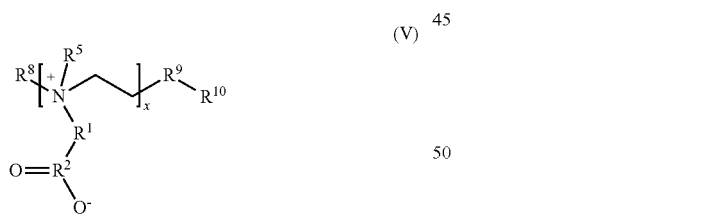

(V)

wherein each of the substituents can be selected as provided above.

In embodiments, the polymer has a structure of

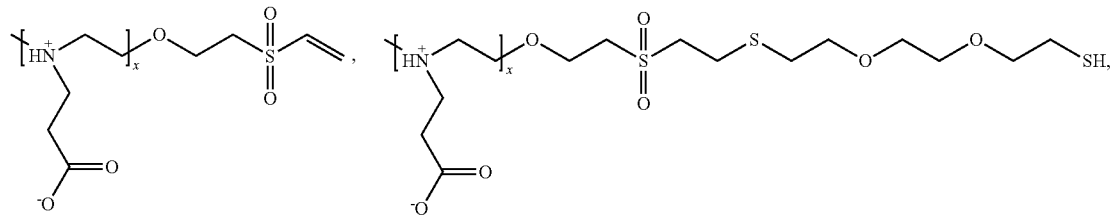

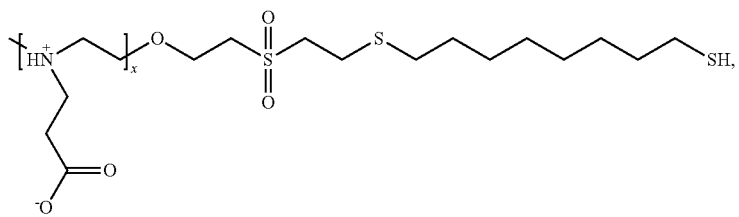
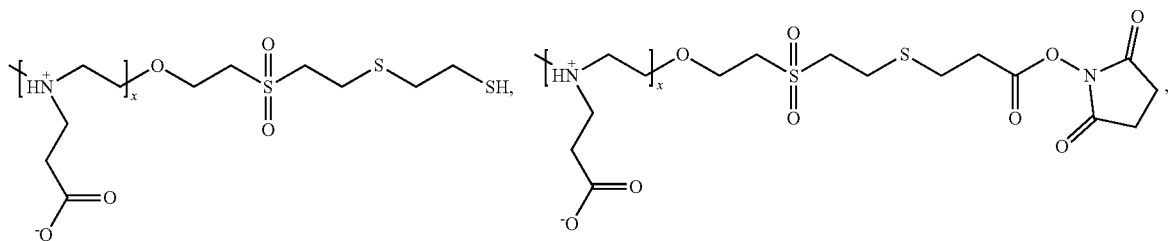
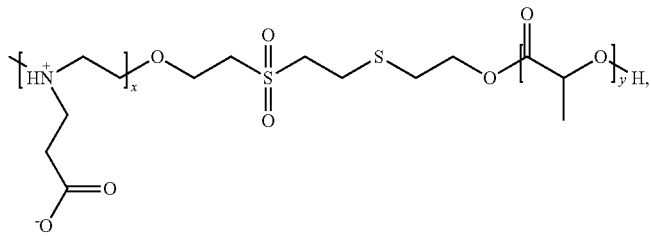
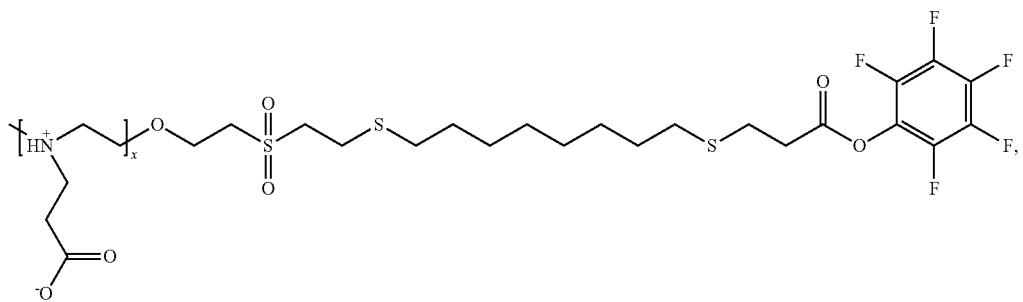
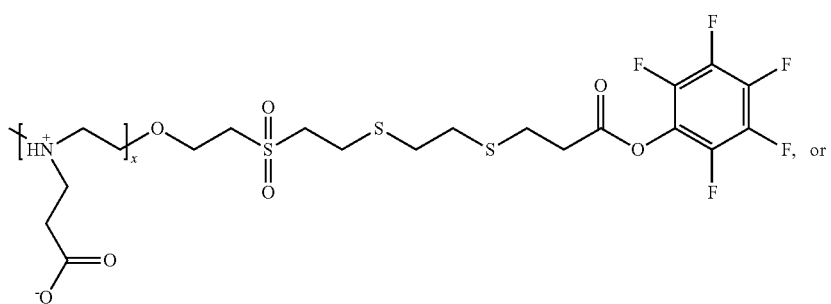
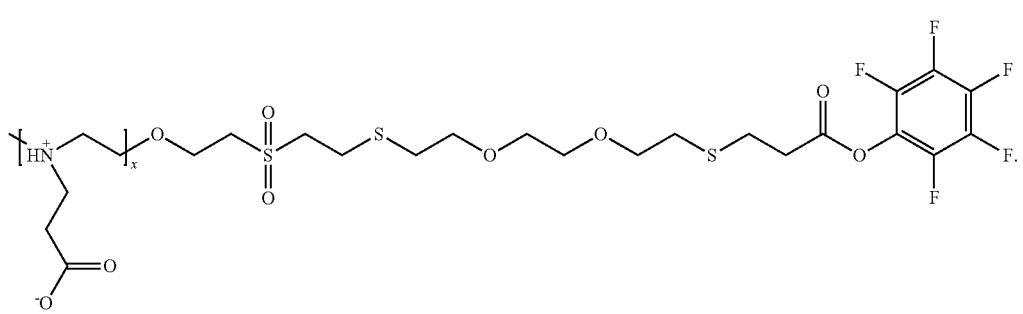

Conjugation with the Biocompatible Polymer

In embodiments, the polymer can further include one or more functional groups capable of conjugation to a target. For example, the one or more functional groups can be capable of conjugating to any one or more of a peptide, a protein, a monosaccharide, a disaccharide, an oligo/polysaccharide, a lipid, a nucleic acid, a polymer, a targeting ligand molecule, a prodrug, and a small molecule drug. Selection of a functional group for conjugation to a given target can be done as is known in the art. Accordingly, embodiments of the disclosure include conjugated polymers and hybrid polymers, in which the any one or more polymer disclosed herein is conjugated to a peptide, a protein, a monosaccharide, a disaccharide, an oligo/polysaccharide, a lipid, a nucleic acid, a polymer, a targeting ligand molecule, a prodrug, a small molecule drug, or any combination thereof.

In embodiments, the target, such as a peptide or a protein, includes at least one amino acid residue capable of binding to the polymer. In embodiments, the polymer is conjugated to the peptide or protein via the thiol group of a cysteine residue, via the amine group of a lysine residue, via the imidazole group of a histidine residue, via the phenol group of a tyrosine residue, via the carboxylate of a aspartic acid or glutamate residue, via the amine group at the N-terminal of a peptide, via the carboxylate group at the C-terminal of a peptide, via a functional group in a non-natural amino acid, or any combination thereof. The type of peptide or protein is not particularly limited. For example, in embodiments, the peptide or protein can include matrix metalloproteinase (MMP), an antibody, an interferon, an interleukin, insulin, a glucogon-like peptide, an enzyme, a cationic peptide, an anionic peptide, a lipoprotein, a glycoprotein, albumin, Fv, an antigen, an antigen-binding fragment (Fab), a single-chain variable fragment, an enzyme cutting sequence, LHRH peptide, RGD peptide, or any combination thereof.

In embodiments, the polymer can be conjugated to a monosaccharide. The monosaccharide can include, but is not limited to, glucose, fructose, galactose, mannose, ribose, deoxyribose, galactosamine, glucosamine, sialic acid, N-acetylglucosamine, N-acetylgalactosamine, sulfoquinovose, ascorbic acid, mannitol, glucuronic acid, α-D-glucopyranose, β-D-glucopyranose, psicose, mannosamine, N-acetylmannosamine, allose, altrose, gulose, idose, talose, sorbose, tagatose, or any combination thereof.

In embodiments, the polymer can be conjugated to a disaccharide. The disaccharide can include, but is not limited to, sucrose, lactulose, lactose, maltose, cellobiose, chitobiose, kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, xylobiose, or any combination thereof.

In embodiments, the polymer can be conjugated to an oligo/polysaccharide. The oligo/polysaccharide can include, but is not limited to, starch, cellulose, dextran, chitin, glycosaminoglycans, mannan, dextrin, agar, agarose, alginic acid, alguronic acid, amylose, alpha glucan, amylopectin, beta-glucan, callose, carrageenan, cellodextrin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin, or any combination thereof. In embodiments, the oligo/polysaccharide includes dextran.

In embodiments, the polymer can be conjugated to a lipid. The lipid can include, but is not limited to, cholesterol, phospholipids, sphingolipids, N-palmitoylglycine, fatty acid, coenzyme Q6, prostaglandin, monoglucosyl diacylglycerol, glycerides, eicosanoids, PAHSA, phosphatidylethanolamine, phosphatidylcholine, phosphatidylglycerol, phosphatidylserine, sphingomyelin, ganglioside, lipopolysaccharide, phosphatidylinositol, or any derivative of the foregoing.

In embodiments, the polymer can be conjugated to a nucleic acid. The nucleic acid can include, but is not limited to, deoxyribosenucleic acids (DNA), ribonucleicacids (RNA), aptamers, DNA/RNA hybrids, any derivatives thereof, and any combinations thereof.

In embodiments, the polymer can be conjugated to a small molecule drug. The small molecule drug can include, but is not limited to, one or more of folate, abiraterone acetate, brentuximab vedotin, trastuzumab emtansine, afatinib, everolimus, imiquimod, pemetrexed disodium, pemetrexed, palonosetron, chlorambucil, nelarabine, axitinib, belinostat, bleomycin, bortezomib, cabozantinib-S-malate, camptothecin, capecitabine, ceritinib, daunorubicin, crizotinib, dabrafenib, dasatinib, degarelix, docetaxel, doxorubicin, epirubicin, eribulin, etoposide, raloxifene, fulvestrant, methotrexate, pralatrexate, eribulin mesylate, topotecan, ibritumomab tiuxetan, ibrutinib, irinotecan, ixabepilone, cabazitaxel, ado-trastuzumab emtansine, lenalidomide, leuprolide acetate, vincristine, mitomycin C, mitoxantrone, nelarabine, paclitaxel, prednisone, eltrombopag olamine), raloxifene hydrochloride, lenalidomide, omacetaxine mepesuccinate), bexarotene, temsirolimus, bendamustine hydrochloride, vinblastine sulfate, vinblastine sulfate, vincristine sulfate, vinorelbine tartrate, vorinostat, capecitabine, ipilimumab, and goserelin acetate.

In embodiments, the polymer can be conjugated to a polymer. The polymer can include, but is not limited to, polylactic acid, polycaprolactone. Polystyrene (PS), polyester, polyandyride, polysaccharide, polyamide, polyethylene (HDPE), polypropylene (PP), polyvinyl chloride (PVC), nylon, nylon 6, nylon 6,6, polytetrafluoroethylene (PTFE), polyurethanes (TPU), poly(vinylidene chloride), polyacrylonitrile, poly(methyl methacrylate), poly(vinyl acetate), cis-olyisoprene, polychloroprene, poly(methacrylate), polyacrylate, polyacrylamide, polymethacrylamide, polyvinyl alcohol, poly ethylene glycol, poly propylene glycol, polylactide, poly(lactide-co-poly(glycolide), polycarbonate, poly(acrylic acid), oly(acrylamide), poly(dimethylsiloxane), poly(vinylidene fluoride), poly(allylamine hydrochloride), polyethyleneimide, poly(ethylene terephthalate), poly(methylhydrosiloxane), poly(acrylic acid sodium salt), poly(tetrahydrofuran), poly(ethyl methacrylate), poly(butyl methacrylate), poly(propylene carbonate), polypeptide, poly(methacrylic acid sodium salt), poly(methacrylic acid), poly(Bisphenol A carbonate), poly(ethylene succinate), poly(chlorotrifluoroethylene), poly(ethylene adipate), poly(isobutyl methacrylate), poly(allylamine), poly(vinyl methyl ketone), poly(vinyl cinnamate), poly(propylene glycol) methacrylate, poly(benzyl methacrylate), poly(styrenesulfonic acid sodium salt), poly(pentabromophenyl methacrylate), poly(pentafluorostyrene), polylysine, polyhistidine, poly glutamic acid, polyaspartic acid, poly(2-hydroxyethyl methacrylate), poly(N-isopropylacrylamide), poly(sodium 4-styrenesulfonate), poly(4-vinylphenol), poly(L-lactide), poly(4-vinylpyridine), poly-L-proline, poly(3,4-ethylenedioxythiophene), poly(D,L-lactide-co-glycolide), poly(2-ethyl-2-oxazoline), poly(oxazoline), poly[4,5-difluoro-2,2-bis(trifluoromethyl)-1,3-dioxole-co-tetrafluoroethylene], poly(maleic anhydride-alt-1-octadecene), poly(L-lactide), poly(ethylene-co-vinyl acetate), poly(propylene glycol)-block-poly(ethylene glycol)-block-poly(propylene glycol), poly(vinylsulfonic acid, sodium salt), poly(isobutylene-alt-maleic anhydride), poly-L-arginine, poly(vinylphosphonic ac, id), poly(styrene-co-methyl methacrylate), poly(1-vinylpyrrolidone-co-vinyl acetate), poly(2-dimethylamino) ethyl methacrylate) methyl chloride quaternary salt, poly(styrene-co-maleic anhydride), poly(styrene)-block-poly(ethylene glycol), poly(methyl vinyl ether-alt-maleic acid), poly(L-lactide-co-caprolactone-co-glycolide), poly(N-isopropylacrylamide), poly(α-methylstyrene), poly(methyl vinyl ether-alt-maleic anhydride), poly(3-butylthiophene-2,5-diyl), poly(ethylene glycol)-block-poly(ε-caprolactone), poly(D,L-lactide), poly-DL-alanine, poly(ethylene glycol)-block-polylactide, poly(3,4-ethylenedioxythiophene), poly(styrene-alt-maleic acid) sodium salt, poly(styrene-co-butadiene), poly(butyl acrylate), poly(vinyl alcohol-co-ethylene), poly(methacrylic acid, sodium salt), poly(1,4-butylene terephthalate), poly(4-vinylpyridine-co-styrene), polyvinyl imidazole, polyvinyl pyridine, poly(ethylene-co-acrylic acid), poly(styrene-co-methacrylic acid, poly(styrene-co-allyl alcohol), poly[(isobutylene-alt-maleic acid, ammonium salt)-co-(isobutylene-alt-maleic anhydride)], poly-L-ornithine, poly(acrylamide-co-acrylic acid) potassium salt, poly(methyl vinyl ether), poly(1,4-butylene succinate), poly(ethylene-co-glycidyl methacrylate), poly(vinylbenzyl chloride), Poly(styrene)-block-poly(acrylic acid), azide terminated, poly[5-methoxy-2-(3-sulfopropoxy)-1,4-phenylenevinylene] potassium salt, poly(D,L-lactide-co-caprolactone), poly(1,1,1,3,3,3-hexafluoroisopropyl acrylate), poly(3-octylthiophene-2,5-diyl), poly(tert-butyl methacrylate-co-glycidyl methacrylate), poly[9,9-bis-(2-ethylhexyl)-9H-fluorene-2,7-diyl], poly(butyl methacrylate-co-methyl methacrylate), poly(2,2,2-trifluoroethyl methacrylate), poly(4-hydroxy benzoic acid-co-ethylene terephthalate), poly(acrylonitrile-co-methyl acrylate), polycitric acid esters, poly(meth)acrylate esters, poly(2-hydroxypropyl methacrylate), poly(ethylene-co-methyl acrylate-co-glycidyl methacrylate), poly(tert-butyl methacrylate), poly(tert-butyl methacrylate), poly(ethylene-co-methacrylic acid), poly(2-ethylhexyl methacrylate), poly(2-vinylpyridine), poly(octadecyl methacrylate), poly(4-styrenesulfonic acid-co-maleic acid) sodium sal, poly[1,6-bis(p-carboxyphenoxy)hexane], poly(1-vinylpyrrolidone-co-styrene), poly(vinyl phenyl sulfide), poly(4-methyl-1-pentene), poly(1-vinylpyrrolidone)-graft-(1-triacontene), poly(N-isopropylacrylamide-co-methacrylic acid), poly(2,5 pyridine), polyimide, polybetaaminoester, polyamidoester, polyurethane, polyisocyanate, polycarbamate, or any combination of the foregoing.

In embodiments, the polymer can be conjugated to one or more of folate, peptide, galactose, a liver-affinity polysaccharide, a liver-affinity monosaccharide, an antibody, Fab, Fv, LHRH peptide, RGD peptide, low-density lipoprotein, recombinant human TNF-receptor fusion protein, interferon alfa, interferon beta, interferon gamma, interleukin 1-36, plecanatide, phenylalanine ammonia-lyase, antihemophilic factor VIII, interferon Beta-1a, naloxol, uricase, monoclonal antibody, erythropoietin, granulocyte colony-stimulating factor, growth hormone receptor antagonist, L-asparaginase, adenosine deaminase, granulocyte-colony stimulating factor, arginase, anti-VEGF aptamer, tumor necrosis factor alpha inhibitor, urate oxidase, erythropoetin receptor activators, cell adhesion peptides, RGD peptides, CRGDS, cyclic RGD peptide, Vascular endothelial growth factor (VEGF), Platelet-derived growth factor (PDGF), and epidermal growth factor.

In embodiments, the polymer has a molecular weight of about 500 Da to about 10,000,000 Da, about 500 Da to about 100,000 Da, about 1000 Da to about 5,000,000 Da, about 5000 Da to about 1,000,000 Da, about 10,000 Da to about 1,000,000 Da, about 10,000 Da to about 500,000 Da, about 50,000 Da to about 500,000 Da, or about 100,000 Da to about 250,000 Da. For example, the molecular weight ban be about 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 120,000, 140,000, 160,000, 180,000, 200,000, 250,000, 300,000, 350,000, 400,000, 450,000, 500,000, 600,000, 700,000, 800,000, 900,000, 1,000,000, 1,500,000, 2,000,000, 2,500,000, 3,000,000, 4,000,000, 5,000,000, 6,000,000, 7,000,000, 8,000,000, 9,000,000, or 10,000,000 Da.

In embodiments, polymer has a solubility in water at 20° C. of about 1 pg/mL to about 500 mg/mL. For example, the polymer can have a solubility in water at 20° C. of at least about 1 pg/mL, 500 pg/mL, 1 ng/mL, 500 ng/mL, 1 pg/mL, 500 pg/mL, 1 mg/mL, 100 mg/mL, or 250 mg/mL. For example, the polymer can have a solubility in water at 20° C. of up to about 500 mg/mL, 250 mg/mL, 100 mg/mL, 1 mg/mL, 500 pg/mL, 1 pg/mL, 500 ng/mL, 1 ng/mL, or 500 pg/mL.

Nanoparticle Using the Biocompatible Polymer

In embodiments, the polymers and/or conjugated polymers disclosed herein can be included in, a part of, and/or attached to nanoparticles. The nanoparticles can further include a drug. In embodiments, the drug can include a peptide, a protein, a nucleic acid, a small molecule drug, or any combination thereof. Each of the peptide, protein, nucleic acid, and small molecule drug can be selected as provided above.

In embodiments, nanoparticles are inorganic or organic nanopaticles. In embodiments, nanoparticles are gold nanoparticles. In embodiments, nanoparticles are iron oxide nanoparticles. In embodiments, nanoparticles are quantum dots. In embodiments, nanoparticles are carbon dots. In embodiments, nanoparticles are carbon nanotube. In embodiments, nanoparticles are dendrimer. In embodiments, nanoparticles are nanogel. In embodiments, nanoparticles are polymer nanoparticles. In embodiments, nanoparticles are polymer nanoparticles include one or more drugs. In embodiments, the drug can include a peptide, a protein, a nucleic acid, a small molecule drug, or any combination thereof. Each of the peptide, protein, nucleic acid, and small molecule drug can be selected as provided above.

Embodiments of nanoparticles of the disclosure can include a core and a shell. In embodiments, the core includes the drug. In embodiments, the shell includes and/or has attached thereto one or more biocompatible polymers. In some embodiments, the biocompatible polymer is conjugated to the drug such that the drug forms the inner core and the polymer forms the outer shell of the nanoparticle.

In some embodiments, the nanoparticle further includes a drug carrier. In embodiments wherein there is a drug carrier, the drug can be associated with and/or admixed the drug carrier. For example, the drug can be entangled, embedded, incorporated, encapsulated, bound to a surface (e.g., covalently or non-covalently bonded), or otherwise associated with the drug carrier. The biocompatible polymer can be conjugated to the drug carrier in various embodiments. In embodiments, the drug carrier includes a monosaccharide, a disaccharide, an oligo/polysaccharide, a peptide, a protein, a lipid, a dendrimer, a polymer, or any combination thereof. Each of the monosaccharide, disaccharide, peptide, or lipid can be selected as provided above. In some embodiments, the dendrimer can be, but is not limited to, poly(amidoamine), Bis-MPA dendron, polyester bis-MPA dendron, poly (ethylene glycol) linear dendrimer, dendron, hyperbranched PEG dendrimers, hyperbranched bis-MPA polyester, phosphorous dendrimers, polypropylenimine dendrimers, branched PEI, or any combination thereof. In some embodiments, the drug carrier is a liposome.

Advantageously, the nanoparticles of the disclosure can help to increase the cycle time of the drug in the body. For example, in embodiments, the nanoparticle has a blood half-life of about 5 minutes to about 4 weeks. That is, depending on the drug, the blood half-life of the nanoparticle can be at least about 5 minutes, 10 minutes, 30 minutes, 1 hour, 12 hours, 1 day, 3 days, 5 days, 1 week, 2 weeks, or 3 weeks, and/or up to about 4 weeks, 3 weeks, 2 weeks, 1 week, 5 days, 3 days, 1 day, 12 hours, 1 hour, or 30 minutes.

Methods of Making the Biocompatible Polymer

In embodiments, any of the biocompatible polymers disclosed herein can be made by reacting a polyethyleneimine having a structure of:

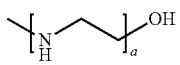

with an α,β-unsaturated ester having a structure of

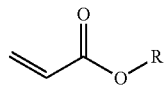

to form an N-alkylated polyethyleneimine having a structure of

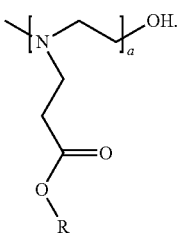

In embodiments, a is from 1 to 10,000. For example, a can be at least 1, 10, 100, 500, 1000, 2000, 3000, 4000, 5000, 6000, 7000, 8000, or 9000, and/or up to 10,000, 9000, 8000, 7000, 6000, 5000, 4000, 3000, 2000, 1000, 500, 100, or 10.

In embodiments, R is H, —CH$_3$, —(CH$_2$)$_n$CH$_3$, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —(CH$_2$CH$_2$O)$_n$CH$_2$CH$_2$OH, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_p$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, —(CH$_2$)$_n$C(O)NH(CH$_2$)$_m$OH, C$_{1-n}$ alkenyl, C$_{1-n}$ alkynyl, C$_{6-10}$ aryl, or succinimidyl. Each n, m, p, q, and r can be independently 1 to 10,000. For example, each of n, m, p, q, and r can be at least 1, 10, 100, 1000, 2000, 5000, or 7000, and/or up to 10,000, 7000, 5000, 2000, 1000, 100, or 10. In some embodiments, R is CH$_3$.

The method can further include hydrolyzing the N-alkylated polyethyleneimine to provide a zwitterionic N-alkylated polyethyleneimine.

The method can further include reacting the zwitterionic N-alkylated polyethyleneimine with a compound having a functional group capable of conjugating to a target, such as a peptide, a protein, a monosaccharide, a disaccharide, an oligo/polysaccharide, a lipid, a nucleic acid, a polymer, a targeting ligand molecule, a prodrug, a small molecule drug, or any combination thereof to form a biocompatible zwitterionic polymer. In embodiments, the reacting of the zwitterionic N-alkylated polyethyleneimine with a compound having a functional group capable of conjugating to a target occurs in the presence of a base. Examples of suitable bases include, but are not limited to, those comprising acetate, citrate, bicarbonate, carbonate, chlorate, dihydrogen phosphate, hydrogen phosphate, hydrogen sulfate, hydroxide, nitrate, nitride, nitrite, phosphate, sulfate, sulfide, sulfite, thiocyanate, thiosulfate, oxalate, perchlorate, chlorite, hypochlorite, periodate, iodate, hypoiodate, bromate, hypobromate, hypobromite, hydrogen carbonate, hydrogen sulfate, hydrogen sulfite, hydrogen oxalate, borate, tetraborate, hexfluorosilicate, tartrate, silicate, selenite, arsenate, ethanedioate, oxoethanoate, 2-hydroxyethanoate, propanoate, butanoate, pentanoate, butyrate, formate, lactate, maleate, oleate, oxalate, stearate, tarterate, urate, acrylate, glutamate, malonate, phthalate, barbiturate, cinnamate, hexanoate, folate, propionate, stearate, ascorbate, glutarate, azelate, benzilate, fumarate, gluconate, propiolate, tannate, gallate, titanate, trifluoroacetate, and diuranate.

In embodiments, the functional group capable of conjugating to a target can include anhydride, acyl halide, alcohol, aldehyde, amide, amine, azo, toluene derivative, carbonate, carboxylic acid, cyanate, haloalkane, ether, ester, hydroperoxide, isocyanide, imine, isocyanate, ketone, nitrate, nitrile, nitrite, nitro, nitroso, peroxide, benzyl, phosphodiester, phosphonic acid, phosphate, pyridinyl, sulfide, sulfone, sulfonic acid, sulfoxide, thiol, azide, alkene, alkyne, nitrone, hydrazide, hydrazone, maleimide, acrylate, methacrylate, acrylamide, methacrylamide, tetrazine, imidazole, disulfide, any derivative of the any foregoing, or any combination of any of the foregoing. For example, in some embodiments, the compound having a functional group capable of conjugating to a target is divinyl sulfone.

In embodiments, the method can further include reacting the zwitterionic N-alkylated polyethyleneimine with a second compound having a structure of

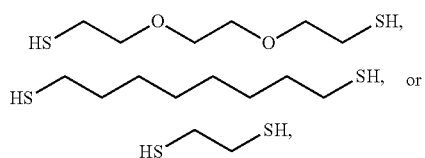

and a third compound having a structure of

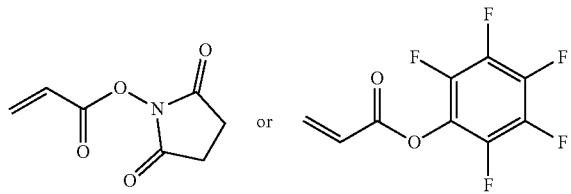 [SMILES: C=CC(=O)ON1C(=O)CCC1=O ; C=CC(=O)Oc1c(F)c(F)c(F)c(F)c1F]

to form the biocompatible zwitterionic polymer.

In some embodiments, the method can further include reacting the zwitterionic N-alkylated polyethyleneimine with a second compound having a structure selected

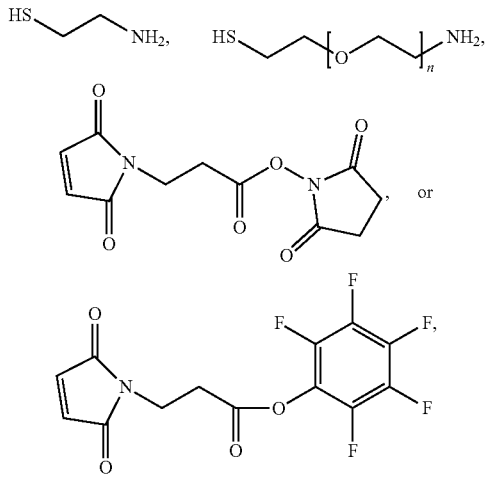

and a third compound having a structure of

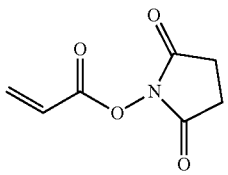

to form the biocompatible zwitterionic polymer. In embodiments, n can range from 1 to 100, 2 to 75, 3 to 50, or 4 to 25, for example 1, 2, 3, 4, 5, 6, 7, 8, 9, 10, 15, 20, 25, 30, 35, 40, 45, 50, 55, 60, 65, 70, 75, 80, 85, 90, 95 or 100.

In embodiments, the method can further include reacting the zwitterionic N-alkylated polyethyleneimine with a second compound having a structure of

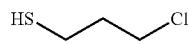

and NaN$_3$.

In embodiments, the method can further include reacting the zwitterionic N-alkylated polyethyleneimine with a second compound having a structure of

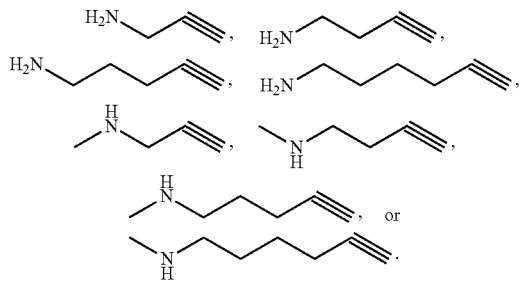

In embodiments, the method can further include conjugating a peptide, a protein, a monosaccharide, a disaccharide, an oligo/polysaccharide, a lipid, a nucleic acid, a polymer, a targeting ligand molecule, a prodrug, a small molecule drug, or any combination thereof to the zwitterionic biocompatible polymer. Each of the peptide, protein, monosaccharide, disaccharide, oligo/polysaccharide, lipid, nucleic acid, target polymer, small molecule drug can be selected as provided herein.

Polysaccharide-Anionic Peptide Conjugates and Nucleic Acid Delivery Systems

The disclosure further provides compositions and systems for nucleic acid delivery. In embodiments, a polysaccharide-anionic peptide conjugate can include a polysaccharide polymer having one or more anionic peptides attached thereto as side chains. In embodiments, the polysaccharide polymer can be a dextran. As used herein, the term "anionic peptide" refers a peptide having a sufficient number of negatively charged amino acids to render all or a substantial portion of the peptide negatively charged (anionic). As will be appreciated by those of skill in the art, certain amino acids, such as aspartic acid and glutamic acid, have negatively charged side chains (at neutral pH) that give the amino acid an overall negative charge. In embodiments, the amino acid is a natural amino acid. In embodiments, the amino acid is a non-natural amino acid.

In embodiments, a system can include a cationic complex core and the polysaccharide-anionic peptide conjugate of the disclosure. In general, the polysaccharide-anionic peptide conjugates can adsorb onto the cationic complex core. For example, in embodiments, the system can include a cationic complex core that is covered or substantially covered by the polysaccharide-anionic peptide conjugate of the disclosure. The core can include one or more nucleic acids associated with the cationic polymer for nucleic acid delivery. In embodiments, the core can include a polysaccharide-cationic peptide conjugate, such as disclosed in U.S. Pat. No. 10,058,620, the disclosure of which is incorporated herein by reference. In general, the polysaccharide-anionic peptide conjugate described herein—having a net negative charge due to the anionic peptide—can interact with the cationic complex core including the nucleic acid, to form the system for nucleic acid delivery. The polysaccharide-anionic peptide conjugates can interact with the cationic complex via electrostatic interactions, hydrogen bonds, hydrophobic interactions, and/or covalent bonds.

Nucleic acids are polymeric macromolecules essential for all known forms of life. Nucleic acids, which include DNA (deoxyribonucleic acid), RNA (ribonucleic acid) or their derivatives (such as Locked Nucleic Acid), are made from monomers known as nucleotides. Each nucleotide has three components: a 5-carbon sugar, a phosphate group, and a nitrogenous base. If the sugar is deoxyribose, the nucleic acid is DNA. If the sugar is ribose, the nucleic acid is RNA.

Locked Nucleic Acid is a novel type of nucleic acid analog containing a 2'-O, 4'-C methylene bridge—See http://www.sigmaaldrich.com/technical-documents/articles/biology/locked-nucleic-acids-faq.html#sthash.pnRVQSq4.dpuf, the disclosure of which is incorporated herein by reference in its entirety.

The particular nucleic acid to be delivered can be chosen based on the type of gene to be regulated. The particular nucleic acid can be used to suppress the activity of the gene, or in some embodiments, it may be beneficial for the nucleic acid to enhance the activity of the gene. In some embodiments, nucleic acids can also be used to inhibit gene expression in human cells. For example, RNA molecules can under a biological process known as RNA interference. RNA interference (RNAi) is a biological process in which RNA molecules inhibit gene expression, typically by causing the destruction of specific mRNA molecules. Four types of small ribonucleic acid (RNA) molecules-microRNA (miRNA), small interfering RNA (siRNA) and Short Hairpin RNA (shRNA)—are central to RNA interference. RNAs are the direct products of genes, and these small RNAs can bind to other specific messenger RNA (mRNA) molecules and either increase or decrease their expression level, for example by preventing an mRNA from producing a protein. RNA interference has an important role in defending cells against parasitic nucleotide sequences—viruses and transposons. It also influences development as well as being able to suppress the activity of proteins responsible for cellular defense induced by chemotherapy agents, such as anticancer drugs.

Small interfering RNA (siRNA), sometimes known as short interfering RNA or silencing RNA, is a class of double-stranded RNA molecules, 20-25 base pairs in length. siRNA plays many roles, but it is most notable in the RNA interference (RNAi) pathway, where it interferes with the expression of specific genes with complementary nucleotide sequences. SiRNA functions by causing mRNA to be broken down after transcription, resulting in no translation. MicroRNAs (miRNAs) are non-coding RNAs that play critical roles in a broad range of biologic processes, including differentiation, proliferation, cell cycle regulation and apoptosis. MiRNA expression is commonly deregulated in almost all types of diseases, including cancers. MiRNAs aberrantly express during cancer development, invasion and metastasis, and function as either oncogenes or tumor suppressors.

In embodiments, the nucleic acid to be delivered by the system described herein can include, but is not limited to, plasmid DNA (pDNA), oligonucleotides, aptamers, DNAzymes, RNA aptamers, RNA decoys, antisense RNA, ribozymes, small interfering RNAs (siRNA), microRNAs (miRNA), or antagomirs. In some embodiments, the nucleic acid is plasmid DNA. In some embodiments, the nucleic acid is siRNA. In some embodiments, the nucleic acid is miRNA.

The polysaccharide-anionic peptide conjugates provided herein can be used as a coating for the cationic polymer core including the nucleic acid. For example, the polysaccharide-anionic peptide conjugates described herein can form a shell around the cationic core. Cationic polymer based systems, alone, often carry high toxicity and poor blood compatibility, which can lead to the fast clearance of drug carrier in the blood or other severe complications. Advantageously, the systems of the disclosure, having a polysaccharide polymer-anionic peptide conjugate coating, can shield the cationic charge, thereby reducing the toxicity, improving the blood compatibility, and prolonging the blood circulation time of the nucleic acid delivery systems.

In some embodiments, the polysaccharide-anionic peptide conjugates can be mixed with the cationic core at a negative to positive charge ratio from about 1000:1 to about 1:1000, about 100:1 to about 1:100, or about 10:1 to about 1:10, for example about 1000:1, 750:1, 500:1, 250:1, 100:1, 75:1, 50:1, 25:1, 10:1, 1:1, 1:10, 1:25, 1:50, 1:75, 1:100, 1:250, 1:500, 1:750, or 1:1000.

Particle size and surface charge have been found to be two factors that can influence the transfection efficiency of the nucleic acid delivery systems. In some embodiments, the particle size of the system can range from about 1 nm to about 1000 nm, about 10 nm to about 900 nm, about 100 nm to about 700 nm, or about 150 to about 500 nm, for example about 1, 5, 10, 15, 20, 25, 30, 35, 40, 45, 50, 60, 70, 80, 90, 100, 150, 200, 250, 300, 350, 400, 450, 500, 600, 700, 800, 900 or 1000 nm.

As used herein, the terms "surface charge" and/or "zeta potential" are interchangeable and refer to the electric potential in the interfacial double layer (DL) at the location of the slipping plane relative to a point in the bulk fluid away from the interface. In some embodiments, the surface charge of the system can be between −50 mV and +50 mV. In some embodiments, the surface charge can be between −30 mV and +30 mV. In some embodiments, the surface charge can be between 5 mV and 15 mV. In some embodiments, the surface charge can be between 0 mV and 50 mV. In some embodiments, the surface charge can be between −20 mV and 10 mV. In some embodiments, the surface charge can be between −15 mV and 15 mV. For example, the surface charge can beat least about −50, −40, −30, −20, −10, −5, 0, 5, 10, 15, 20, 30, or 40 mV and/or up to about 50, 45, 40, 30, 20, 15, 10, 5, 0, −5, −10, −20, −30 or −40 mV.

The polysaccharide polymer of the polysaccharide-anionic peptide conjugate is both biocompatible and biodegradable. In some embodiments, the polysaccharide polymer has one or more hydroxyl or amine groups capable of bonding to acrylate, methacrylate, methacrylamide, acrylamide, maleimide, haloacetyl, divinylsulfone, pyridyl disulfide and/or thiol groups. Examples of suitable polysaccharide polymers include, but are not limited to, dextran, cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin, or any combination thereof. In some embodiments, the polymer chain is a synthetic polymer, having one or more hydroxyl or amine groups available for the bonding of acrylate, methacrylate, methacrylamide, acrylamide, maleimide, haloacetyl, divinylsulfone, and pyridyl disulfide. In embodiments, the polysaccharide polymer is dextran.

In embodiments, the molecular weight of the polysaccharide polymer can be selected to as to be sufficient to improve the blood circulation time to allow for delivery of the nucleic acids to a target cell, while minimized as much as possible to reduce cytotoxicity, which is believed to increase as a function of molecular weight. In some embodiments, the polysaccharide polymer has a weight average molecular weight of from about 500 Da to about 1,000,000 Da, about 1000 Da to about 750,000 Da, about 5000 Da to about 500,000 Da, about 10,000 Da to about 100,000 Da, or about 25,000 Da to about 75,000 Da. For example, the polysaccharide polymer can have a weight average molecular weight of about 500, 750, 1000, 2000, 3000, 4000, 5000, 6000, 7000, 8000, 9000, 10,000, 12,000, 15,000, 17,500, 20,000, 25,000, 30,000, 35,000, 40,000, 50,000, 60,000, 70,000, 80,000, 90,000, 100,000, 200,000, 300,000, 400,000, 500,000, 600,000, 700,000, 800,000, 900,000, or 1,000,000 Da. In some embodiments the polysaccharide polymer has a weight average molecular weight of about 20,000 Da.

In some embodiments, the polysaccharide polymer includes dextran and has a weight average molecular weight of from 5000 Da to about 50,000 Da. For example, the dextran can have a weight average molecular weight of at least about 5000, 7500, 10,000, 15,000, 20,000, 25,000, 30,000, 40,000 or 45,000 Da and/or up to about 50,000, 40,000, 30,000, 25,000, 20,000, 10,000, 8000, or 7500 Da. In some embodiments, the dextran has a weight average molecular weight of about 20,000 Da.

As provided herein, one or more anionic peptide side chains can be connected (e.g. conjugated) to the polysaccharide polymer. The anionic peptide side chains can be bonded to acrylate, methacrylate, methacrylamide, acrylamide, maleimide, haloacetyl, divinyl sulfone, pyridyl disulfide or other functional groups that a pre-conjugated to the polysaccharide polymers. The anionic peptide side chains can be bonded to one or more hydroxyl or amine groups on the polysaccharide polymers. It should be appreciated that the potential number of anionic peptide side chains that can be added to the polysaccharide polymer will depend upon the particular polysaccharide polymer and is limited to the total number of binding sites in each glucose (or other monosaccharide) segment of the polysaccharide polymer. One glucose unit, for example, can have at most three anionic peptide side chains or other side chains. In some of embodiments, the degree of substitution of the anionic peptide side chains to the polysaccharide polymer in the compositions can range from about 0.1% to about 300%, about 0.1% to about 50%, about 50% to about 100%, about 100%, to about 200% or about 300%, for example about 0.1%, 1%, 10%, 50%, 75%, 100%, 125%, 150%, 175%, 200%, 225%, 250%, 275%, or 300%.

The specific anionic peptide included in the polysaccharide-anionic peptide conjugate is not particularly limited and any suitable anionic peptide can be used. The anionic peptide can be linked, directly or indirectly, to the polysaccharide polymer. For example, in some embodiments, the anionic peptide may be bound to the polysaccharide polymer by a linker molecule. In some embodiments, the N-terminal of the anionic peptide may modified with 5-FAM BSA (—NH2 of N terminal), hexanoic acid, PEN, 5-FAM-Ahx, CBZ. HYNIC, stearic acid, Abz, Dansyl, KLH (—NH2 of N terminal), succinylation, acetylation, Dansyl-Ahx, lauric acid, TMR, Acryl, decanoic acid, lipoic acid, alloc, DTPA, maleimide, benzoyl, fatty Acid, MCA, biotin, FITC, myristoyl, biotin-Ahx, FITC-Ahx, octanoic acid, BOC, Fmoc, OVA (—NH2 of N terminal), Br—Ac—, Formylation, or palmitoyl. In some embodiments, the C-terminal of the anionic peptide may modified with AFC, MAPS Asymmetric 2 branches, AMC, MAPS Asymmetric 4 branches, Amidation, MAPS Asymmetric 8 branches, BSA (—COOH of C terminal), Me, Bzl, NHEt, Cysteamide, NHisopen, Ester (OEt), NHMe, Ester (OMe), OSU, Ester (OtBu), OVA (—COOH of C terminal), Ester (OTBzl), β-Nitroanilide, KLH (—COOH of C terminal), or tBu. The anionic peptide may include, without limitation, a random copolymer having the formula $E_xH_y$, $D_xH_y$, $D_xE_yH_z$, $C_xE_yH_z$, $C_xD_yH_z$, $C_wD_xE_yH_z$, $A_mB_nC_oE_xH_y$, $A_vB_wC_xD_yH_z$, or $A_uB_vC_wD_xE_yH_z$, wherein C refers to cysteine, D refers to aspartic acid, E refers to glutamic acid, H refers to histidine, and A and B refer to natural or non-natural amino acids. In embodiments, each of u, v, w, x, y, and z can be in a range of 1 to 1,000, for example 1 to 500, 1 to 100, 1 to 50, or 1 to 10. In embodiments wherein the anionic peptide has the formula $E_xH_y$, x can be 5 and y can be 1.

In embodiments, the polysaccharide-anionic peptide conjugate can include one or more linker molecules that bond the one or more anionic peptides to the polysaccharide polymer. In embodiments, the linker molecule can include methacrylate, acrylate, methacrylate, methacrylamide, acrylamide, maleimide, haloacetyl, pyridyl disulfide, divinyl sulfone, ester, acyl halide, alcohol, aldehyde, amide, amine, azo, Anhydride, azide, hydrazide, toluene derivative, biotin, disulfide, carbonate, carboxylic acid, cyanate, haloalkane, ether, ester, hydroperoxide, Hydrazone, isocyanide, imine, isocyanate, ketone, nitrate, nitrile, nitrite, nitro, nitroso, peroxide, benzyl, phosphodiester, vinylsulfone, thiol, hydroxyl, Imidoester, Pyridyldithiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester or a combination thereof. In some embodiments, the linker molecule can include methacrylate. In some embodiments, the linker molecule can include divinyl sulfone. In alternative embodiments, the anionic peptide is bonded directly to the polysaccharide polymer without the use of a linker.

In embodiments including a linker, the anionic peptide side chain will include the anionic peptide attached the linker, which in turn is attached to the polysaccharide polymer, such that the anionic peptide is distal to the polysaccharide polymer. As will be appreciated by those of ordinary skill in the art, a peptide is a short chain of amino acids linked by amide bonds. The covalent chemical bonds are formed when the carboxyl group of one amino acid reacts with the amino group of another amino acid, such that each has a C-terminal and an N-terminal. Amino acids that have been incorporated into peptides are termed "residues." Peptides are often classified according to the number of amino acid residues.

In embodiments, the anionic peptide is also biocompatible and biodegradable. In some embodiments, the peptide can also contain histidine moieties so as to facilitate the endosomal escape of the nucleic acids being delivered to improve transfection efficiency. In embodiments, the peptide can also contain histidine moieties which can react with the linker compound via the imidazole group.

In embodiments, the anionic peptide side chain can further include a crosslinker compound. The crosslinker compound can be bound to the anionic peptide at the end distal to the polysaccharide polymer For example, the polysaccharide-anionic peptide conjugate can have a general structure of: polysaccharide-linker molecule(s)-anionic peptide-crosslinker compound. Examples of suitable crosslinker compounds include, but are not limited to, lipoic acid, acyl halide, alcohol, aldehyde, amide, amine, azo, Anhydride, azide, hydrazide, toluene derivative, biotin, disulfide, carbonate, carboxylic acid, cyanate, haloalkane, ether, ester, hydroperoxide, Hydrazone, isocyanide, imine, isocyanate, ketone, nitrate, nitrile, nitrite, nitro, nitroso, peroxide, benzyl, phosphodiester, vinylsulfone, thiol, hydroxyl, Imidoester, Pyridyldithiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester.

The anionic peptide may be bonded to the rest of the components of the anionic peptide side chains (i.e., any linker and/or crosslinker compound) in any manner known in the art. The particular method will, of course, depend upon the particular anionic peptide side chain and anionic peptide involved. For example, in some embodiments, the anionic peptide side chains are formed of divinyl sulfone, an anionic peptide having the formula $NH_2$-EEEEEH-COOH, having five glutamic acid residues E and a terminal histidine ("H") on the C terminal or N terminal end, and lipoic acid. In these embodiments, the imidazole group on the terminal histidine residue can react with the alkene of the divinyl sulfone, thereby connecting the anionic peptide to the anionic peptide side chain.

The polysaccharide-anionic peptide conjugate can be a versatile platform, which can be readily conjugated with other functional groups to achieve dramatically improved therapeutic effects in the gene therapy. In some embodiments, for example, the polysaccharide-anionic peptide conjugate can further include one or more zwitterionic side chains chemically bonded to the polysaccharide polymer to increase the stability or the delivery efficiency of the delivery system. Alternatively, or additionally, the polysaccharide polymer based nucleic acid delivery system can further include one or more zwitterionic side chains chemically bonded to the anionic peptide.

In embodiments, a zwitterionic functional group and/or a biocompatible polymer having one or more zwitterionic repeating units and/or one or more zwitterionic precursor repeating units can be included in the nucleic acid delivery system. For example, the zwitterionic functional group and/or zwitterionic containing biocompatible polymer can be part of the core and conjugated to or bonded to (1) the polysaccharide backbone in a polysaccharide-cationic peptide conjugate, (2) the cationic peptide side chains in a polysaccharide-cationic peptide conjugate, (3) cationic peptide directly, or (4) cationic polymers or cationic polysaccharides directly. In embodiments in which the zwitterionic functional group and/or the zwitterionic containing biocompatible polymer is part of the core, the polymer can form a complex with nucleic acids present in the core, which is positively charged.

In embodiments, the zwitterionic functional group and/or the zwitterionic containing biocompatible polymer can be part of the coating or shell structure and can be conjugated to or bonded to (1) the polysaccharide backbone in a polysaccharide-anionic peptide conjugate, (2) the anionic peptide side chains in a polysaccharide-anionic peptide conjugate, (3) anionic peptide directly, or (4) anionic polymers or anionic polysaccharides directly.

In embodiments, the zwitterionic compound can have at least one functional group configured to bond to the polymer chain and at least one zwitterionic functional group. It should be appreciated that the zwitterionic compound may be any of the biocompatible polymers described herein, functionalized to bond to the polymer backbone. Further, the functional group or groups configured to bond to the polymer chain will, of course, depend upon the particular polysaccharide polymer backbone used but can include, without limitation, epoxide, ester, alkyl halide, acyl halide, carboxylate, sulfonate, aldehyde, or any of those provided for the biocompatible polymer, above.

As provided above, the zwitterionic side chains can be bonded at one end to the polysaccharide polymer and contain a zwitterionic functional group. Alternatively, or additionally, the zwitterionic side chains can be bonded at one end to the anionic peptide and contain a zwitterionic functional group. For example, in embodiments, the zwitterionic side chain is the biocompatible polymer described above, wherein the polymer is conjugated to the polysaccharide via the functional group that is capable of conjugating to a target. In some embodiments, the zwitterionic side chains are bonded to a glucose or other saccharide group in the polymer chain. In some embodiments, the zwitterionic side chains can be bonded to the polysaccharide polymer backbone at an available hydroxyl, amide, amine, thiol, or carboxylate group.

In embodiments, the zwitterionic functional group is provided via the biocompatible polymer described herein.

In some embodiments, the zwitterionic functional group can include a zwitterionic betaine group. In some embodiments, the zwitterionic functional group can include a carboxybetaine group, a sulfobetaine group, a phosphobetaine group, or any combination thereof. In some embodiments, the zwitterionic betaine can include, without limitation, 2-(di(methyl)(methylene)ammonio)acetate, 2-((methyl)(methylene)ammonio)acetate, 2-((methylene)ammonio)acetate 2-(bis(2-hydroxyethyl)(methylene)ammonio)acetate, 2-((2-hydroxyethyl)(methylene)(methyl)ammonio)acetate, 2-((2-hydroxyethyl)(methylene)ammonia)acetate, 3-((methyl)(methylene)ammonio) propanoate, 3-(bi(methyl)(methylene)ammonio)propanoate, (bis(2-hydroxyethyl)(methylene)ammonio)propanoate, 3-((2-hydroxyethyl)(methylene)(methyl)ammonio)propanoate, 3-((2-hydroxyethyl)(methylene)ammonia) propanoate, or combinations and/or analogs and derivatives thereof.

In some embodiments, the zwitterionic betaine group can be separated from the polysaccharide polymer backbone by from 1 to 100 carbon, oxygen, nitrogen, or sulfur atoms (i.e., at least 1, 2, 5, 10, 20, 30, 40, 50, 60, 70, 80, or 90 and/or up to 100, 90, 80, 70, 60, 50, 40, 30, 20, 10, or 5), for example, by 1, 5, 10, 15, 20, 25, 30, 35, 40, 45, 50, 55, 60, 65, 70, 75, 80, 85, 90, 95, or 100 carbon, oxygen, nitrogen, or sulfur atoms. In some embodiments, the zwitterionic side chains can include a carboxybetaine group having at least one ethanol, propanol, butanol, or pentanol group bonded to the nitrogen atom of the carboxybetaine group.

In some embodiments, the polysaccharide-anionic peptide conjugate can further include one or more reactive side chains. Like the zwitterionic side chains discussed above, the reactive side chains in these embodiments can be bound at one end to the polysaccharide polymer. Suitable functional groups for use as part of the reactive side chains include, without limitation, acyl halide, alcohol, aldehyde, amide, amine, azo, Anhydride, azide, hydrazide, toluene derivative, biotin, disulfide, carbonate, carboxylic acid, cyanate, haloalkane, ether, ester, hydroperoxide, Hydrazone, isocyanide, imine, isocyanate, ketone, nitrate, nitrile, nitrite, nitro, nitroso, peroxide, benzyl, phosphodiester, vinylsulfone, thiol, hydroxyl, Imidoester, Pyridyldithiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester, maleimide, haloacetyl, pyridyl disulfide, thiol, methacrylate, acrylate, acrylamide and/or methacrylamide groups.

It should be appreciated that the potential number of side chains that can be added to the polysaccharide-anionic peptide conjugate will depend upon the particular polysaccharide and is limited to the total number of binding sites in each glucose (or any other monosaccharide) segment of the polysaccharide polymer backbone. One glucose unit, for example, can have at most three nucleic acid delivery, zwitterionic, or reactive side chains (or any combination thereof, such that at most three side chains are present). In some of these embodiments, the degree of substitution for the polymer composition may be from 0.1% to 300%. In some embodiments, the degree of substitution of the zwitterionic and/or reactive side chains to the polysaccharide polymer in the compositions can range from about 0.1% to about 300%, about 0.1% to about 50%, about 50% to about 100%, about 100%, to about 200% or about 300%, for example about 0.1%, 1%, 10%, 50%, 75%, 100%, 125%, 150%, 175%, 200%, 225%, 250%, 275%, or 300%.

The molecular weight of the polysaccharide-anionic peptide conjugates including any linker molecules and any additional zwitterionic and/or reactive side chains) will depend upon the particular composition and its intended use. In some embodiments, the polysaccharide-anionic peptide conjugates may have a weight average molecular weight of from about 300 Da to about 10,000,000 Da, about 300 Da to about 1,000,000 Da, about 300 Da to about 100,000 Da, about 300 Da to about 10,000 Da, or about 4000 Da to about 100,000 Da, for example about 300, 500, 1000, 5000, 10,000, 25,000, 50,000, 75,000, 100,000, 150,000, 200,000, 300,000, 500,000, 750,000, 1,000,000, 2,000,000, 5,000,000, 7,000,000, 8,000,000, 9,000,000, or 10,000,000 Da.

Method of Making Polysaccharide-Anionic Peptide Conjugates

The disclosure further provides a method for forming the polysaccharide polymer compositions described herein. The general method is depicted in FIG. 1.

The method includes selecting and/or preparing any one or more of the polysaccharide polymer described above. As set forth above, these polymers should have one or more hydroxyl and/or amine groups available for bonding. A suitable polysaccharide polymer, for example, may comprise saccharides such as dextran, cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin, and/or combinations thereof.

In embodiments, the polysaccharide is then reacted with a linker molecule. Separately, the anionic peptide can be reacted with a linker molecule. That is, in embodiments, each of the polysaccharide and the anionic peptide can be conjugated to a linker molecule, wherein the linker molecules can then react to form a bond, thereby providing the polysaccharide-anionic peptide conjugates of the disclosure. For example, in embodiments, the polysaccharide polymer can be conjugated (e.g. functionalized) with divinyl sulfone (DVS). Separately, an anionic peptide (e.g., $E_5H$) can be conjugated with lipoic acid (Lip). The polysaccharide-DVS conjugate can then be reacted with the Lip-$E_5H$ conjugate to form the polysaccharide-anionic peptide of the disclosure.

As set forth above, in some embodiments, the polysaccharide polymer can further include one or more zwitterionic and/or reactive side chains chemically bonded to the polysaccharide polymer.

In embodiments, the conjugation of the zwitterionic compound to the polysaccharide polymer is carried out in the presence of a base (e.g., an organic or inorganic base). The suitability of the base will, of course, depend upon the specific polysaccharide polymer and zwitterionic compound selected, but one of ordinary skill in the art will be able to select a suitable organic or inorganic base without undue experimentation. Examples of suitable bases include, but are not limited to, sodium carbonate, pyridine, triethyl amine, Hunig's Base, 1,8-Diazabicyclo[5.4.0]undec-7-ene, Barton's Base and sodium hyzide.

In some embodiments, a polysaccharide polymer may be reacted with an ester derivative of zwitterionic betaine that contains one tertiary amine, and dibromoalkane, dichloroalkane, diepoxide, multi halide substituted alkane, or multi halide epoxide substituted alkane to produce a cationic polysaccharide composition and then hydrolyzed in suitable acidic or basic conditions to produce a polysaccharide polymer having one or more zwitterionic polymer side chains. In some embodiments, the zwitterionic compound may be a an ester derivative of zwitterionic betaine that contains a primary amine, secondary amine or tertiary amine, and a dibromoalkane, dichloroalkane, diepoxide, epichlorohydrin, a molecule with an acyl halide at one end and halide on the other end, a multi halide substituted alkane, a multi epoxide substituted alkane or a multi halide and epoxide substituted alkane. As one of ordinary skill in the art will appreciate, the selection of a suitable acid or a suitable base to hydrolyze the cationic polysaccharide will depend on the type of ester group on the cationic polysaccharide to be hydrolyzed. A methyl, ethyl, or propyl ester, for example, may be hydrolyzed under basic conditions to produce the polysaccharide polymer having one or more zwitterionic polymer side chains. A butyl ester, on the other hand, may be hydrolyzed under acid conditions to produce the polysaccharide polymer having one or more zwitterionic polymer side chains.

In some embodiments, the polysaccharide polymer can be reacted with dimethylglycine and epichlorohydrin in the presence of an organic and inorganic base and then hydrolyzed in acidic or basic conditions to produce to produce a polysaccharide polymer having one or more zwitterionic polymer side chains. In some embodiments, the polysaccharide polymer may be reacted with 3-bromopropanoyl bromide or 2-bromoacetyl bromine and a zwitterionic betaine carrying a tertiary amine in the presence of an organic and inorganic base and then hydrolyzed in acidic or basic conditions to produce to produce a polysaccharide polymer having one or more zwitterionic polymer side chains. In some embodiments, the polysaccharide polymer may be reacted with 3-bromopropanoyl bromide or 2-bromoacetyl bromine and ester derivative of zwitterionic betaine carrying a tertiary amine in the presence of an organic and inorganic base and then hydrolyzed in acidic or basic conditions to produce to produce a polysaccharide polymer having one or more zwitterionic polymer side chains.

Once all of the side chains have been added, the polysaccharide-anionic peptide conjugate can further be purified. In some embodiments, polysaccharide-anionic peptide conjugate may be purified using a dialysis membrane or by precipitation of the polysaccharide-anionic peptide conjugate into ethanol, ether, or another suitable organic solvent. The resulting polysaccharide-anionic peptide conjugate can then be dried. In some embodiments, the polymer composition can be dried by lyophilizing. In some embodiments, the polysaccharide-anionic peptide conjugate can be dried by lyophilization, vacuum, and/or heat.

Because other modifications and changes varied to fit particular conditions and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, articles, methods, and processes are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure, and following examples.

EXAMPLES

Example 1—Synthesis of Vinyl Sulfone Terminated Zwitterionic PEI Derivative

Vinyl sulfone terminated zwitterionic PEI derivatives according to embodiments of the disclosure were prepared according to the scheme below.

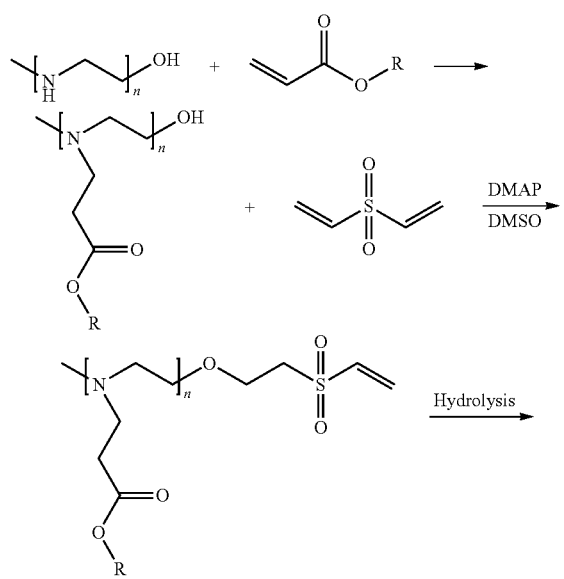

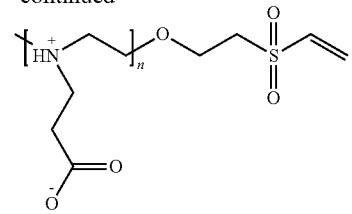

Synthesis of poly(methyl 3-(amino)propanioate ethyleneimine) (PMCBEI) (R=CH$_3$)

Polyethyleneimine with linear average $M_n$=5000 and PDI≤1.3 (1 g, 0.2 mmol) was dissolved into 50 mL ethanol. Methyl acrylate (MA) (10 g, 0.12 mol) was then added dropwise. The resulting solution was stirred for 2 days under room temperature. The unreacted methyl acrylate and ethanol were removed under reduced pressure to yield PMCBEI. $^1$H NMR (400 MHz, CDCl$_3$, ppm): 3.65 (s, 3H), 2.78 (t, 2H), 2.5 (s, 4H), 2.43 (t, 2H).

Synthesis of poly(methyl 3-(amino)propanoate ethyleneimine) vinyl sulfone (PMCBEI-VS)

PMCBEI (2.7 g, 0.18 mmol) and 4-dimethylaminopyridine (DMAP) (2.2 mg, 0.018 mmol) were first dissolved into 25 mL DMSO. Divinyl sulfone (0.08 g, 0.72 mmol) was then added. The resulting solution was stirred for two days at room temperature. After reaction, the acetonitrile was removed under reduced pressure and PMCBEI-VS was precipitated in diethyl ether solution. $^1$H NMR (400 MHz, CDCl$_3$, ppm): 6.57 (m, 1H), 6.40 (d, 1H), 6.11 (d, 1H), 3.63 (s, 3H), 2.74 (t, 2H), 2.47 (s, 4H), 2.41 (t, 2H).

Synthesis of poly(carboxybetaine ethyleneimine) vinyl sulfone (PCBEI-VS)

PMCBEI-VS (2.7 g, 0.18 mmol) was dissolved in 25 mL DI water. The resulting solution was stirred for two days under room temperature. Upon the completion of the reaction, methanol was removed under pressure and PCBEI-VS was obtained and lyophilized. $^1$H NMR (400 MHz, CDCl$_3$, ppm): 6.57 (m, 1H), 6.40 (d, 1H), 6.11 (d, 1H), 2.74 (t, 2H), 2.47 (s, 4H), 2.41 (t, 2H).

Example 2—Synthesis of Thiol Terminated Zwitterionic PEI Derivative

The synthesis generally followed the reaction scheme, below.

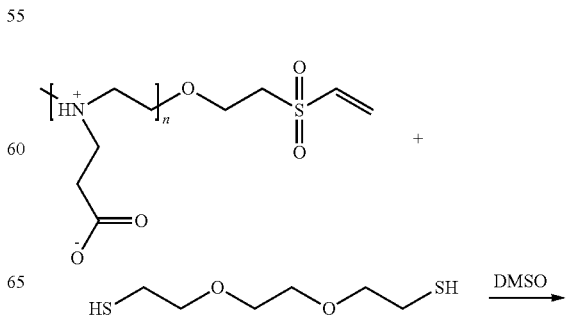

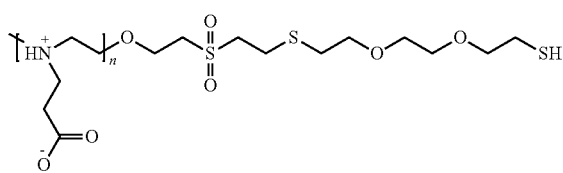

PCBEI-VS (0.5 g, 0.0375 mmol) and triphenylphosphine (TPP) (0.098 g, 0.375 mmol) were dissolved in 15 mL DMSO. 3,6-dioxa-1,8-octane-dithiol (DODT) (0.034 g, 0.188 mmol) was subsequently added. The resulting solution was stirred for 2 days at room temperature. Upon completion of the reaction, the thiol terminated PCBEI was precipitated in diethyl ether to remove TPP and residual DODT.

Example 3—Synthesis of N-hydroxysuccinimide (NHS) Ester Terminated Zwitterionic PEI Derivative The synthesis generally followed the reaction scheme, below.

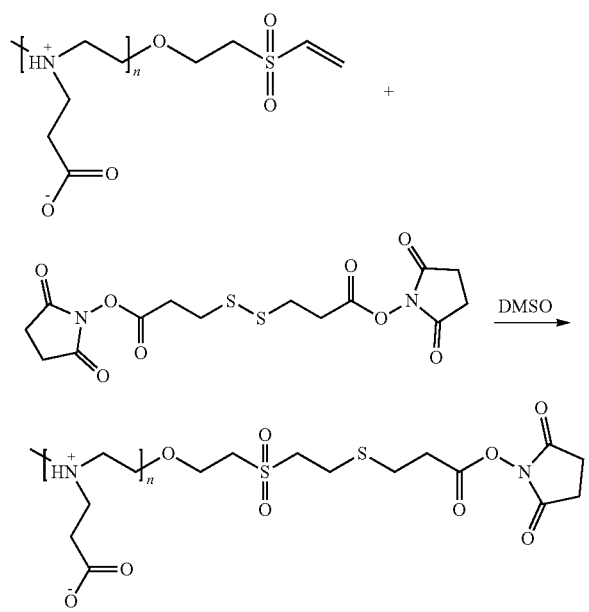

PCBEI-VS (0.1 g, 0.0075 mmol) and TPP (0.98 mg, 0.0075 mmol) were dissolved in 10 mL DMSO. Dithiobis (succinimidylpropionate) (1.5 mg, 0.0037 mmol) was then added. The resulting solution was stirred for 3 days at room temperature. Upon completion of the reaction, NHS-terminated PCBEI was precipitated in diethyl ether. $^1$H NMR (400 MHz, DMSO-d, ppm) 2.74 (t, 2H), 2.45 (s, 4H), 2.32 (t, 2H).

Example 4—Synthesis of PCBEI-co-poly(L-lactide) Zwitterionic Derivative

The synthesis generally followed the reaction scheme, below.

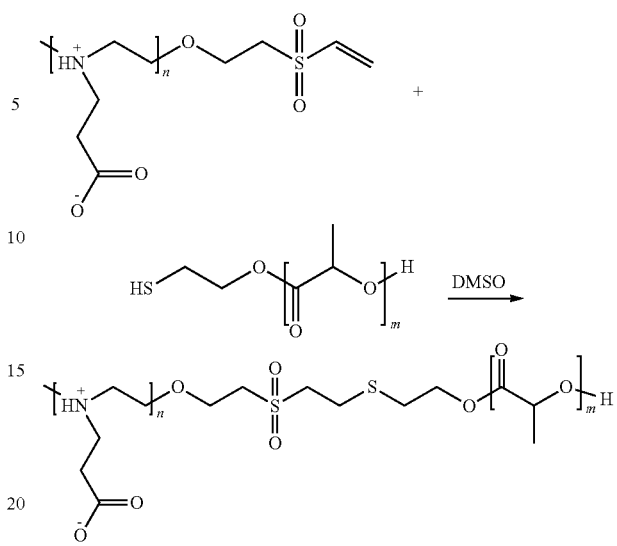

PCBEI-VS (0.5 g, 0.0375 mmol) and TPP (0.023 g, 0.9 mmol) were dissolved in 10 mL DMSO. Thiol-terminated PLA (0.22 g, 0.045 mmol) was then added. The resulting solution was stirred for 5 days at room temperature. Upon completion of the reaction, the PCBEI-co-PLA was precipitated in diethyl ether and washed with acetonitrile to remove TPP and residual PLA. $^1$H NMR (400 MHz, D$_2$O, ppm): 5.22 (q, 1H), 2.73 (t, 2H), 2.44 (s, 4H), 2.32 (t, 2H), 1.48 (d, 3H).

Example 5—Nanoparticle (NP) Formation by PCBEI-co-PLA

PCBEI-co-PLA NPs were generated by flash nanoprecipitation using a multi-inlet vortex mixer (MIVM), as previously reported (Chemical Engineering Science, 63:11 (2008), pp. 2829-2842). One of the four inlet streams was 2 mg/mL PCBEI-PLA copolymers dissolved in DMSO (Stream 1), as prepared according to Example 4. The other three inlet streams consisted of deionized water as an anti-solvent to precipitate the NPs (Streams 2, 3, and 4). The final concentration or the dilution rate and further size of the NPs were adjusted by the flow rate of streams.

At a 10× dilution, the flow rate of the PCBEI-co-PLA stream (Stream 1) and Stream 2 were set to 6 mL/min, while Streams 3 and 4 were set to 24 mL/min. The average particle size of the resulting nanoparticles was 247.6 nm.

At a 30× dilution, the flow rate of Stream 1 and Stream 2 were set 6 mL/min, while Streams 3 and 4 were set to 84 mL/min. The average particle size of the resulting nanoparticles was 103.6 nm.

At a 40× dilution, the flow rate of Stream 1 and Stream 2 were set 6 mL/min, while Streams 3 and 4 were set to 114 mL/min. The average particle size of the resulting nanoparticles was 126.1 nm.

Example 5 demonstrates that the conjugate or block co-polymer of the biocompatible polymer of the disclosure (i.e., PCBPEI) and a hydrophobic polymer (i.e., PLA) can form core-shell nanoparticles in water. Advantageously, these PCBPEI-co-PLA conjugates are expected to have high blood stability and circulation time.

Example 6—PCBEI for Gold NP Functionalization

The reaction followed the general scheme, below.

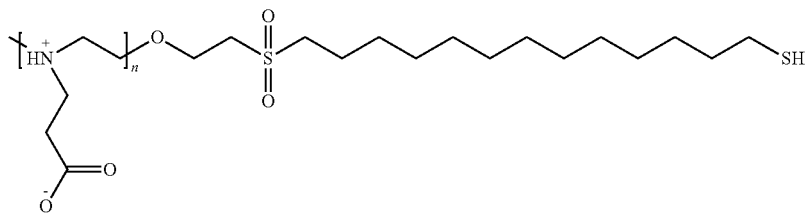 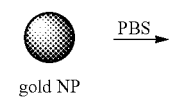

gold NP

PBS

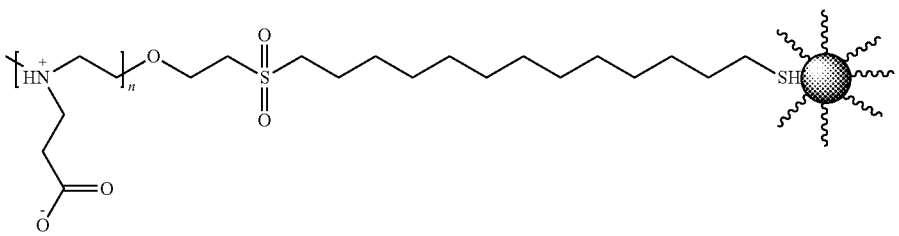

Gold nanoparticles (0.076 mg) were suspended in 5 mL PBS solution. PCBEI-SH (0.32 g, 0.024 mmol) and tris(2-carboxyethyl)phosphine (TCEP) (6.88 mg, 0.024 mmol) were then dissolved in the solution. The resulting mixture was stirred for 24 hours at 60° C. Upon completion of the reaction, the nanoparticles were centrifuged at 12,000 rpm and then washed with PBS three times to remove TCEP and residual PCBEI-SH.

The average particle size of the resulting nanoparticles was 464.8 nm.

Example 7—Conjugation of PCBEI to MMP Peptide

The reaction followed the general scheme, below.

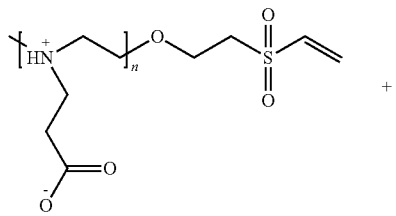

-continued

HS—MMP—SH $\xrightarrow{\text{DMSO}}$

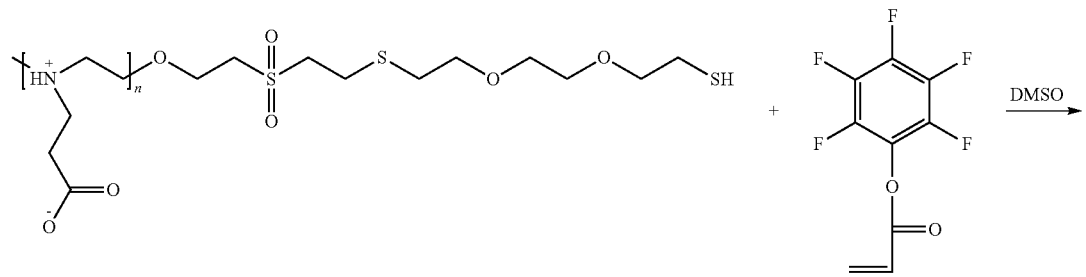

PCBEI-VS (25 mg, 0.0019 mmol) and tris(2-carboxyethyl)phosphine (TCEP) (6.89 mg, 0.027 mmol) were dissolved in 2 mL DMSO. Matrix metallopeptidase (MMP) (20 mg, 0.014 mmol) was then added. The resulting solution was stirred for 3 days at room temperature. Upon completion of the reaction, PCBEI-MMP was precipitated in diethyl ether.

Prophetic Example 8—Synthesis of Pentafluorophenyl (PFP) Ester Terminated Zwitterionic PEI Derivative Pentafluorophenyl (PFP) ester terminated PCBEI (PCBEI-PFP) is prepared according to the scheme below.

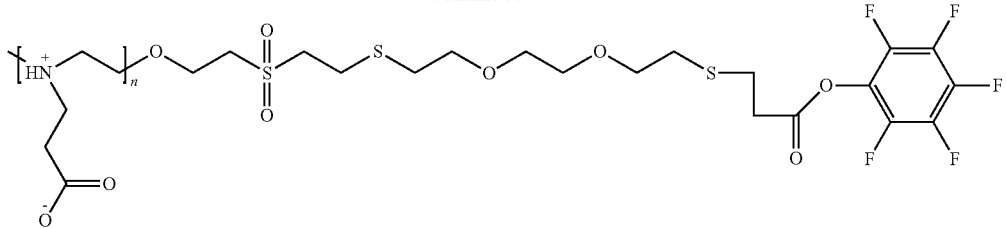

-continued

Example 9—Preparation of Dextran-Anionic Peptide Conjugate

FIG. 1 shows a schematic diagram illustrating the preparation of a dextran-anionic peptide conjugate. FIG. 1 generally shows that plasmid DNA was firstly complexed with branched polyethyleneimine and the complexes were coated with Dex-HE5-lipoic acid. Finally, the disulfide bond of lipoic acid at the N-terminal of the anionic peptides was reduced by DTT and then oxidized by oxygen in DMSO to form the crosslinked coating.

Dextran (100 mg) was dissolved in 15 mL of anhydrous DMSO. 7.5 mg of DMAP and 0.92 ml of divinyl sulfone (DVS) were added. The reaction was stirred for 24 hours at room temperature. The crude product was precipitated with excess diethyl ether from the mixture, and subsequently re-dissolved in DMSO. Ethanol was then used to wash the product three times to provide dextran conjugated with DVS (Dex-DVS).

Dex-DVS (5.6 mg) was dissolved in 100 µL of DI water. Lipoic acid bonded to an anionic peptide having 5 glutamic acid residues and 1 histidine residue (Lipoic acid-EEEEEH) (LipE5H) (25 mg) was dissolved with 100 µL of DI water. A 1 M solution of NaOH was added to neutralize the trifluoroacetic acid from peptide synthesis. The LipE5H solution was added into Dex-DVS solution, and the pH value of the mixture was adjusted to 7.0 with NaOH (1 M). Then the mixture was shaken for 48 hours at room temperature. Dex-LipE5H was purified with a Zeba spin (MWCO 7000) desalting column (Thermo Fisher Scientific, Waltham, Mass.), freeze-dried and analyzed with 1H NMR.

Example 10—Preparation and Characterization of Nucleic Acid Delivery System

Dex-LipE5H was dissolved in sterile deionized water at the concentration of 2 mg/mL and stored at 4° C. PEI (25 kDa, branched) was also dissolved in sterile deionized water at the nitrogen (N) concentration of 10 mM. Dex-LipE5H/PEI/pDNA delivery systems were prepared by two steps: preparation of cationic nanocomplexes and preparation of anionic complexes. Cationic nanocomplexes at N/P ratio of 10 were prepared via mixing PEI solution and plasmid solution (0.1 mg mL$^{-1}$). The N/P ratio was defined as the molar ratio of N in PEI to phosphate (P) in pDNA. After the mixtures were incubated at 25° C. for 30 min, Dex-LipE5H was added at different C/N/P ratios (C represents the —COOH group of peptide LipE5H), and the final anionic complexes Dex-LipE5H/PEI/plasmid were incubated for another 30 min. To further improve the stability of anionic complexes, crosslinking process was conducted. In detail, DTT was added to reduce the lipoyl units and the mixture kept for 2 hours. Subsequently, 1 µL of DMSO was added to above mixture and kept for 48 hours with stirring to facilitate the crosslinking process. The DNA-binding ability and stability of anionic complexes were evaluated by agarose gel electrophoresis assay Zetasizer system (Malvern Nano-ZS, UK).

Figure 2:
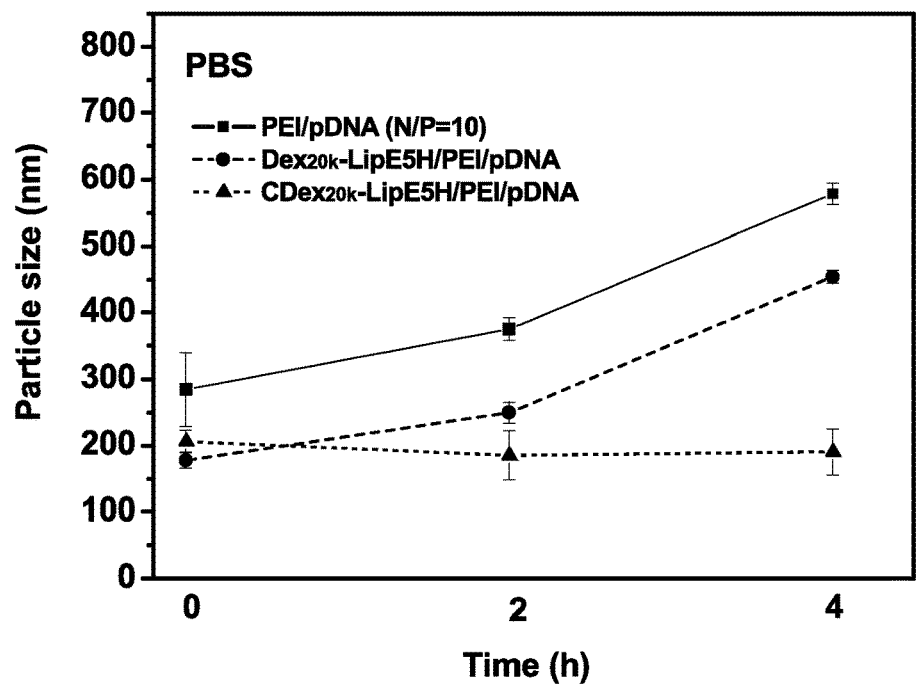
FIG. 2 is a graph of the particle size as a function of time of a system for nucleic acid delivery according to the disclosure.

The particle size of the complexes was assessed over time, and is shown in FIG. 2. FIG. 2 shows that the particle size of the crosslinked CDex20k-LipE5H/PEI/pDNA were highly stable in phosphate buffered saline (PBS). Uncrosslinked Dex20k-LipE5H/PEI/pDNA and PEI/pDNA were unstable in PBS. The stability of the complex is very important for the in vivo transfection efficiency of the nucleic acid delivery vectors. The crosslinked anionic polymer as a coating can significantly improve the stability of cationic nucleic acid carriers.

Figure 3:
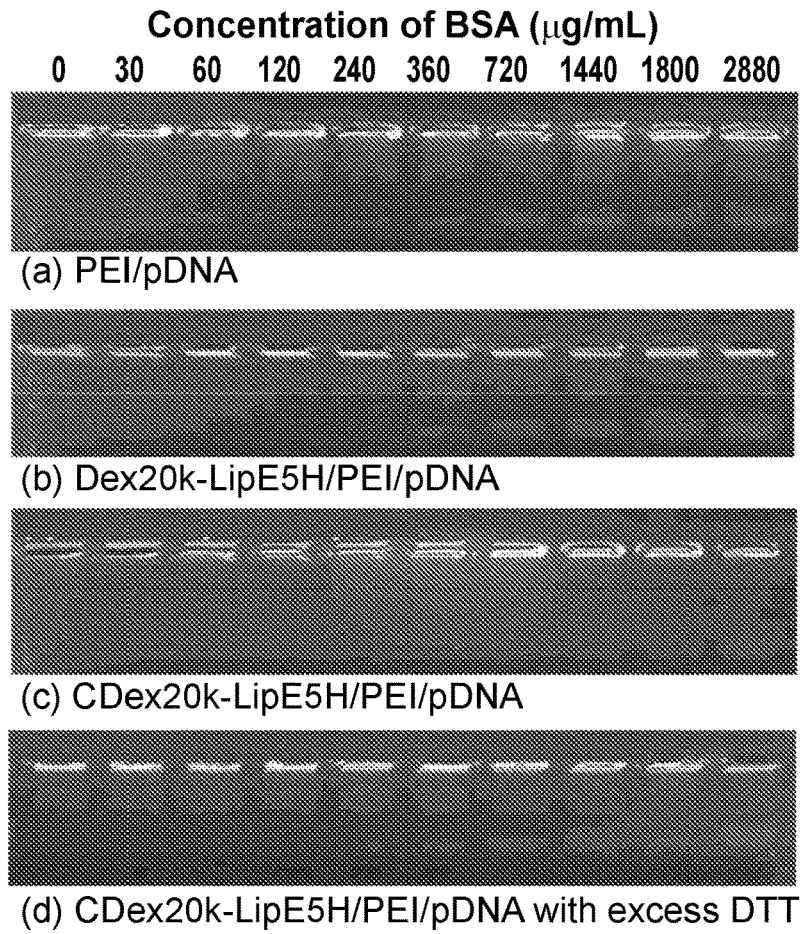
FIG. 3 is an image of the electrophoretic mobility of pDNA in the system for nucleic acid delivery according to the disclosure.

FIG. 3 shows the electrophoretic mobility of pDNA in the polyplexes of (a) PEI/pDNA (N/P=10), (b) Dex20k-LipE5H/PEI/pDNA (C/N/P=10/10/1), (c) CDex20k-LipE5H/PEI/pDNA(C/N/P=10/10/1), and (d) CDex20k-LipE5H/PEI/pDNA (C/N/P=10/10/1), with excess DTT at different BSA concentration. For a successful nucleic acid delivery, the vectors are required to bind and condense pDNA into nanostructured polymer/pDNA complexes (polyplexes), which can protect pDNA from degradation and facilitate cellular uptake. FIG. 3 shows that both uncrosslinked and crosslinked anionic coating improved the stability of the cationic delivery system. To demonstrate that crosslinked CDex20k-LipE5H/PEI/pDNA(C/N/P=10/10/1) can be used in the cell, the reducing agent, DTT, was added to the solution of CDex20k-LipE5H/PEI/pDNA(C/N/P=10/10/1). After the reduction, pDNA in the reduced CDex20k-LipE5H/PEI/pDNA(C/N/P=10/10/1) was replaced by BSA at 360 ug/ml. This result demonstrated that crosslinked anionic coating is highly stable in the blood and can be reduced in the reducing environment to help to release the nucleic acid payload inside the cell.

Cytotoxicity and Transfection Assays

Figure 4:
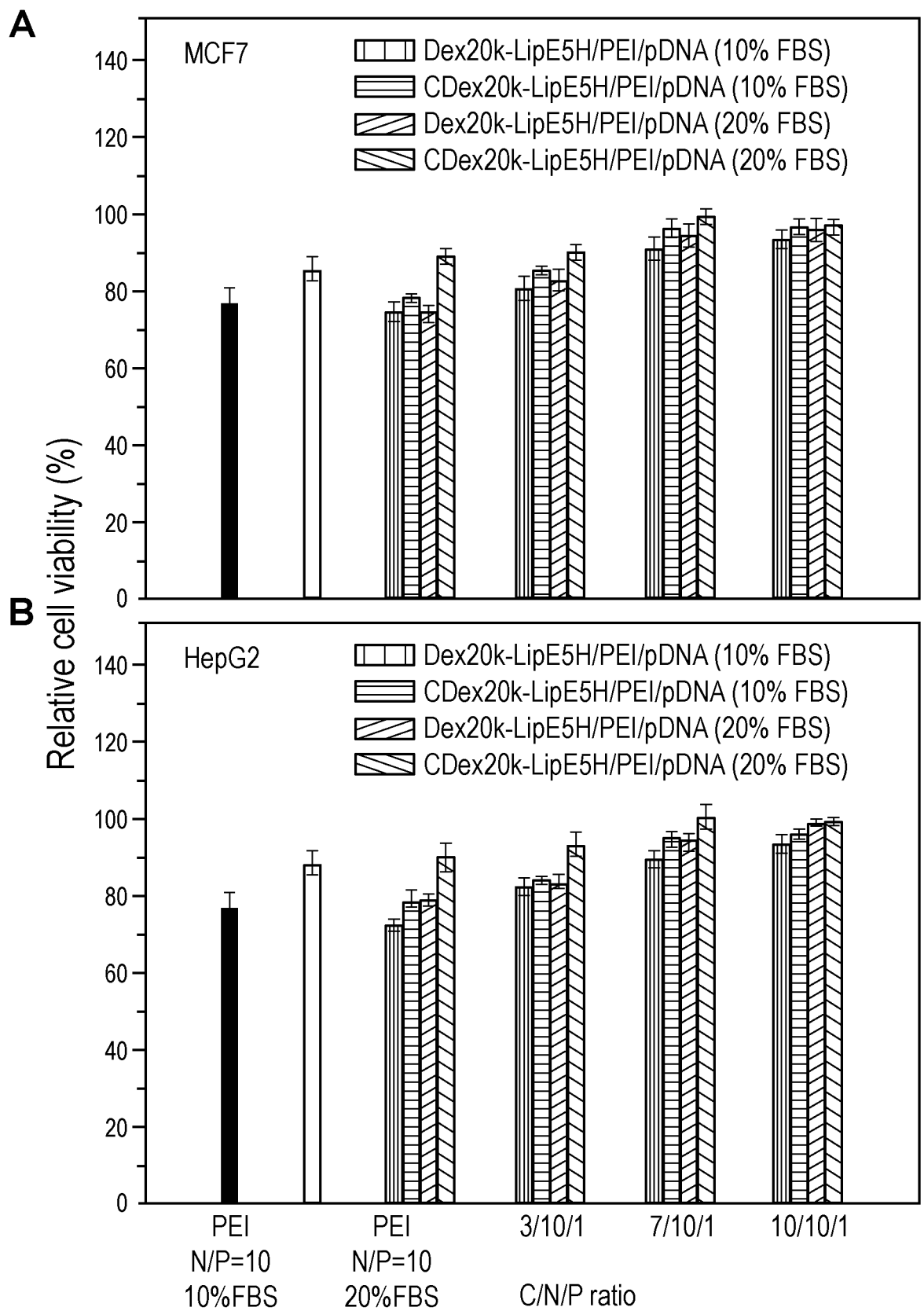
FIGS. 4A and 4B are bar graphs of the relative cell viability of MCF7 and HepG2 cells, respectively, after being treated with the system for nucleic acid delivery according to the disclosure.

The cytotoxicity of anionic nanocomplexes was assessed using MTT assays in MCF7 and HepG2 cells. The in vitro transfection efficiency mediated by Dex-LipE5H and PEI was evaluated by delivering luciferase reporter gene (plasmid pRL-CMV) in MCF7 and HepG2 cells. Results of these assays are shown in FIGS. 4 and 5, respectively.

Moreover, HepG2 cells were transfected with the corresponding Dex-LipE5H/PEI/pDNA complexes. HepG2 cells at a density of 5×10$^4$/well were seeded in 24-well plates with 0.5 mL/well of DMEM media and incubated for 24 h. The prepared Dex-LipE5H/PEI/pDNA complexes at the C/N/P ratio of 10/10/1 were added into wells, respectively. The cells were cultured continually for additional 48 h. The total RNA in HepG2 cells was extracted with TRIzol reagent. Reverse-transcribed primers and Revert Ace kit were used to form cDNA. Then, qRT-PCR was used to detect GAPDH, and PCSK9 with the corresponding PCR primers, where cDNA was stained by using SYBR Green I fluorogenic dye and amplified according to the provided protocol, and Real-time PCR amplification was carried out by a Bio-Rad CFX96 Real-Time Detection System (Hercules, Calif., USA). The PCR data were analyzed using qbase+ software (Belgium) and the commonly used $2^{-\Delta\Delta C_T}$ method.

Figure 5:
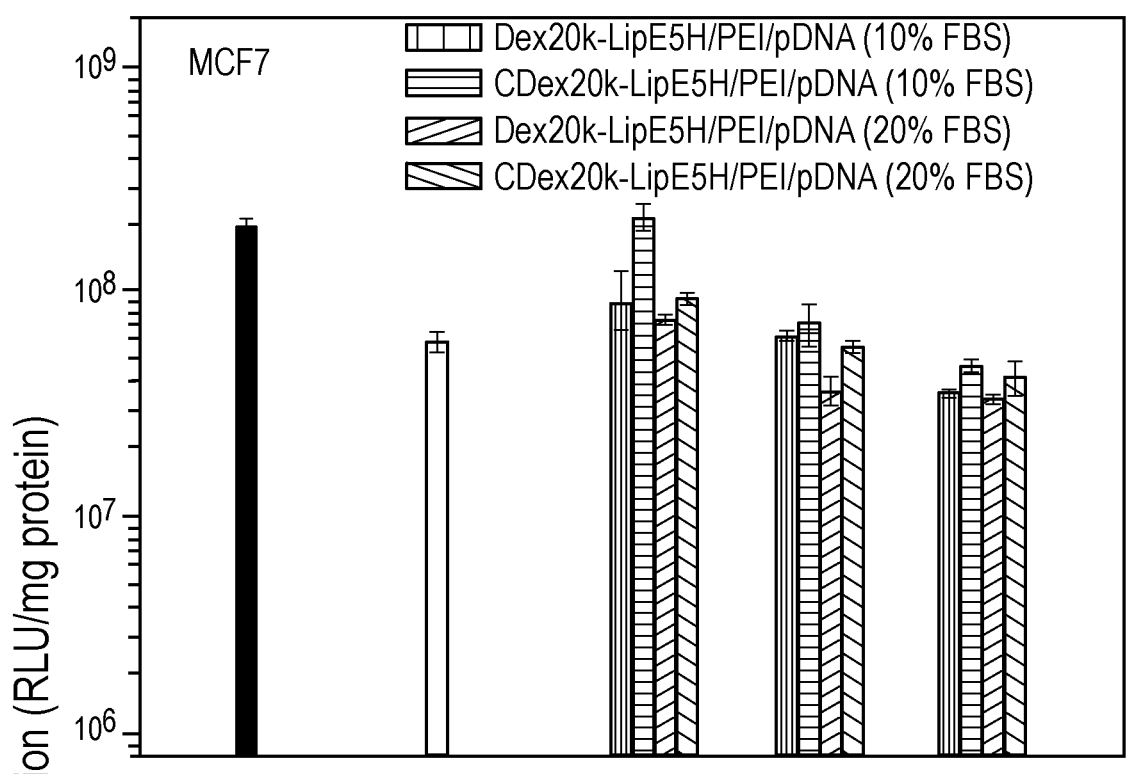
FIGS. 5A and 5B are bar graphs of the luciferase expression of MCF7 and HepG2 cells, respectively, after being treated with the system for nucleic acid delivery according to the disclosure.
Figure 5:
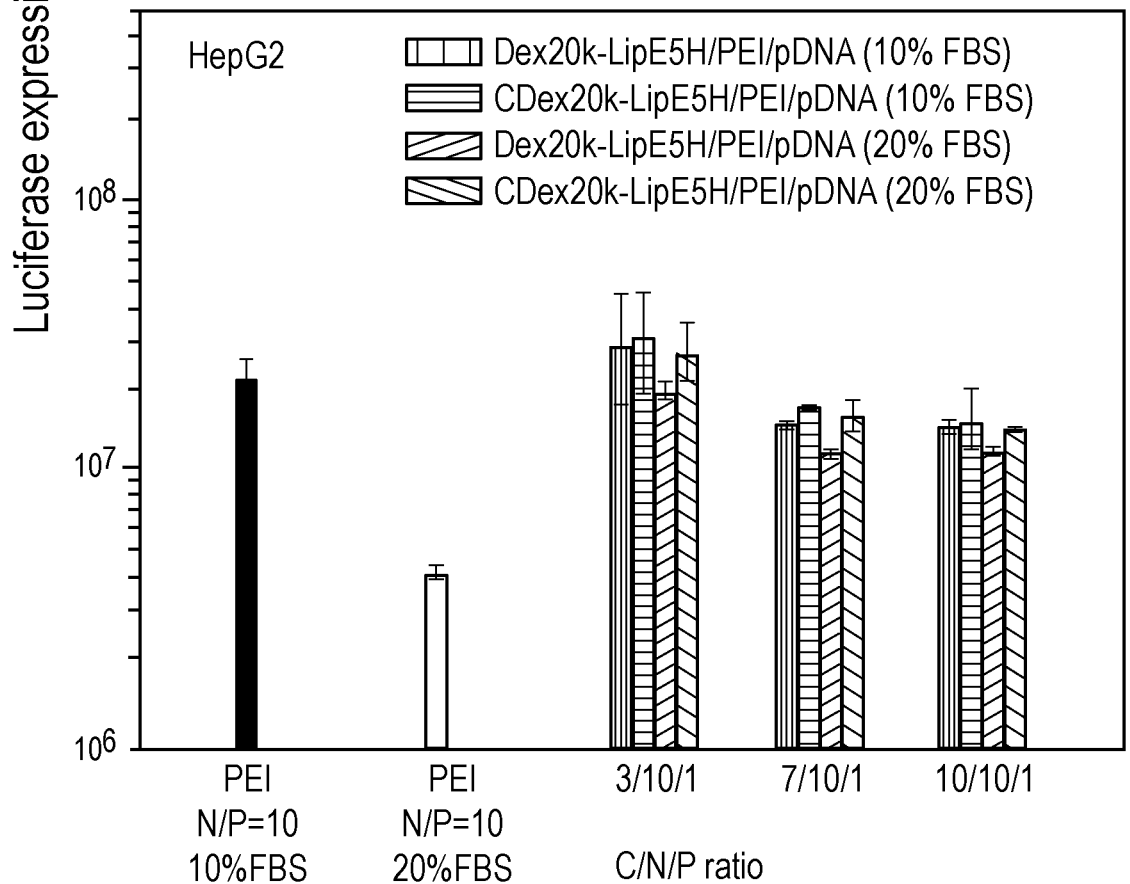

FIG. 5 shows the in vitro gene transfection efficiency of Dex20k-LipE5H/PEI/pDNA and CDex20k-LipE5H/PEI/pDNA at different C/N/P ratios compared with PEI/pDNA (at its optimal N/P ratio of 10) in a culture medium with 10% and 20% serum in MCF7 and HepG2 cell lines. High transfection efficiency is highly desired for all nucleic acid delivery system. Due to the poor blood stability and high toxicity, cationic nucleic acid delivery systems are troubled with low transfection efficiency in the high serum conditions. FIG. 5 shows that both crosslinked and uncrosslinked anionic Dex20k-LipE5H coatings significantly increased the transfection efficiency at low Dex20k-LipE5H:PEI/pDNA ratios in both MCF and HepG2 cells in the medium with 20% serum. Dex20k-LipE5H coatings significantly increased the transfection efficiency at all ratios in HepG2 in the medium with 20% serum. Significantly, HepG2 is much hard to transfect than MCF cell line.

Figure 6:
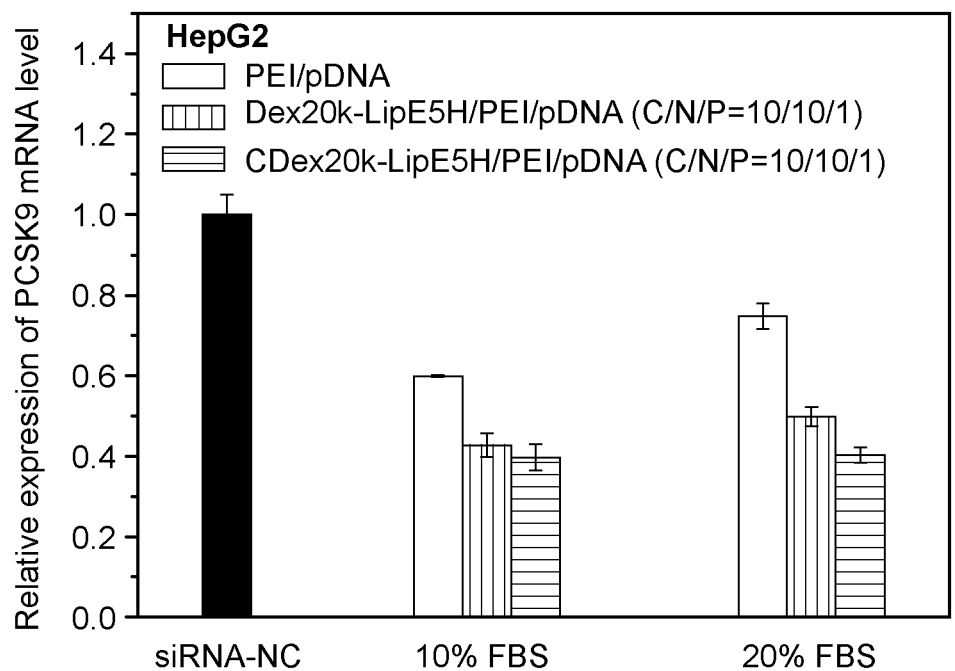
FIG. 6 is a bar graph of the relative expression of PCSK9 mRNA levels of HepG2 cells treated with the system for nucleic acid delivery according to the disclosure.

FIG. 6 shows the relative expression of PCSK9 mRNA levels treated with Dex20k-LipE5H/PEI/PCSK9 and CDex20k-LipE5H/PEI/PCSK9 at the C/N/P ratio of 10/10/1 and PEI/pDNA (at its optimal N/P ratio of 10) as the control in a culture medium with 10% and 20% serum in HepG2 cell lines. The effect of anionic coating on the transfection efficiency of siRNA was evaluated. FIG. 6 shows that both crosslinked and uncrosslinked anionic Dex20k-LipE5H coatings significantly increased the transfection efficiency of PCSK9 siRNA that can be evidenced by the higher knockdown efficiency of proprotein convertase subtilsin-kexin type 9 (PCSK9) in HepG2 cell in the medium with 20% serum. FIG. 6 demonstrates that the anionic coating significantly increased the transfection efficiency of the cationic nucleic acid delivery carriers.

Figure 7:
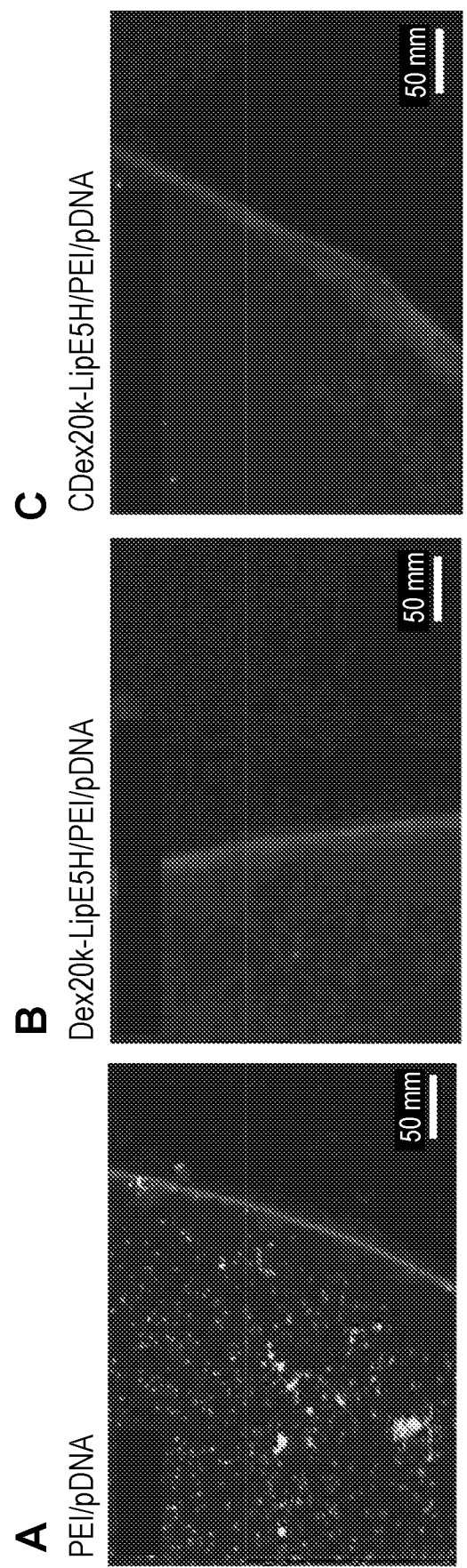
FIG. 7 are fluorescence images of protein adsorption of A) a polyethyleneimine-pDNA conjugate, B) a system for nucleic acid delivery according to the disclosure, and C) a crosslinked system for nucleic acid delivery according to the disclosure.

FIG. 7 shows the adsorption of PEI/pDNA (at its optimal N/P ratio of 10), Dex20k-LipE5H/PEI/PCSK9 and CDex20k-LipE5H/PEI/PCSK9 at the C/N/P ratio of 10/10/1 on the protein coating surface. A glass surface was coated with fibrinogen, which is one of the most adhesive proteins in the blood. Then, the adsorption of fluorescence-labeled PEI/pDNA complexes with and without anionic coatings was studied. The results, as shown in FIG. 7, showed that complexes with an anionic coating had the least amount of protein adsorption. This result indicated that the anionic coating significantly reduced the protein interaction with cationic nucleic acid delivery carriers that is needed for the safe and efficiency nucleic acid delivery.

Aspects—Set One

Aspect 1. A biocompatible polymer, comprising:
a polymer backbone comprising one or more repeating units, wherein the one or more repeating units are each individually selected from a zwitterionic precursor repeating unit of Formula (I):

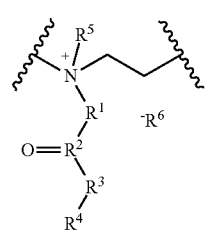

(I)

wherein $R^1$ is —$(CH_2)_n$—, —$(CH_2)_nO(CH_2)_m$—, —$(CH_2CH_2OCH_2CH_2)_n$—, —$(CH_2CH_2O)_nCH_2CH_2$—, —$(CH_2CH_2O)_n(CH_2)_m$—, —$(CH_2)_n(CH_2CH_2O)_m(CH_2)_p$—, —$(CH_2)_{1-8}C(O)O)_n(CH_2)_m$—, —$((CH_2)_{1-8}C(O)O)_n(CH_2CH_2)_m(OC(O)(CH_2)_{1-8})_p$—, —$((CH_2)_{1-8}C(O)O)_n(CH_2CH_2)_m(OC(O)(CH_2)_{1-8})_p$—, —$(CH_2C(O)O)_n(CH_2CH_2)_m(OC(O)CH_2)_p$—, —$(CH(CH_3)C(O)O)_n(CH_2CH_2)_m(OC(O)CH(CH_3))_p$—, —$(CH(CH_3)C(O)O)_n(CH_2CH_2)_m(OC(O)CH(CH_3))_p$—, —$((CH_2)_nOC(O)O)(CH_2CH_2)_m$—, —$(CH_2)_nNHC(O)(CH_2)_m$—, —$(CH_2)_nC(O)NH(CH_2)_m$—, —$(CH_2)_nS(O_2)(CH_2)_m$—, —$(CH_2)_nS(O_2)(CH_2)_m(CH_2)_t$—, —$(CH_2)_nO$—, —$(CH_2)_nO(CH_2)_m$—, —$(CH_2CH_2OCH_2CH_2)_nO$—, —$(CH_2CH_2O)_nCH_2CH_2O$—, —$(CH_2CH_2O)_n(CH_2)_mO$—, —$(CH_2)_n(CH_2CH_2O)_m(CH_2)_pO$—, —$((CH_2)_{1-8}C(O)O)_n(CH_2)_mO$—, —$((CH_2)_{1-8}C(O)O)_n(CH_2CH_2)_m(OC(O)(CH_2)_{1-8})_pO$—, —$((CH_2)_{1-8}C(O)O)_n(CH_2CH_2)_m(OC(O)(CH_2)_{1-8})_pO$—, —$(CH_2C(O)O)_n(CH_2CH_2)_m(OC(O)CH_2)_pO$—, —$(CH(CH_3)C(O)O)_n(CH_2CH_2)_m(OC(O)CH(CH_3))_pO$—, —$(CH(CH_3)C(O)O)_n(CH_2CH_2)_m(OC(O)CH(CH_3))_pO$—, —$((CH_2)_nOC(O)O)(CH_2CH_2)_mO$—, —$(CH_2)_nNHC(O)(CH_2)_mO$—, —$(CH_2)_nC(O)NH(CH_2)_mO$—, —$(CH_2)_nS(O_2)(CH_2)_mO$—, or —$(CH_2)_nS(O_2)(CH_2)_mO(CH_2)_tO$—;

$R^2$ is C, P(OR$^7$), or S(=O)

$R^3$ is O, NH, or OC(=O);

$R^4$, $R^5$ and $R^7$ are each independently H, —$CH_3$, —$(CH_2)_n$ $CH_3$, —$(CH_2CH_2O)_nCH_3$, —$(CH_2CH_2O)_n(CH_2)_m$ $CH_3$, —$(CH_2CH_2O)_n(CH_2)_mOH$, —$((CH_2)_nO)_m$ $((CH_2)_pO)_q(CH_2)_rOH$, —$(CH_2CH_2O)_nH$, —$(CH_2)_n$ OH, —$(CH_2)_nO(CH_2)_mOH$, —$(CH_2CH_2OCH_2CH_2)_nOH$, —$(CH_2CH_2O)_n$ $CH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_p$ OH, —$((CH_2)_{1-8}C(O)O)_n(CH_2CH_2)_m(OC(O)(CH_2)_{1-8})_pOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH$ $(CH_2)_mOH$, $C_{1-n}$ alkenyl, $C_{1-n}$ alkynyl, $C_{6-10}$ aryl, pentafluorophenyl, or succinimidyl;

$R^6$ is F, Cl, Br, I, acetate, citrate, bicarbonate, carbonate, chlorate, dihydrogen phosphate, hydrogen phosphate, hydrogen sulfate, hydroxide, nitrate, nitride, nitrite, phosphate, sulfate, sulfide, sulfite, thiocyanate, thiosulfate, oxalate, perchlorate, chlorite, hypochlorite, periodate, iodate, hypoiodate, bromate, hypobromate, hypobromite, hydrogen carbonate, hydrogen sulfate, hydrogen sulfite, hydrogen oxalate, borate, tetraborate, hexfluorosilicate, tartrate, silicate, selenite, arsenate, ethanedioate, oxoethanoate, 2-hydroxyethanoate, propanoate, butanoate, pentanoate, butyrate, formate, lactate, maleate, oleate, oxalate, stearate, tarterate, urate, acrylate, glutamate, malonate, phthalate, barbiturate, cinnamate, hexanoate, folate, propionate, stearate, ascorbate, glutarate, azelate, benzilate, fumarate, gluconate, propiolate, tannate, gallate, titanate, trifluoroacetate, or diuranate;

each n, m, p, q, and r is independently 1 to 10,000; and, t is 0 to 10,000.

Aspect 2. The biocompatible polymer of aspect 1, wherein one or more of the zwitterionic precursor repeating unit is a zwitterionic repeating unit.

Aspect 3. The biocompatible polymer of aspect 2, wherein the zwitterionic repeating unit has a structure of Formula (II):

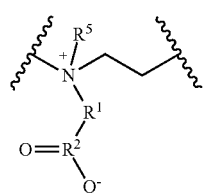

(II)

Aspect 4. The biocompatible polymer of any one of aspects 1-3, wherein the polymer comprises one or more zwitterionic precursor repeating units having a structure of Formula (I), and one or more zwitterionic repeating units having a structure of Formula (II).

Aspect 5. The biocompatible polymer of aspect 4, wherein the polymer is a copolymer comprising alternating zwitterionic precursor repeating units having a structure of Formula (I) and zwitterionic repeating units having a structure of Formula (II).

Aspect 6. The biocompatible polymer of aspect 4 or 5, wherein the polymer is a block copolymer comprising alternating blocks of one or more zwitterionic precursor repeating units having a structure of Formula (I) and blocks of one or more zwitterionic repeating units having a structure of Formula (II).

Aspect 7. The biocompatible polymer of any one of aspects 1-6, wherein $R^3$ is NH.

Aspect 8. The biocompatible polymer of any one of aspects 1-6, wherein $R^3$ is O.

Aspect 9. The biocompatible polymer of any one of aspects 1-6, wherein $R^3$ is OC(=O).

Aspect 10. The biocompatible polymer of any one of aspects 1-9, wherein $R^2$ is C.

Aspect 11. The biocompatible polymer of aspect 9, wherein $R^1$ is —(CH$_2$)$_n$—, —(CH$_2$)$_n$O(CH$_2$)$_m$—, —(CH$_2$CH$_2$OCH$_2$CH$_2$)$_n$—, —(CH$_2$CH$_2$O)$_n$CH$_2$CH$_2$—, —(CH$_2$CH$_2$O)$_n$(CH$_2$)$_m$—, —(CH$_2$)$_n$(CH$_2$CH$_2$O)$_m$(CH$_2$)$_p$—, —((CH$_2$)$_{1-8}$C(O)O)$_n$(CH$_2$)$_m$—, —((CH$_2$)$_{1-8}$C(O)O)$_n$(CH$_2$CH$_2$)$_m$(OC(O)(CH$_2$)$_{1-8}$)$_p$—, —((CH$_2$)$_{1-8}$C(O)O)$_n$ (CH$_2$CH$_2$)$_m$(OC(O)(CH$_2$)$_{1-8}$)$_p$—, —(CH$_2$C(O)O)$_n$ (CH$_2$CH$_2$)$_m$(OC(O)CH$_2$)$_p$—, —(CH(CH$_3$)C(O)O)$_n$ (CH$_2$CH$_2$)$_m$(OC(O)CH(CH$_3$))$_p$—, —(CH(CH$_3$)C(O)O)$_n$ (CH$_2$CH$_2$)$_m$(OC(O)CH(CH$_3$))$_p$—, —((CH$_2$)$_n$OC(O)O) (CH$_2$CH$_2$)$_m$, —(CH$_2$)$_n$NHC(O)(CH$_2$)$_m$—, —(CH$_2$)$_n$C(O) NH(CH$_2$)$_m$, —(CH$_2$)$_n$S(O$_2$)(CH$_2$)$_m$—, or —(CH$_2$)$_n$S(O$_2$) (CH$_2$)$_m$O(CH$_2$)$_t$—.

Aspect 12. The biocompatible polymer of any one of aspects 1-9, wherein $R^2$ is P(OR$^7$).

Aspect 13. The biocompatible polymer of any one of aspects 1-9, wherein $R^2$ is S(=O).

Aspect 14. The biocompatible polymer of any one of aspects 1-13, further comprising a functional group capable of conjugating to a peptide, a protein, a monosaccharide, a disaccharide, an oligo/polysaccharide, a lipid, a nucleic acid, a polymer, a targeting ligand molecule, a prodrug, a small molecule drug, or any combination thereof.

Aspect 15. The biocompatible polymer of aspect 14, wherein the functional group is selected from the group consisting of acyl halide, alcohol, aldehyde, amide, amine, azo, anhydride, azide, hydrazide, toluene derivative, biotin, disulfide, carbonate, carboxylic acid, cyanate, haloalkane, ether, ester, hydroperoxide, hydrazone, isocyanide, imine, isocyanate, ketone, nitrate, nitrile, nitrite, nitro, nitroso, peroxide, benzyl, phosphodiester, vinylsulfone, thiol, hydroxyl, imidoester, pyridyldithiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester, any derivative of the any foregoing, and any combination of any of the foregoing.

Aspect 16. The biocompatible polymer of any one of the preceding aspects, wherein the polymer comprises one or more zwitterionic repeating units having a structure selected from the group consisting of:

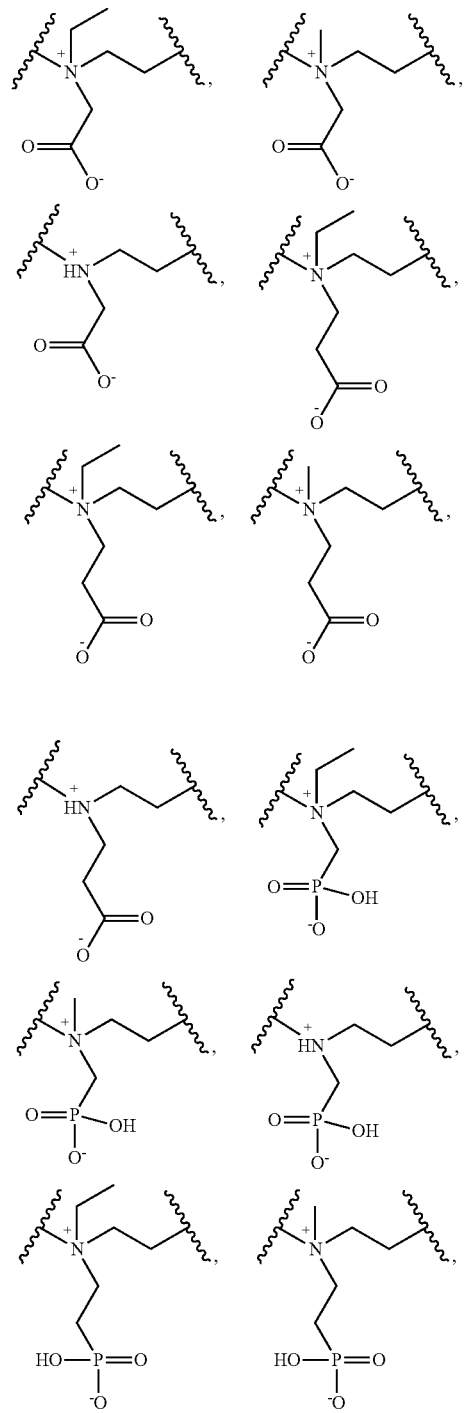

-continued

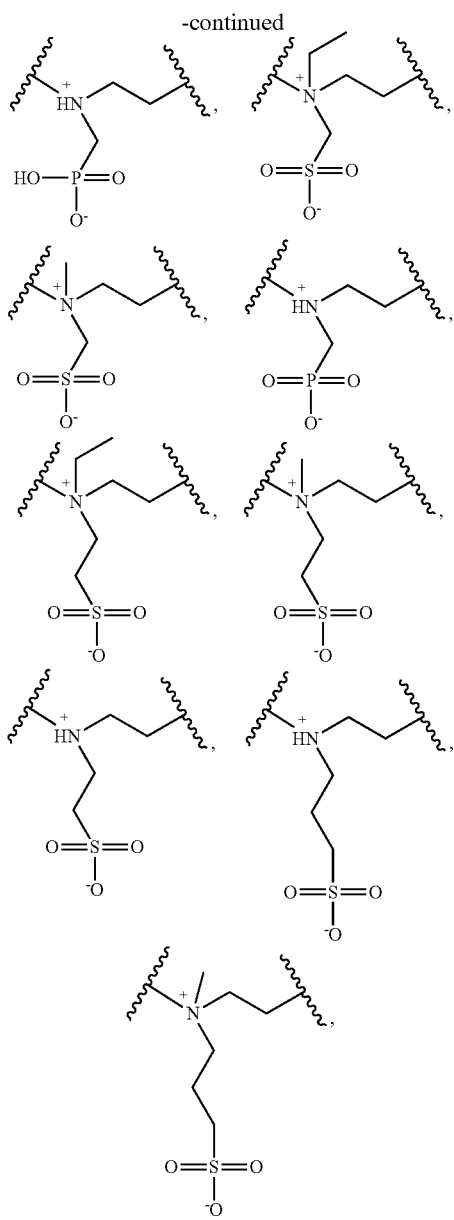

and any combination thereof.

Aspect 17. The biocompatible polymer of any one of the preceding aspects, further comprising one or more secondary repeating units.

Aspect 18. The biocompatible polymer according to aspect 17, wherein the one or more secondary repeating units have a structure according to Formula (III):

(III)

wherein $R^{11}$ is H, —$CH_3$, —$(CH_2)_nCH_3$, —$(CH_2CH_2O)_n$ $CH_3$, —$(CH_2CH_2O)_n(CH_2)_mCH_3$, —$(CH_2CH_2O)_n$ $(CH_2)_mOH$, —$((CH_2)_nO)_m((CH_2)_pO)_q(CH_2)_rOH$, —$(CH_2CH_2O)_nH$, —$(CH_2)_nOH$, —$(CH_2)_nO(CH_2)_m$ OH, —$(CH_2CH_2OCH_2CH_2)_nOH$, —$(CH_2CH_2O)_n$ $CH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_p$ OH, —$((CH_2)_{1-8}C(O)O)_n(CH_2CH_2)_m(OC(O)(CH_2)_{1-8})_p$OH, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH$ $(CH_2)_mOH$, $C_{1-n}$ alkenyl, $C_{1-n}$ alkynyl, $C_{6-10}$ aryl, pentafluorophenyl, or succinimidyl.

Aspect 19. The biocompatible polymer of aspect 17 or 18, wherein the one or more secondary repeating units are derived from lactic acid, caproic acid, glycolic acid, or any combination thereof.

Aspect 20. The biocompatible polymer of aspect 1, wherein the polymer is of Formula (IV):

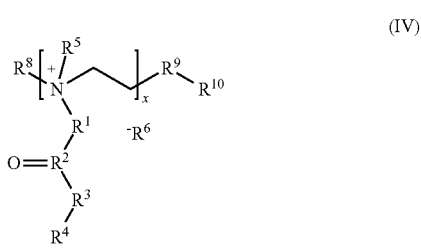

(IV)

wherein $R^3$ is —$CH_3$, —$CH_2CH$=$CH_2$, —$(CH_2)_n$ $CH$=$CH_2$, —$(CH_2)_nCH$=$CH_2(CH_2)_tCH_3$, —$CH_2C$≡$CH$, —$(CH_2)_nC$≡$CH$, —$(CH_2)_nC$≡$C(CH_2)_t$ $CH_3$, —$(CH_2)_nCH_3$, —$(CH_2)_nCH_2N_3$, —$(CH_2)_nNH_2$, —$(CH_2)_nCH_2SH$, —$(CH_2CH_2O)_nCH_3$, —$(CH_2CH_2O)_n(CH_2)_mCH_3$, —$(CH_2CH_2O)_n(CH_2)_m$ $N_3$, —$(CH_2CH_2O)_n(CH_2)_mSH$, —$(CH_2CH_2O)_n(CH_2)_m$ OH, —$((CH_2)_nO)_m((CH_2)_pO)_q(CH_2)_rOH$, —$(CH_2CH_2O)_nH$, —$(CH_2)_nOH$, —$(CH_2)_nO(CH_2)_m$ OH, —$(CH_2CH_2OCH_2CH_2)_nOH$, —$(CH_2CH_2O)_n$ $CH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_p$ OH, —$((CH_2)_{1-8}C(O)O)_n(CH_2CH_2)_m(OC(O)$ $(CH_2)_{1-8})_p$ OH, —$(CH_2C(O)O)_n(CH_2CH_2)_m(OC(O)$ $CH_2)_pOH$, —$(CH(CH_3)C(O)O)_n(CH_2CH_2)_m(OC(O)$ $CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH$ $(CH_2)_mOH$, $C_{1-n}$ alkenyl, $C_{1-n}$ alkynyl, $C_{6-10}$ aryl, or a compound containing acyl halide, alcohol, aldehyde, amide, amine, azo, Anhydride, azide, hydrazide, toluene derivative, biotin, disulfide, carbonate, carboxylic acid, cyanate, haloalkane, ether, ester, hydroperoxide, hydrazone, isocyanide, imine, isocyanate, ketone, nitrate, nitrile, nitrite, nitro, nitroso, peroxide, benzyl, phosphodiester, vinylsulfone, thiol, hydroxyl, imidoester, pyridyldithiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester;

$R^9$ is O, NH, S, Se, $CH_2$, or —N=N—, $R^{10}$ is —H, —N, —$CH_3$, —$CH_2CH$=$CH_2$, —$(CH_2)_n$ $CH$=$CH_2$, —$(CH_2)_nCH$=$CH_2(CH_2)_tCH_3$, —$CH_2C$≡$CH$, —$(CH_2)_nC$≡$CH$, —$(CH_2)_nC$≡$C(CH_2)_t$ $CH_3$, —$(CH_2)_nCH_3$, —$(CH_2)_nCH_2N_3$, —$(CH_2CH_2O)_n$ $CH_3$, —$(CH_2CH_2O)_n(CH_2)_mCH_3$, —

—(CH$_2$CH$_2$O)$_n$(CH$_2$)$_m$N$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —(CH$_2$CH$_2$O)$_n$CH$_2$CH$_2$OH, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_p$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, —(CH$_2$)$_n$C(O)NH(CH$_2$)$_m$OH, vinyl sulfone, succinimidyl ester, pentafluorophenyl ester, —SH, —(CH$_2$)$_n$NH$_2$, —(CH$_2$)$_n$COOH, —(CH$_2$)$_n$SH, —(CH$_2$)$_n$NH(CH$_2$)$_m$CH$_3$, —(CH$_2$)$_n$NHCH$_3$, —(CH$_2$CH$_2$O)$_n$(CH$_2$)$_m$NH$_2$, —(CH$_2$CH$_2$O)$_n$(CH$_2$)$_m$SH, —(CH$_2$CH$_2$O)$_n$(CH$_2$)$_m$COOH, C$_{1-n}$ alkenyl, C$_{1-n}$ alkynyl, C$_{6-10}$ aryl, C$_{1-n}$ alkylene-SH,

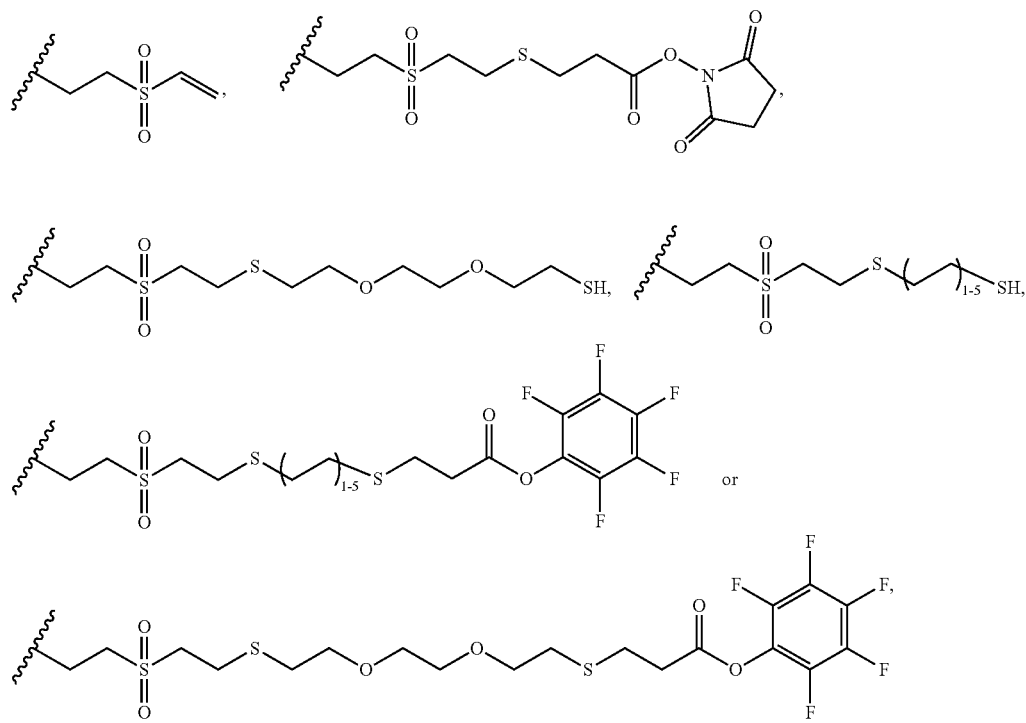

or a compound containing acyl halide, alcohol, aldehyde, amide, amine, azo, Anhydride, azide, hydrazide, toluene derivative, biotin, disulfide, carbonate, carboxylic acid, cyanate, haloalkane, ether, ester, hydroperoxide, hydrazone, isocyanide, imine, isocyanate, ketone, nitrate, nitrile, nitrite, nitro, nitroso, peroxide, benzyl, phosphodiester, vinylsulfone, thiol, hydroxyl, imidoester, pyridyldithiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester; and, x is 1 to 10,000.

Aspect 21. The biocompatible polymer of aspect 20, wherein the polymer is hydrolyzed.

Aspect 22. The biocompatible polymer of aspect 21, wherein the hydrolyzed polymer has a structure of Formula (V):

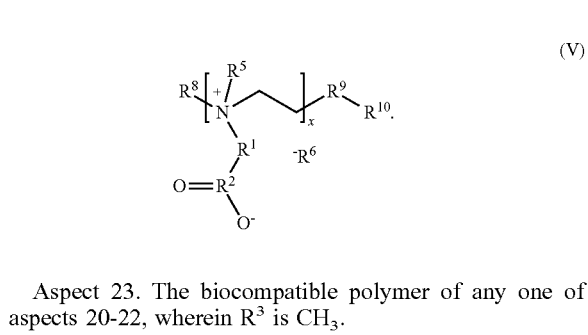

Aspect 23. The biocompatible polymer of any one of aspects 20-22, wherein R$^3$ is CH$_3$.

Aspect 24. The biocompatible polymer of any one of aspects 20-23, wherein R$^9$ is O.

Aspect 25. The biocompatible polymer of any one of aspects 20-24, wherein R$^{10}$ is H.

Aspect 26. The biocompatible polymer of any one of aspects 20-24, wherein R$^{10}$ has a structure of:

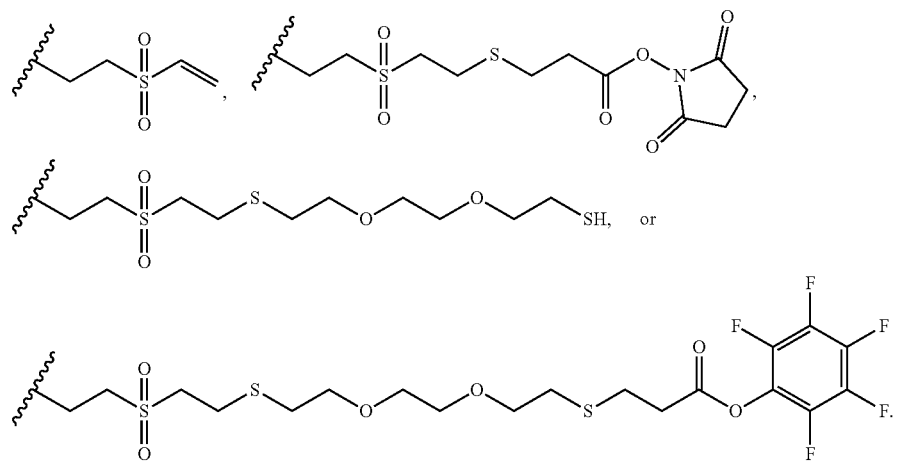

Aspect 27. The biocompatible polymer of any one of the preceding aspects, wherein the polymer comprises at least a first and a second zwitterionic precursor repeating unit of Formula (I), and one or more of $R^1$, $R^2$, $R^3$, $R^4$, $R^5$, $R^6$, and $R^7$ of the first zwitterionic precursor repeating unit of Formula (I) is different than one or more of $R^1$, $R^2$, $R^3$, $R^4$, $R^5$, $R^6$, and $R^7$ of the second zwitterionic precursor repeating unit of formula (I).

Aspect 28. The biocompatible polymer of any one of the preceding aspects, wherein the polymer comprises at least a first and a second zwitterionic repeating units of Formula (II), and one or more of $R^1$, $R^2$, $R^3$, $R^4$, $R^5$, $R^6$, and $R^7$ of the first zwitterionic repeating unit of Formula (II) is different than one or more of $R^1$, $R^2$, $R^3$, $R^4$, $R^5$, $R^6$, and $R^7$ of the second zwitterionic repeating unit of Formula (II).

Aspect 29. The biocompatible polymer of aspect 1, wherein the polymer has a structure of:

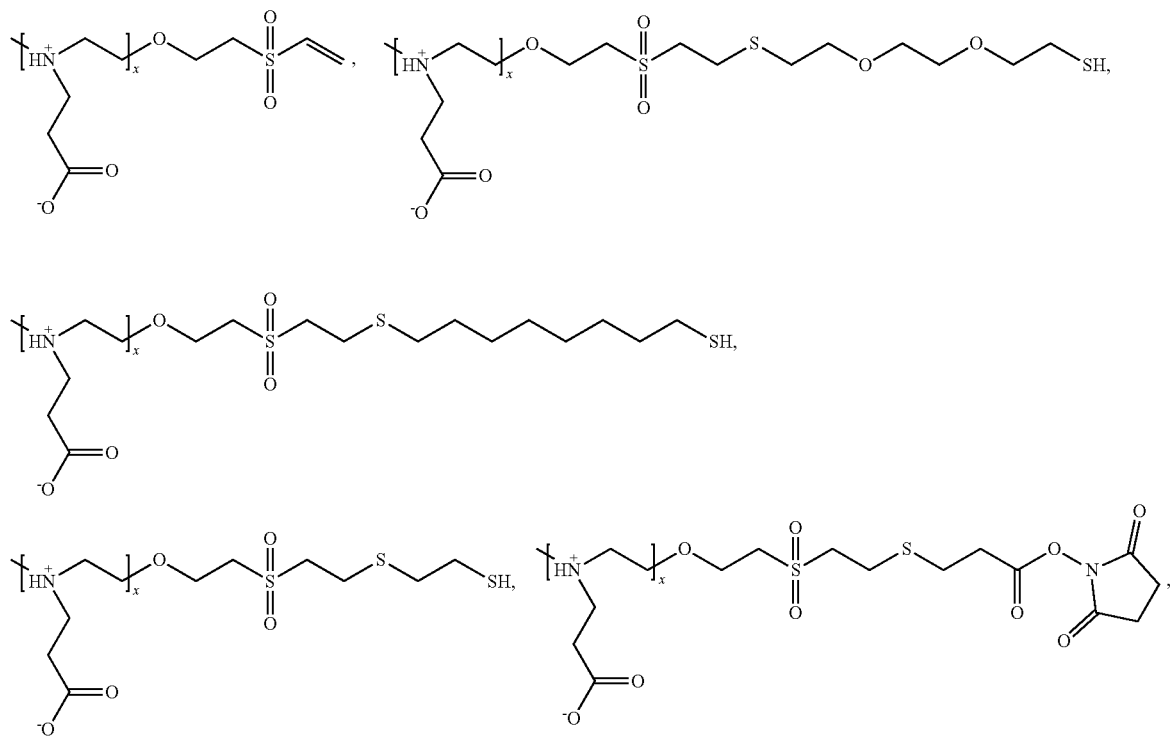

-continued

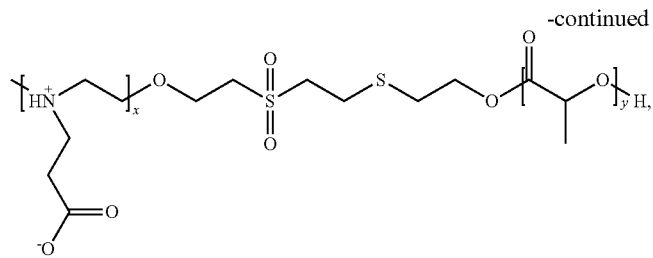

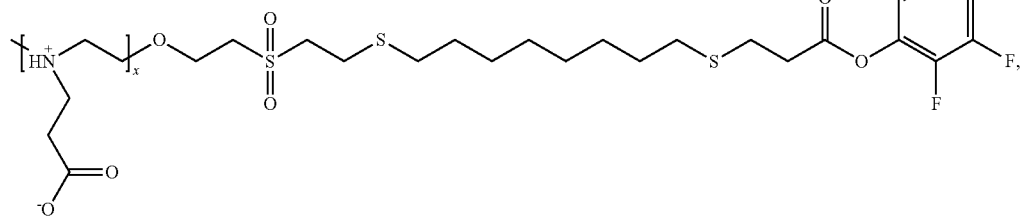

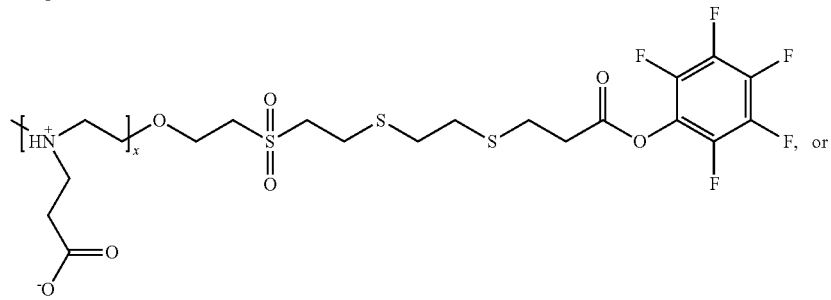

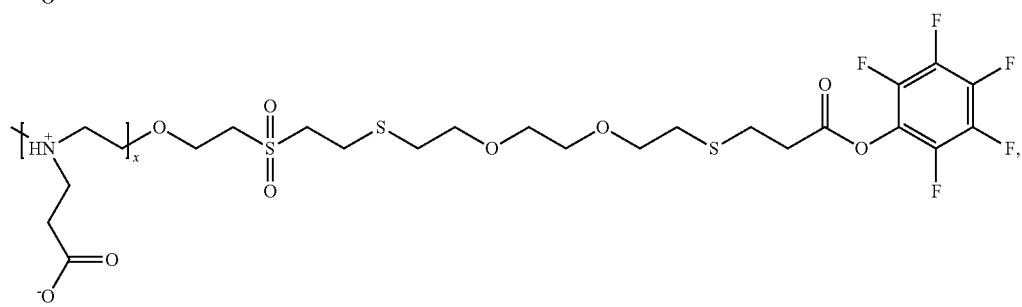

wherein y is 1 to 10,000.

Aspect 30. The biocompatible polymer of any one of the preceding aspects, wherein the polymer is conjugated to a peptide, a protein, a monosaccharide, a disaccharide, an oligo/polysaccharide, a lipid, a nucleic acid, a polymer, a targeting ligand molecule, a prodrug, a small molecule drug, or any combination thereof.

Aspect 31. The biocompatible polymer of aspect 30, wherein the polymer is conjugated to the peptide or protein via the thiol group of a cysteine residue, the amine group of a lysine residue, the imidazole group of a histidine residue, the phenol group of a tyrosine residue, the carboxylate group of an aspartic acid or a glutamate, the amine group at the N-terminal of a peptide or protein, the carboxylate group at the C-terminal of a peptide or protein, or a combination thereof.

Aspect 32. The biocompatible polymer of aspect 30 or 31, wherein the peptide or protein is selected from the group consisting of matrix metalloproteinase (MMP), an antibody, an interferon, an interleukin, insulin, a glucogon-like peptide, an enzyme, a cationic peptide, an anionic peptide, a lipoprotein, a glycoprotein, albumin, Fv, an antigen, an antigen-binding fragment (Fab), a single-chain variable fragment, an enzyme cutting sequence, LHRH peptide, RGD peptide, and any combination thereof.

Aspect 33. The biocompatible polymer of any one of aspects 30-32, wherein the monosaccharide is selected from the group consisting of glucose, fructose, galactose, mannose, ribose, deoxyribose, galactosamine, glucosamine, sialic acid, N-acetylglucosamine, N-acetylgalactosamine, sulfoquinovose, ascorbic acid, mannitol, glucuronic acid, α-D-glucopyranose, β-D-glucopyranose, psicose, mannosamine, N-acetylmannosamine, allose, altrose, gulose, idose, talose, sorbose, tagatose, and any combination thereof.

Aspect 34. The biocompatible polymer of any one of aspects 30-33, wherein the disaccharide is selected from the group consisting of sucrose, lactulose, lactose, maltose, cellobiose, chitobiose, kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, xylobiose, and any combination thereof.

Aspect 35. The biocompatible polymer of any one of aspects 30-34, wherein the oligo/polysaccharide is selected from the group consisting of starch, cellulose, dextran, chitin, glycosaminoglycans, mannan, dextrin, agar, agarose, alginic acid, alguronic acid, amylose, alpha glucan, amylopectin, beta-glucan, callose, carrageenan, cellodextrin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin, and any combination thereof.

Aspect 36. The biocompatible polymer of any one of aspects 30-35, wherein the lipid is selected from the group consisting of cholesterol, phospholipids, sphingolipids, N-palmitoylglycine, fatty acid, coenzyme Q6, phosphatidylethanolamine, prostaglandin, monoglucosyl diacylglycerol, glycerides, eicosanoids, PAHSA, phosphatidylcholine, phosphatidylglycerol, phosphatidylserine, sphingomyelin, ganglioside, lipopolysaccharide, phosphatidylinositol and any derivative of the foregoing.

Aspect 37. The biocompatible polymer of any one of aspects 30-36, wherein the nucleic acid is selected from the group consisting of deoxyribosenucleic acids (DNA), ribonucleicacids (RNA), aptamers, DNA/RNA hybrid, any derivatives thereof, and any combinations thereof.

Aspect 38. The biocompatible polymer of any one of aspects 30-37, wherein the small molecule drug is selected from the group consisting of folate, abiraterone acetate, brentuximab vedotin, trastuzumab emtansine, afatinib, everolimus, imiquimod, pemetrexed disodium, pemetrexed, palonosetron, chlorambucil, nelarabine, axitinib, belinostat, bleomycin, bortezomib, cabozantinib-S-malate, camptothecin, capecitabine, ceritinib, daunorubicin, crizotinib, dabrafenib, dasatinib, degarelix, docetaxel, doxorubicin, epirubicin, eribulin, etoposide, raloxifene, fulvestrant, methotrexate, pralatrexate, eribulin mesylate, topotecan, ibritumomab tiuxetan, ibrutinib, irinotecan, ixabepilone, cabazitaxel, ado-trastuzumab emtansine, lenalidomide, leuprolide acetate, vincristine, mitomycin C, mitoxantrone, nelarabine, paclitaxel, prednisone, eltrombopag olamine), raloxifene hydrochloride, lenalidomide, omacetaxine mepesuccinate), bexarotene, temsirolimus, bendamustine hydrochloride, vinblastine sulfate, vinblastine sulfate, vincristine sulfate, vinorelbine tartrate, vorinostat, capecitabine, ipilimumab, and goserelin acetate.

Aspect 39. The biocompatible polymer of any one of aspects 30-38, wherein the polymer is conjugated to folate, peptide, galactose, a liver-affinity polysaccharide, a liver-affinity monosaccharide, an antibody, Fab, Fv, LHRH peptide, RGD peptide, ow-density lipoprotein, recombinant human TNF-receptor fusion protein, interferon alfa, interferon beta, interferon gamma, interleukin 1-36, plecanatide, phenylalanine ammonia-lyase, antihemophilic factor VIII, interferon Beta-1a, naloxol, uricase, monoclonal antibody, erythropoietin, granulocyte colony-stimulating factor, growth hormone receptor antagonist, L-asparaginase, adenosine deaminase, granulocyte-colony stimulating factor, arginase, anti-VEGF aptamer, tumor necrosis factor alpha inhibitor, urate oxidase, erythropoietin receptor activators, cell adhesion peptides, RGD peptides, CRGDS, cyclic RGD peptide, Vascular endothelial growth factor (VEGF), Platelet-derived growth factor (PDGF), epidermal growth factor, or any combination thereof.

Aspect 40. The biocompatible polymer of any one of the preceding aspects, wherein the polymer has a solubility in water at 20-50° C. in a range of about 1 pg/mL to about 500 mg/mL.

Aspect 41. A nanoparticle comprising:
the biocompatible polymer according to any one of aspects 1-40 and a drug or a prodrug,
wherein the drug is selected from the group consisting of a peptide, a protein, a nucleic acid, a small molecule drug, a prodrug, and any combination thereof.

Aspect 42. The nanoparticle of aspect 41, wherein the nanoparticle comprises:
a core comprising the drug or the prodrug, and
a shell comprising the biocompatible polymer.

Aspect 43. The nanoparticle of aspect 41 or 42, wherein the biocompatible polymer is conjugated to the drug.

Aspect 44. The nanoparticle of aspect 41 or 42, further comprising a drug carrier, wherein the drug is associated with the drug carrier, and the biocompatible polymer is conjugated to the drug carrier.

Aspect 45. The nanoparticle of aspect 44, wherein the drug carrier comprises a monosaccharide, a disaccharide, an oligo/polysaccharide, a peptide, a protein, a lipid, a dendrimer, a polymer, an organic nanoparticle, an inorganic nanoparticle, or any combination thereof.

Aspect 46. The nanoparticle of aspect 44 or 45, wherein the drug carrier is a liposome.

Aspect 47. The nanoparticle of any one of aspects 41-46, wherein the nanoparticle has a blood half-life of about 10 minutes to about 4 weeks.

Aspect 48. A method comprising:
(i) reacting a polyethyleneimine having a structure of:

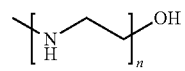

with an α,β-unsaturated ester having a structure of

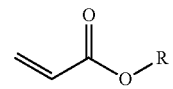

to form an N-alkylated polyethyleneimine having a structure of

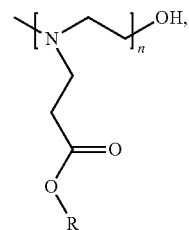

wherein n is from 1 to 10,000 and R is H, —$CH_3$, —$(CH_2)_nCH_3$, —$(CH_2CH_2O)_nCH_3$, —$(CH_2CH_2O)_n(CH_2)_mCH_3$, —$(CH_2CH_2O)_n(CH_2)_mOH$, —$((CH_2)_nO)_m$ $((CH_2)_pO)_q(CH_2)_rOH$, —$(CH_2CH_2O)_nH$, —$(CH_2)_nOH$, —$(CH_2)_nO(CH_2)_mOH$, —(CH$_2$CH$_2$OCH$_2$CH$_2$)$_n$OH, —(CH$_2$CH$_2$O)$_n$CH$_2$CH$_2$OH, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)$_n$(CH$_2$CH$_2$)$_m$(OC(O)(CH$_2$)$_{1-8}$)$_p$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, —(CH$_2$)$_n$C(O)NH(CH$_2$)$_m$OH, C$_{1-n}$ alkenyl, C$_{1-n}$ alkynyl, C$_{6-10}$ aryl, pentafluorophenyl ester or succinimidyl;

(ii) hydrolyzing the N-alkylated polyethyleneimine to provide a zwitterionic N-alkylated polyethyleneimine.

(iii) reacting the zwitterionic N-alkylated polyethyleneimine with a compound having a functional group capable of conjugating to a peptide, a protein, a monosaccharide, a disaccharide, an oligo/polysaccharide, a lipid, a nucleic acid, a polymer, a targeting ligand molecule, a prodrug, a small molecule drug, or any combination thereof to form a biocompatible zwitterionic polymer.

Aspect 49. The method of aspect 48, wherein step (iii) occurs in the presence of a base.

Aspect 50. The method of aspect 48 or 49, wherein the functional group capable of conjugating is selected from the group consisting of acyl halide, alcohol, aldehyde, amide, amine, azo, Anhydride, azide, hydrazide, toluene derivative, biotin, disulfide, carbonate, carboxylic acid, cyanate, haloalkane, ether, ester, hydroperoxide, hydrazone, isocyanide, imine, isocyanate, ketone, nitrate, nitrile, nitrite, nitro, nitroso, peroxide, benzyl, phosphodiester, vinylsulfone, thiol, hydroxyl, imidoester, pyridyldithiol, phophonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester, any derivative of the any foregoing, and any combination of any of the foregoing.

Aspect 51. The method of any one of aspects 48-50, wherein the compound having a functional group capable of conjugating is divinyl sulfone.

Aspect 52. The method of aspect 51, wherein step (iii) further comprises reacting the zwitterionic N-alkylated polyethyleneimine with a second compound having a structure selected from the group consisting of

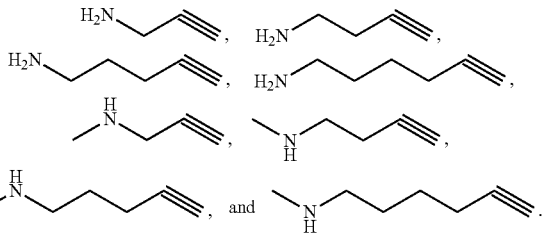

and a third compound having a structure selected from

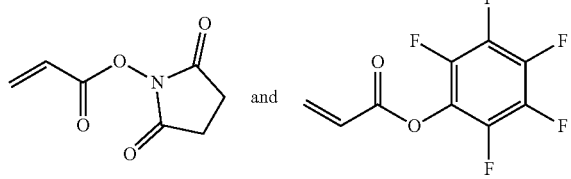

to form the biocompatible zwitterionic polymer.

Aspect 53. The method of aspect 51, wherein step (iii) further comprises reacting the zwitterionic N-alkylated polyethyleneimine with a second compound having a structure selected from the group consisting of

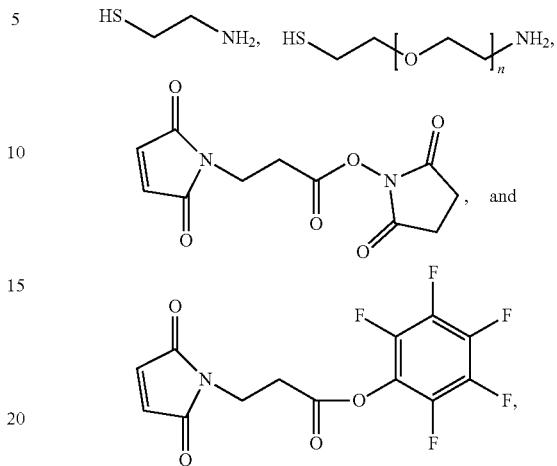

and a third compound having a structure of

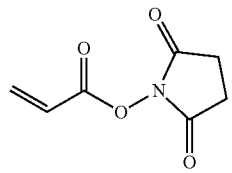

to form the biocompatible zwitterionic polymer.

Aspect 54. The method of aspect 51, wherein step (iii) further comprises reacting the zwitterionic N-alkylated polyethyleneimine with a second compound having a structure of

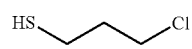

and NaN$_3$.

Aspect 55. The method of aspect 51, wherein step (iii) further comprises reacting the zwitterionic N-alkylated polyethyleneimine with a second compound having a structure selected from the group consisting of Aspect 56. The method of any one of aspects 48-55, further comprising conjugating a peptide, a protein, a monosaccharide, a disaccharide, an oligo/polysaccharide, a lipid, a nucleic acid, a target polymer, a small molecule drug, or any combination thereof to the zwitterionic biocompatible polymer.

Aspect 57. A system for nucleic acid delivery comprising:
a cationic core comprising a cationic compound and nucleic acid; and,
a polysaccharide-anionic peptide conjugate comprising an anionic peptide physically bound to a polysaccharide, and the biocompatible polymer of any one of aspects 1-40 is associated with the cationic core or the polysaccharide-anionic peptide conjugate.

Aspect 58. The system of aspect 57, wherein the biocompatible polymer is associated with the cationic core by bonding of the biocompatible polymer to the cationic compound.

Aspect 59. The system of aspect 58, wherein the cationic compound is a cationic polymer, and the biocompatible polymer is bound to the cationic polymer as a side chain.

Aspect 60. The system of aspect 57, wherein the biocompatible polymer is associated with the polysaccharide-anionic peptide conjugate by bonding of the biocompatible polymer to the polysaccharide as a side chain, incorporation of the biocompatible polymer as part of the backbone of the polysaccharide, or bonding of the biocompatible polymer to the anionic peptide.

Aspects—Set Two

Aspect 1. A biocompatible zwitterionic polyethyleneimine, polyaziridine, or polyoxazoline derivative comprising one or more zwitterionic moieties, one or more zwitterionic precursor moieties, or a combination thereof.

Aspect 2. The biocompatible zwitterionic polyethyleneimine, polyaziridine, or polyoxazoline derivative of aspect 1, wherein the zwitterionic precursor moieties can be converted to zwitterionic moieties by hydrolysis, chemical agents, heat, radiation, electricity, oxidation, reduction, acid, or base.

Aspect 3. The biocompatible polyethyleneimine, polyaziridine, or polyoxazoline derivative of aspect 2, wherein the zwitterionic moieties are selected from carboxybetaine, sulfobetaine, and phosphobetaine.

Aspect 4. The biocompatible polyethyleneimine, polyaziridine, or polyoxazoline derivative of aspect 3, wherein the zwitterionic precursor moieties are converted to zwitterionic moieties by hydrolysis.

Aspect 5. The biocompatible polyethyleneimine, polyaziridine, or polyoxazoline derivative of aspect 1, comprising repeating units of formula:

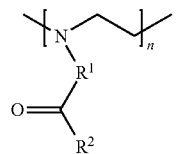

wherein $R^1$ is —$CH_2$—, —$CH_2CH_2$—, —$CH_2CH_2CH_2$—, —$(CH_2)_m$—, —$CH_2CH_2OCH_2CH_2$—, —$(CH_2)_nO(CH_2)_o$—, —$(CH_2CH_2OCH_2CH_2)_p$—, or —$CH_2CH_2(OCH_2CH_2)$—;

$R^2$ is a proton or molecule linked to the polymer by ester bond, amide bond, or anhydride bond selected from polyethylene glycol, oligoethylene glycol, methanol, ethanol, cell adhesion molecules, RGD peptide, folate, galactose, galactose derivatives, and cholesterol; and, m, n, o, p and v are independently from 1 to 1000.

Aspect 6. The biocompatible polyethyleneimine, polyaziridine, or polyoxazoline derivative of aspect 1, comprising repeating units of formula:

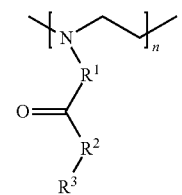

wherein $R^1$ is —$CH_2$—, —$CH_2CH_2$—, —$CH_2CH_2CH_2$—, —$(CH_2)_m$—, —$CH_2CH_2OCH_2CH_2$—, —$(CH_2)_nO(CH_2)_o$—, —$(CH_2CH_2OCH_2CH_2)_p$—, or —$CH_2CH_2(OCH_2CH_2)$—;

$R^2$ is O, NH, or S;

$R^3$ is H, $C_{1-q}$ alkyl, at targeting ligand, a peptide, a monosaccharide, an oligosaccharide, a polysaccharide, or a glycoside; and, m, n, o, p, q and v are independently from 1 to about 1000.

Aspect 7. The biocompatible polyethyleneimine, polyazridine, or polyoxazoline derivative of aspect 1, comprising repeating units of formula:

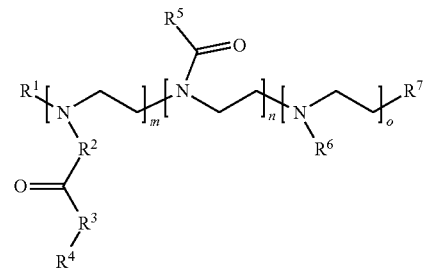

wherein $R^1$ is $C_{1-4}$ alkyl, a lipid, an organic acid, an aromatic compound, a polyester, a polyether, a targeting ligand, a peptide, a protein, a polymer, a monosaccharide, an oligosaccharide, a polysaccharide, a glycoside, an alkane, an alkene containing compound, an alkyne containing compound, a thiol containing compound, a disulfide containing compound, an ester containing compound, a prodrug, a click-chemistry group, an amine containing compound, or a functional group for the conjugation of other compound;

$R^2$ is —$CH_2$—, —$CH_2CH_2$—, —$CH_2CH_2CH_2$—, —$(CH_2)_j$—, —$CH_2CH_2OCH_2CH_2$—, —$CH_2CH_2(OCH_2CH_2)_v$—, —$(CH_2)_kO(CH_2)_i$—, —$(CH_2CH_2OCH_2CH_2)_p$—;

$R^3$ is O, NH, or S;

$R^4$ is $C_{1-q}$ alkyl, at targeting ligand, a peptide, a monosaccharide, an oligosaccharide, a polysaccharide, or a glycoside;

$R^5$ is $C_{1-r}$ alkyl;

$R^6$ is H, $C_{1-s}$ alkyl, an alkane, an alkene, or an alkyne;

$R^7$ is —OH, —$CH_3$, —$CH_2OH$, —$CH_2CH_2OH$, —$(CH_2)_u$ $CH_3$, a lipid, an organic acid, an aromatic compound, a polyester, a polyether, a targeting ligand, a peptide, a protein, a degradable polymer, a monosaccharide, an oligosaccharide, a polysaccharide, a glycoside, an alkane, an alkene containing compound, an alkyne containing compound, an ester containing compound, a prodrug, a click-chemistry group, a thiol containing compound, a disulfide containing compound, an amine containing compound, or a functional group for the conjugation of other compound;

m is from 1 to about 10,000;

n and o are independently integers from 0 to about 10,000; and.

i, j, k, l, p, q, r, s, t, u, and v are independently integers from 1 to about 100.

Aspect 8. The biocompatible polyethyleneimine, polyaziridine, or polyoxazoline derivative of aspect 1, comprising repeating units of formula:

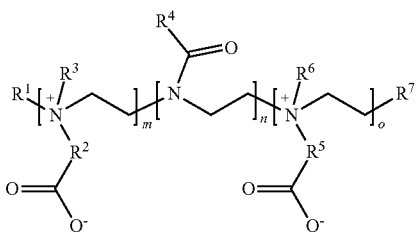

wherein $R^1$ and $R^7$ are independently —OH, —NH$_2$, —SH, —C$_{1-i}$ alkyl, a lipid, an organic acid, a protein, a degradable polymer, an aromatic compound, a polyester, a polyether, a targeting ligand, a peptide, a monosaccharide, an oligosaccharide, a polysaccharide, a glycoside, an alkane, an alkene containing compound, an alkyne containing compound, a thiol containing compound, a disulfide containing compound, an ester containing group, a prodrug, a click-chemistry group, an amine containing compound, or a functional group for the conjugation of another compound;

$R^2$ is —CH$_2$—, —CH$_2$CH$_2$—, —CH$_2$CH$_2$CH$_2$—, —(CH$_2$)$_j$—, —CH$_2$CH$_2$OCH$_2$CH$_2$—, —CH$_2$CH$_2$(OCH$_2$CH$_2$)$_w$—, —(CH$_2$)$_k$O(CH$_2$)$_l$—;

$R^3$ is H, C$_{1-p}$ alkyl, an alkane, an alkene, an alkyne, a targeting ligand, a peptide, a monosaccharide, an oligosaccharide, a polysaccharide, or a glycoside;

$R^4$ is —C$_{1-q}$ alkyl, an alkane, an alkene, an alkyne, or an aromatic containing group;

$R^5$ is —CH$_2$—, —CH$_2$CH$_2$—, —CH$_2$CH$_2$CH$_2$—, —(CH$_2$)$_r$—, —CH$_2$CH$_2$OCH$_2$CH$_2$—, —CH$_2$CH$_2$(OCH$_2$CH$_2$)$_s$—, —(CH$_2$)$_t$O(CH$_2$)$_u$—;

$R^6$ is —H, —C$_{1-v}$ alkyl, an alkane, an alkene, an alkyne, a targeting ligand, a peptide, a monosaccharide, an oligosaccharide, a polysaccharide, or a glycoside;

m, n, and o are independently from 0 to about 10,000;

i, j, k, l, p, q, r, s, t, u, v, and w are independently integers from 1 to about 100.

Aspect 9. The biocompatible polyethyleneimine, polyaziridine, or polyoxazoline derivative of aspect 1, comprising repeating units of formula:

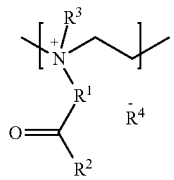

wherein $R^1$ is —CH$_2$—, —CH$_2$CH$_2$—, —CH$_2$CH$_2$CH$_2$—, —(CH$_2$)$_j$—, —CH$_2$CH$_2$OCH$_2$CH$_2$—, —CH$_2$CH$_2$(OCH$_2$CH$_2$)$_v$—, —(CH$_2$)$_n$O(CH$_2$)$_o$—, —(CH$_2$CH$_2$OCH$_2$CH$_2$)$_p$;

$R^2$ is H, C$_{1-s}$ alkyl, an alkane, an alkene, an alkyne, —(CH$_2$)$_t$OH, —CH$_2$CH$_2$OH, —(CH$_2$)$_u$CH$_3$, —(CH$_2$CH$_2$O)$_w$CH$_3$, —(CH$_2$CH$_2$O)$_x$H, a lipid, an organic acid, an aromatic compound, a polyester, a polyether, a targeting ligand, a peptide, a monosaccharide, an oligosaccharide, a polysaccharide, a glycoside, an alkane, an alkene, an alkyne, a thiol, an amine, or a functional group for the conjugation of other compound(s);

$R^4$ is an inorganic or organic anionic counter ion; and m, n, o, p, v, s, t, u, w, x are independently from 1 to about 10,000;

Aspect 10. The biocompatible polyethyleneimine, polyaziridine, or polyoxazoline derivative of aspect 1, comprising repeating units of formula:

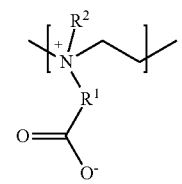

wherein $R^1$ is —CH$_2$—, —CH$_2$CH$_2$—, —CH$_2$CH$_2$CH$_2$—, —(CH$_2$)$_m$—, —CH$_2$CH$_2$OCH$_2$CH$_2$—, —CH$_2$CH$_2$(OCH$_2$CH$_2$)$_v$—, —(CH$_2$)$_n$O(CH$_2$)$_o$—, —(CH$_2$CH$_2$OCH$_2$CH$_2$)$_p$;

$R^2$ is a molecule linked to the said polymer by ester bond, amide bond, or anhydride bond;

$R^3$ is H, C$_{1-s}$ alkyl, an alkane, an alkene, an alkyne, —(CH$_2$)$_t$OH, —CH$_2$CH$_2$OH, —(CH$_2$)$_u$CH$_3$, —(CH$_2$CH$_2$O)$_w$CH$_3$, —(CH$_2$CH$_2$O)$_x$H, a lipid, an organic acid, an aromatic compound, a polyester, a polyether, a targeting ligand, a peptide, a monosaccharide, an oligosaccharide, a polysaccharide, a glycoside, an alkane, an alkene, an alkyne, a thiol, an amine, or a functional group for the conjugation of other compound (s);

m, n, o, p, v, s, t, u, w, x are independently from 1 to about 10,000

Aspect 11. The biocompatible polyethyleneimine, polyaziridine, or polyoxazoline derivative of aspect 1, comprising repeating units of formula:

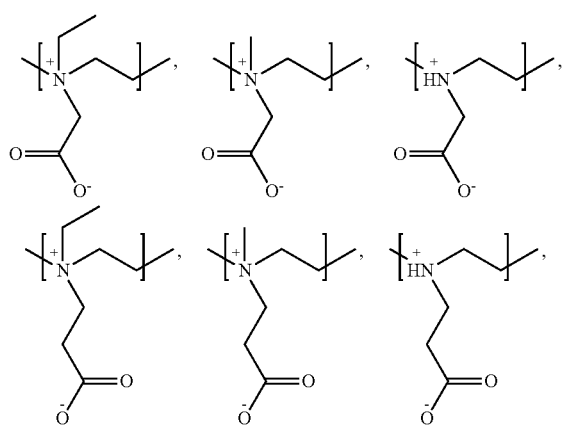

or a combination thereof.

Aspect 12. The biocompatible polyethyleneimine, polyaziridine, or polyoxazoline derivative of aspect 1 of formula:

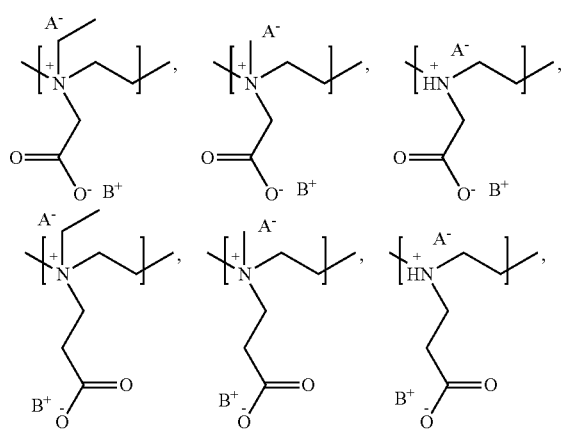

or a combination thereof, wherein A⁻ is an anion and B⁺ is a cation.

Aspect 13. The biocompatible polyethyleneimine, polyaziridine, or polyoxazoline derivative of aspect 1, comprising repeating units of formula:

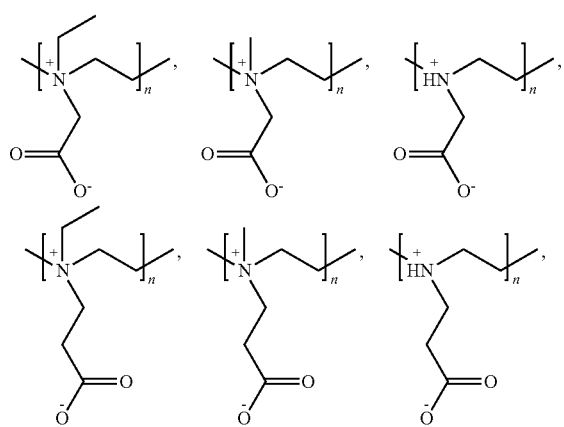

wherein n is from 1 to about 100,000.

Aspect 14. The biocompatible polyethyleneimine, polyaziridine, or polyoxazoline derivative of aspect 1 of formula:

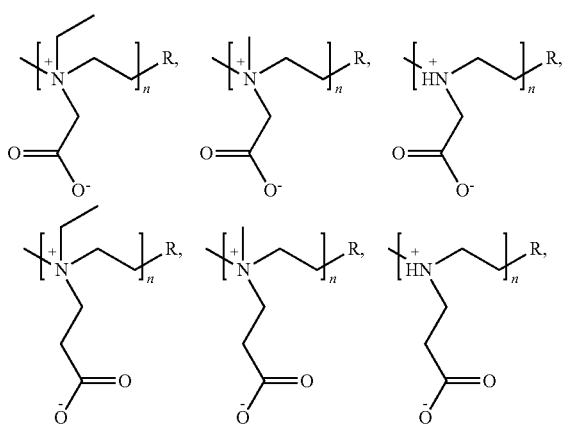

wherein R is a linker for conjugation to a protein and n is from 1 to about 100,000.

Aspect 15. The biocompatible polyethyleneimine, polyaziridine, or polyoxazoline derivative of aspect 1 of formula:

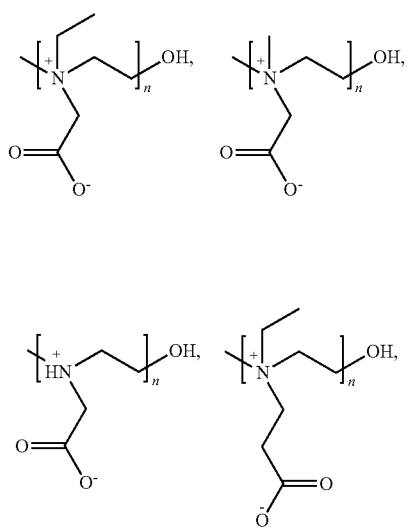

wherein n is from 1 to about 100,000.

Aspect 16. The biocompatible polyethyleneimine, polyaziridine, or polyoxazoline derivative of aspect 1 of formula:

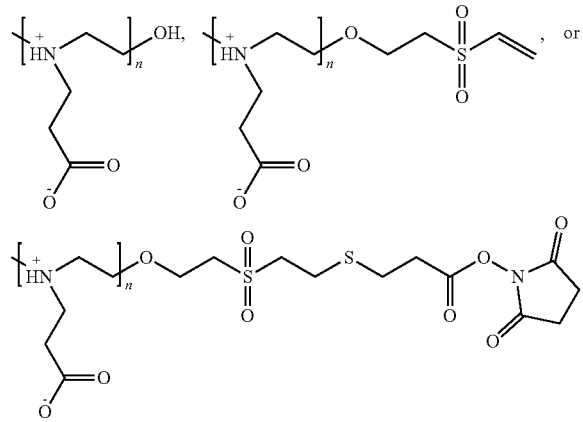

wherein n is from 1 to about 100,000.

Aspect 17. The biocompatible polyethyleneimine, polyaziridine, or polyoxazoline derivative of aspect 1 of formula:

63

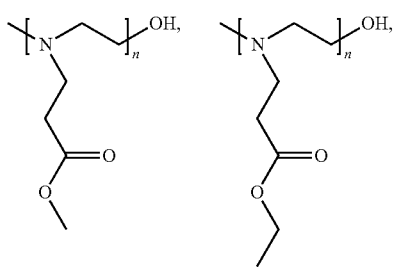

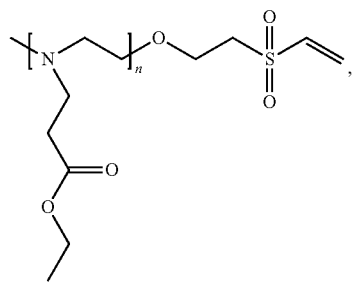

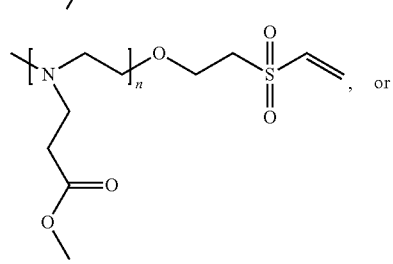, or

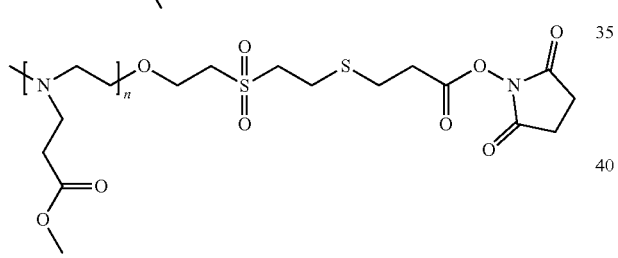

wherein n is from 1 to about 100,000.

Aspect 18. A polymer-protein conjugate comprising the biocompatible polyethyleneimine, polyaziridine, or polyoxazoline derivative of any one of claims 1-17.

Aspect 19. A method of preparing a zwitterionic polyethyleneimine of formula 1

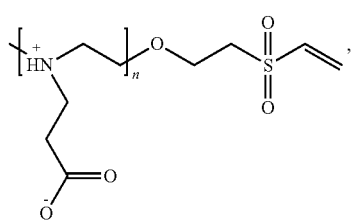 (1)

64 wherein n is from 1 to about 100,000, comprising (i) reacting polyethyleneimine 2

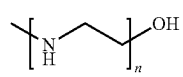 (2)

with α,β-unsaturated ester 3,

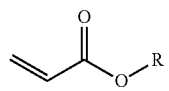 (3)

wherein R is —$CH_3$, —$CH_2CH_3$, or —$(OCH_2CH_2)_mCH_3$ to form N-alkylated polyethyleneimine 4

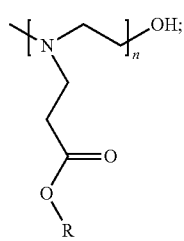 (4)

(ii) reacting N-alkylated polyethyleneimine 4 with sulfo-betaine 5

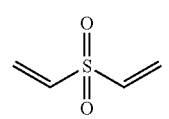 (5)

in the presence of base to form the polyethyleneimine comprising a zwitterionic precursor moiety 6

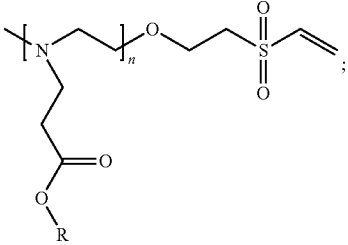 (6)

and (iii) hydrolyzing the polyethyleneimine comprising a zwitterionic precursor moiety 6 to form zwitterionic polyethyleneimine 7

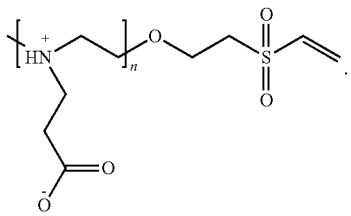

(7)

Aspects—Set Three

Aspect 1. A polysaccharide-anionic peptide conjugate for nucleic acid delivery comprising:
a polysaccharide polymer; and,
an anionic peptide bonded to the polysaccharide polymer as a side chain.

Aspect 2. The polysaccharide-anionic peptide conjugate of aspect 1, wherein the polysaccharide polymer comprises dextran, cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin, or any combination thereof.

Aspect 3. The polysaccharide-anionic peptide conjugate of aspect 1 or 2, wherein the polysaccharide polymer comprises dextran.

Aspect 4. The polysaccharide-anionic peptide conjugate of any one of the preceding aspects, wherein the polysaccharide polymer has a weight average molecular weight ranging from about 500 Da to about 1,000,000 Da.

Aspect 5. The polysaccharide-anionic peptide conjugate of any one of the preceding aspects, wherein the anionic peptide has a formula of $E_5H$, wherein E is glutamic acid and H is histidine.

Aspect 6. The polysaccharide-anionic peptide conjugate of any one the preceding aspects, wherein the anionic peptide is physically bonded to the polysaccharide polymer.

Aspect 7. The polysaccharide-anionic peptide conjugate of any one of the preceding aspects, further comprising a linker, wherein the linker molecule is directly bonded to the polysaccharide polymer at one end and directly bonded to the anionic peptide at an opposed end to thereby bond the anionic peptide to the polysaccharide polymer as a side chain.

Aspect 8. The polysaccharide-anionic peptide conjugate of aspect 7, wherein the linker molecule is physically bonded to the polysaccharide polymer via one or more hydroxyl or amine groups on the polysaccharide polymer.

Aspect 9. The polysaccharide-anionic peptide conjugate of aspect 8, wherein the linker molecule is physically bonded to the anionic peptide.

Aspect 10. The polysaccharide-anionic peptide conjugate of aspect 8 or 9, wherein the linker molecule comprises methacrylate, acrylate, methacrylamide, acrylamide, maleimide, haloacetyl, pyridyl disulfide, thiol, divinyl sulfone, or any combination thereof.

Aspect 11. The polysaccharide-anionic peptide conjugate of any one of the preceding aspects, further comprising a crosslinker compound bonded to the polysaccharide polymer as a side chain.

Aspect 12. The polysaccharide-anionic peptide conjugate of aspect 11, wherein the crosslinker compound comprises lipoic acid.

Aspect 13. The polysaccharide-anionic peptide conjugate of any one of the preceding aspects, further comprising a zwitterionic compound bonded to the polysaccharide polymer as a side chain.

Aspect 14. The polysaccharide-anionic peptide conjugate of aspect 13, wherein the zwitterionic compound comprises a carboxybetaine group, a sulfobetaine group, a phosphobetaine group, or any combination thereof.

Aspect 15. The polysaccharide-anionic peptide conjugate of any one of the preceding aspects, further comprising a reactive compound bonded to the polysaccharide polymer as a side chain, wherein the reactive compound is selected from the group consisting of an acrylate, a methacrylate, a methacrylamide, a maleimide, a haloacetyl, pyridyl disulfide, thiol, and any combination thereof.

Aspect 16. The polysaccharide-anionic peptide conjugate of any one of the preceding aspects, wherein the polysaccharide polymer comprises dextran and the anionic peptide has a formula of $E_5H$.

Aspect 17. The polysaccharide-anionic peptide conjugate of any one of the preceding aspects, wherein the polysaccharide polymer comprises dextran, the anionic peptide has the formula of $E_5H$ and is bonded to the polysaccharide polymer via a linker molecule comprising divinyl sulfone and a crosslinker compound comprising lipoic acid.

Aspect 18. A system for nucleic acid delivery comprising:
a cationic core comprising a cationic compound and nucleic acid; and
the polysaccharide-anionic peptide conjugate of any one of the preceding claims adsorbed the cationic core.

Aspect 19. The system of aspect 18, wherein the cationic core comprises a cationic polymer, a cationic peptide, or a combination thereof.

Aspect 20. The system of aspect 19, wherein the nucleic acid is physically bonded to the cationic polymer and/or cationic peptide.

Aspect 21. The system of aspect 19 or 20, wherein the cationic polymer is polyethyleneimine.

Aspect 22. The polysaccharide-anionic peptide conjugate of any one of aspects 18-21, wherein the nucleic acid comprises a ribonucleic acid, a deoxyribonucleic acid, or a combination thereof.

Aspect 23. The system of any aspect 22, wherein the nucleic acid is selected from the group consisting of plasmid DNA (pDNA), oligonucleotides, aptamers, DNAzymes, RNA aptamers, RNA decoys, antisense RNA, ribozymes, small interfering RNA (siRNA), microRNA (miRNA), short hairpin RNA, antagomirs, and any combination thereof.

Aspect 24. The system of any one of aspects 18-23, wherein the polysaccharide-anionic peptide conjugate forms a coating surrounding substantially an entirety of the cationic core.

Aspect 25. The system of any one of aspects 18-24, wherein the system further comprises a zwitterionic functional group or zwitterionic-containing polymer associated with the polysaccharide-anionic peptide conjugate.

Aspect 26. The system of aspect 25, wherein the zwitterionic functional group or zwitterionic-containing polymer is bonded to the polysaccharide polymer as a side chain, or the zwitterionic functional group is part of the backbone of the polysaccharide polymer, or zwitterionic functional group is bonded to the anionic peptide.

Aspect 27. The system of any one of aspects 18-26, wherein the system further comprises a zwitterionic functional group or zwitterionic-containing polymer associated with the cationic core.

Aspect 28. The system of aspect 27, wherein the cationic core comprises a cationic polymer or cationic peptide and the zwitterionic functional group or zwitterionic-containing polymer is part of the backbone of the cationic polymer, or is bonded to the cationic peptide, or wherein the cationic core comprises a cationic polymer and the zwitterionic functional group or zwitterionic-containing polymer is bonded to the cationic polymer as a side chain.

Aspect 29. The system of any one of aspects 25 to 28, wherein the zwitterionic-containing polymer comprises
a polymer backbone comprising one or more repeating units, wherein the one or more repeating units are each individually selected from zwitterionic precursor repeating unit of Formula (I), which has been hydrolyzed to convert the zwitterionic precursor repeating unit to a zwitterionic repeating unit, wherein Formula (I) is:

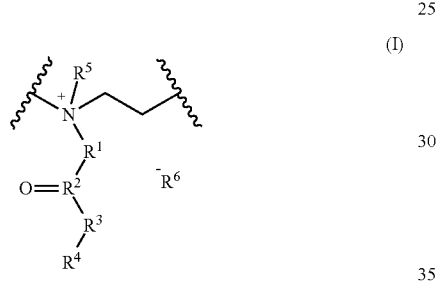

(I)

wherein $R^1$ is $-(CH_2)_n-$, $-(CH_2)_nO(CH_2)_m-$, $-(CH_2CH_2OCH_2CH_2)_n-$, $-(CH_2CH_2O)_n CH_2CH_2-$, $-(CH_2CH_2O)_n(CH_2)_m-$, $-(CH_2)_n(CH_2CH_2O)_m(CH_2)_p-$, $-((CH_2)_{1-8}C(O)O)_n(CH_2)_m-$, $-((CH_2)_{1-8}C(O)O)_n(CH_2CH_2)_m(OC(O)(CH_2)_{1-8})_p-$, $-((CH_2)_{1-8}C(O)O)_n(CH_2CH_2)_m(OC(O)(CH_2)_{1-8})_p-$, $-(CH_2C(O)O)_n(CH_2CH_2)_m(OC(O)CH_2)_p-$, $-(CH(CH_3)C(O)O)_n(CH_2CH_2)_m(OC(O)CH(CH_3))_p-$, $-(CH(CH_3)C(O)O)_n(CH_2CH_2)_m(OC(O)CH(CH_3))_p-$, $-((CH_2)_nOC(O)O)(CH_2CH_2)_m-$, $-(CH_2)_nNHC(O)(CH_2)_m-$, $-(CH_2)_nC(O)NH(CH_2)_m-$, $-(CH_2)_nS(O_2)(CH_2)_m-$, $-(CH_2)_nS(O_2)(CH_2)_m(CH_2)_t-$, $-(CH_2)_nO-$, $-(CH_2)_nO(CH_2)_m-$, $-(CH_2CH_2OCH_2CH_2)_nO-$, $-(CH_2CH_2O)_nCH_2CH_2O-$, $-(CH_2CH_2O)_n(CH_2)_mO-$, $-(CH_2)_n(CH_2CH_2O)_m(CH_2)_pO-$, $-((CH_2)_{1-8}C(O)O)_n(CH_2)_mO-$, $-((CH_2)_{1-8}C(O)O)_n(CH_2CH_2)_m(OC(O)(CH_2)_{1-8})_pO-$, $-((CH_2)_{1-8}C(O)O)_n(CH_2CH_2)_m(OC(O)(CH_2)_{1-8})_pO-$, $-(CH_2C(O)O)_n(CH_2CH_2)_m(OC(O)CH_2)_pO-$, $-(CH(CH_3)C(O)O)_n(CH_2CH_2)_m(OC(O)CH(CH_3))_pO-$, $-(CH(CH_3)C(O)O)_n(CH_2CH_2)_m(OC(O)CH(CH_3))_pO-$, $-((CH_2)_nOC(O)O)(CH_2CH_2)_mO-$, $-(CH_2)_nNHC(O)(CH_2)_mO-$, $-(CH_2)_nC(O)NH(CH_2)_mO-$, $-(CH_2)_nS(O_2)(CH_2)_mO-$, or $-(CH_2)_nS(O_2)(CH_2)_mO(CH_2)_tO-$;

$R^2$ is C, $P(OR^7)$, or $S(=O)$
$R^3$ is O or NH;
$R^4$, $R^5$ and $R^7$ are each independently H, $-CH_3$, $-(CH_2)_n CH_3$, $-(CH_2CH_2O)_nCH_3$, $-(CH_2CH_2O)_n(CH_2)_mCH_3$, $-(CH_2CH_2O)_n(CH_2)_mOH$, $-((CH_2)_nO)_m$ $((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, $-(CH_2)_nC(O)NH(CH_2)_mOH$, $C_{1-n}$ alkenyl, $C_{1-n}$ alkynyl, $C_{6-10}$ aryl, pentafluorophenyl, or succinimidyl;

$R^6$ is F, Cl, Br, I, acetate, citrate, bicarbonate, carbonate, chlorate, dihydrogen phosphate, hydrogen phosphate, hydrogen sulfate, hydroxide, nitrate, nitride, nitrite, phosphate, sulfate, sulfide, sulfite, thiocyanate, thiosulfate, oxalate, perchlorate, chlorite, hypochlorite, periodate, iodate, hypoiodate, bromate, hypobromate, hypobromite, hydrogen carbonate, hydrogen sulfate, hydrogen sulfite, hydrogen oxalate, borate, tetraborate, hexfluorosilicate, tartrate, silicate, selenite, arsenate, ethanedioate, oxoethanoate, 2-hydroxyethanoate, propanoate, butanoate, pentanoate, butyrate, formate, lactate, maleate, oleate, oxalate, stearate, tarterate, urate, acrylate, glutamate, malonate, phthalate, barbiturate, cinnamate, hexanoate, folate, propionate, stearate, ascorbate, glutarate, azelate, benzilate, fumarate, gluconate, propiolate, tannate, gallate, titanate, or diuranate;

each n, m, p, q, and r is independently 1 to 10,000; and,
t is 0 to 10,000.

What is claimed is:
1. A biocompatible polymer, comprising:
a polymer backbone comprising one or more repeating units, wherein the one or more repeating units are each individually selected from a zwitterionic precursor repeating unit of Formula (I):

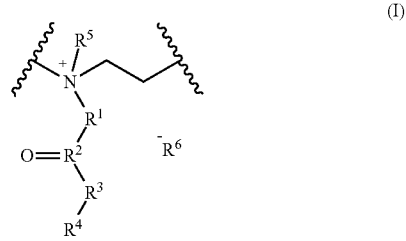

(I)

wherein $R^1$ is $-(CH_2)_n-$, $-(CH_2)_nO(CH_2)_m-$, $-(CH_2CH_2OCH_2CH_2)_n-$, $-(CH_2CH_2O)_n CH_2CH_2-$, $-(CH_2CH_2O)_n(CH_2)_m-$, $-(CH_2)_n(CH_2CH_2O)_m(CH_2)_p-$, $-((CH_2)_{1-8}C(O)O)_n(CH_2)_m-$, $-((CH_2)_{1-8}C(O)O)_n(CH_2CH_2O)_m(OC(O)(CH_2)_{1-8})p-$, $-((CH_2)_{1-8}C(O)O)_n(CH_2CH_2)_m(OC(O)(CH_2)_{1-8})p-$, $-(CH_2C(O)O)_n(CH_2CH_2)_m(OC(O)CH_2)_p-$, $-(CH(CH_3)C(O)On(CH_2CH_2)_m(OC(O)CH(CH_3))_p-$, $-(CH(CH_3)C(O)O)_n(CH_2CH_2)_m(OC(O)CH(CH_3))_p-$, $-((CH_2)_nOC(O)O)(CH_2CH_2)_m-$, $-(CH_2)_nNHC(O)(CH_2)_m-$, $-(CH_2)_nC(O)NH(CH_2)_m-$, $-(CH_2)_nS(O_2)(CH_2)_m-$, $-(CH_2)_nS(O_2)(CH_2)_mO(CH_2)_t-$, $-(CH_2)_nO-$, $-(CH_2)_nO(CH_2)_m O-$, $-(CH_2CH_2OCH_2CH_2)_nO-$, $-(CH_2CH_2O)_n CH_2CH_2O-$, $-(CH_2CH_2O)_n(CH_2)_mO-$, $-(CH_2)_n(CH_2CH_2O)_m(CH_2)_pO-$, $-((CH_2)_{1-8}C(O)O)_n(CH_2)_m O-$, $-((CH_2)_{1-8}C(O)O)_n(CH_2CH_2O)_m(OC(O)(CH_2)_{1-8})_pO-$, $-((CH_2)_{1-8}C(O)O)_n(CH_2CH_2)_m(OC $-(O)CH_2)_pO-$, $-(CH(CH_3)C(O)O)_n(CH_2CH_2)_m(OC(O)CH(CH_3))_pO-$, $-(CH(CH_3)C(O)O)_n(CH_2CH_2)_m(OC(O)CH(CH_3))_pO-$, $-((CH_2)_nOC(O)O)(CH_2CH_2)_mO-$, $-(CH_2)_nNHC(O)(CH_2)_mO-$, $-(CH_2)_nC(O)NH(CH_2)_mO-$, $-(CH_2)_nS(O_2)(CH_2)_mO-$, or $-(CH_2)_nS(O_2)(CH_2)_mO(CH_2)_tO-$;

$R^2$ is C, $P(OR^7)$, or $S(=O)$;

$R^3$ is O, NH, or $OC(=O)$;

$R^4$, $R^5$ and $R^7$ are each independently H, $-CH_3$, $-(CH_2)_n$ $CH_3$, $-(CH_2CH_2O)_nCH_3$, $-(CH_2CH_2O)_n(CH_2)_m$ $CH_3$, $-(CH_2CH_2O)_n(CH_2)_mOH$, $-((CH_2)_nO)_m$, $((CH_2)_pO)_q(CH_2)_rOH$, $-(CH_2CH_2O)_nH$, $-(CH_2)_nOH$, $-(CH_2)_nO(CH_2)_mOH$, $-(CH_2CH_2OCH_2CH_2)_nOH$, $-(CH_2CH_2O)_nCH_2CH_2OH$, $-((CH_2)_{1-8}C(O)O)_n(CH_2)_mOH$, $-((CH_2)_{1-8}C(O)O)_n(CH_2CH_2O)_m(OC(O)(CH_2)_{1-8})_pOH$, $-((CH_2)_{1-8}C(O)O)_n(CH_2CH_2)_m(OC(O)(CH_2)_{1-8})_pOH$, $-(CH_2C(O)O)_n(CH_2CH_2)_m(OC(O)CH_2)_pOH$, $-(CH(CH_3)C(O)O)_n(CH_2CH_2)_m(OC(O)CH(CH_3))_pOH$, $-((CH_2)_nOC(O)O)(CH_2CH_2)_mOH$, $-(CH_2)_nNHC(O)(CH_2)_mOH$, $-(CH_2)_nC(O)NH(CH_2)_m$ OH, $C_{1-n}$ alkenyl, $C_{1-n}$ alkynyl, $C_{6-10}$ aryl, pentafluorophenyl, or succinimidyl;

$R^6$ is F, Cl, Br, I, acetate, citrate, bicarbonate, carbonate, chlorate, dihydrogen phosphate, hydrogen phosphate, hydrogen sulfate, hydroxide, nitrate, nitride, nitrite, phosphate, sulfate, sulfide, sulfite, thiocyanate, thiosulfate, oxalate, perchlorate, chlorite, hypochlorite, periodate, iodate, hypoiodate, bromate, hypobromate, hypobromite, hydrogen carbonate, hydrogen sulfate, hydrogen sulfite, hydrogen oxalate, borate, tetraborate, hexafluorosilicate, tartrate, silicate, selenite, arsenate, ethanedioate, oxoethanoate, 2-hydroxyethanoate, propanoate, butanoate, pentanoate, butyrate, formate, lactate, maleate, oleate, oxalate, stearate, tartrate, urate, acrylate, glutamate, malonate, phthalate, barbiturate, cinnamate, hexanoate, folate, propionate, stearate, ascorbate, glutarate, azelate, benzilate, fumarate, gluconate, propiolate, tannate, gallate, titanate, trifluoroacetate, or diuranate;

each n, m, p, q, and r is independently 1 to 10,000; and, t is 0 to 10,000, wherein the polymer further comprises a functional group capable of conjugating to a peptide, a protein, a monosaccharide, a disaccharide, an oligo/polysaccharide, a lipid, a nucleic acid, a polymer, a target ligand molecule, a prodrug, a small molecule drug, or any combination thereof, wherein the functional group is selected from the group consisting of acyl halide, alcohol, aldehyde, amide, amine, azo, anhydride, azide, hydrazide, toluene derivative, biotin, disulfide, carbonate, carboxylic acid, cyanate, haloalkane, ether, ester, hydroperoxide, hydrazone, isocyanide, imine, isocyanate, ketone, nitrate, nitrile, nitrite, nitro, nitroso, peroxide, benzyl, phosphodiester, vinylsulfone, thiol, hydroxyl, imidoester, pyridyldithiol, phosphonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester, any derivative of the any foregoing, and any combination of any of the foregoing.

2. The biocompatible polymer of claim 1, wherein one or more of the zwitterionic precursor repeating unit is a zwitterionic repeating unit and the zwitterionic repeating unit has a structure of Formula (II):

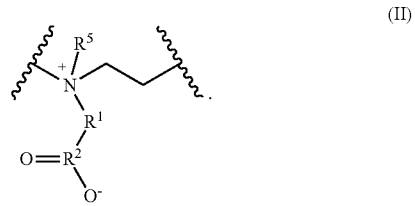

(II)

3. The biocompatible polymer of claim 2, wherein the polymer is a copolymer comprising alternating zwitterionic precursor repeating units having a structure of Formula (I) and zwitterionic repeating units having a structure of Formula (II).

4. The biocompatible polymer of claim 3, wherein the polymer is a block copolymer comprising alternating blocks of one or more zwitterionic precursor repeating units having a structure of Formula (I) and blocks of one or more zwitterionic repeating units having a structure of Formula (II).

5. The biocompatible polymer of claim 1, wherein $R^3$ is O.

6. The biocompatible polymer of claim 1, wherein $R^2$ is C.

7. The biocompatible polymer of claim 1, wherein $R^1$ is $-(CH_2)_n-$, $-(CH_2)_nO(CH_2)_m-$, $-(CH_2CH_2OCH_2CH_2)_n-$, $-(CH_2CH_2O)_nCH_2CH_2-$, $-(CH_2CH_2O)_n(CH_2)_m-$, $-(CH_2)_n(CH_2CH_2O)_m(CH_2)_p-$, $-((CH_2)_{1-8}C(O)O)_n(CH_2)_m-$, $-((CH_2)_{1-8}C(O)O)_n(CH_2CH_2O)_m(OC(O)(CH_2)_{1-8})_p-$, $-((CH_2)_{1-8}C(O)O)_n(CH_2CH_2)_m(OC(O)(CH_2)_{1-8})_p-$, $-(CH_2C(O)O)_n(CH_2CH_2)_m(OC(O)CH_2)_p-$, $-(CH_2C(O)O)_n(CH_2CH_2)_m(OC(O)CH_2)_p-$, $-(CH(CH_3)C(O)O)_n(CH_2CH_2)_m(OC(O)CH(CH_3))_p-$, $-(CH(CH_3)C(O)O)_n(CH_2CH_2)_m(OC(O)CH(CH_3))_p-$, $-((CH_2)_nOC(O)O)(CH_2CH_2)_m-$, $-(CH_2)_nNHC(O)(CH_2)_m-$, $-(CH_2)_nC(O)NH(CH_2)_m-$, $-(CH_2)_nS(O_2)(CH_2)_m-$, or $-(CH_2)_nS(O_2)(CH_2)_mO(CH_2)_t-$.

8. The biocompatible polymer of claim 1, wherein the polymer comprises one or more zwitterionic repeating units having a structure selected from the group consisting of:

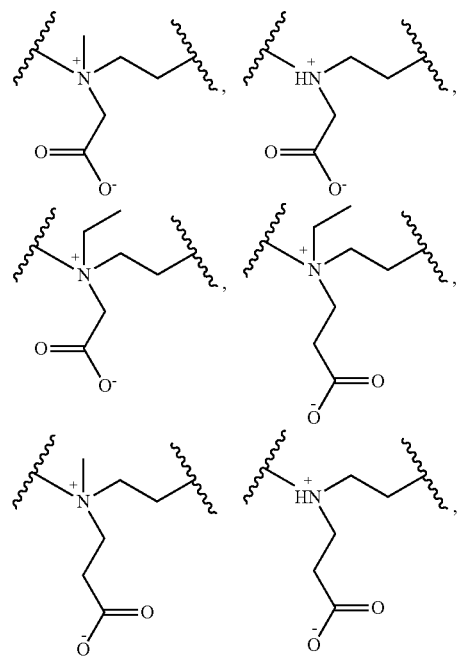

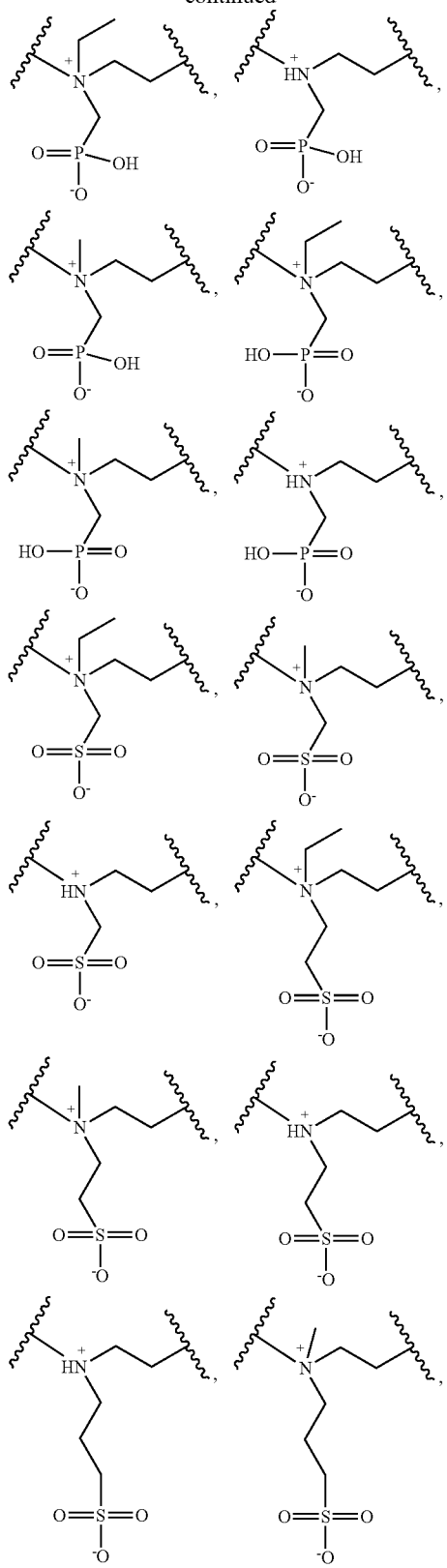

and any combination thereof.

9. The biocompatible polymer according to claim 1, further comprising one or more secondary repeating units, wherein the one or more secondary repeating units have a structure according to Formula (III):

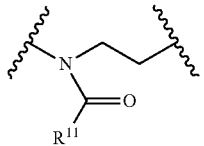

wherein $R^{11}$ is H, —$CH_3$, —$(CH_2)_nCH_3$, —$(CH_2CH_2O)_n$ $CH_3$, —$(CH_2CH_2O)_n(CH_2)_mCH_3$, —$(CH_2CH_2O)_n$ $(CH_2)_mOH$, —$((CH_2)_nO)_m((CH_2)_pO)_q(CH_2)_rOH$, —$(CH_2CH_2O)_nH$, —$(CH_2)_nOH$, —$(CH_2)_nO(CH_2)_m$ OH, —$(CH_2CH_2OCH_2CH_2)_nOH$, —$(CH_2CH_2O)_n$ $CH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_p$ OH, —$((CH_2)_{1-8}C(O)O)_n(CH_2CH_2)_m(OC(O)$ $(CH_2)_{1-8})_pOH$, —$(CH_2C(O)O)_n(CH_2CH_2)_m(OC(O)$ $CH_2)_pOH$, —$(CH(CH_3)C(O)O)_n(CH_2CH_2)_m(OC(O)$ $CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH$ $(CH_2)_mOH$, $C_{1-n}$ alkenyl, $C_{1-n}$ alkynyl, $C_{6-10}$ aryl, pentafluorophenyl, or succinimidyl.

10. The biocompatible polymer of claim 1, wherein the polymer is of Formula (IV):

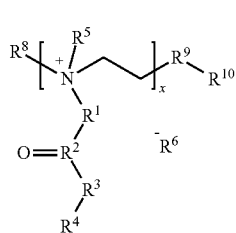

wherein $R^8$ is —$CH_3$, —$CH_2CH=CH_2$, —$(CH_2)_n$ $CH=CH_2$, —$(CH_2)_nCH=CH_2(CH_2)_tCH_3$, —$CH_2C=CH$, —$(CH_2)_nC=CH$, —$(CH_2)_nC=C(CH_2)_t$ $CH_3$, —$(CH_2)_nCH_3$, —$(CH_2)_nCH_2N_3$, —$(CH_2)_nNH_2$, —$(CH_2)_nCH_2SH$, —$(CH_2CH_2O)_nCH_3$, —$(CH_2CH_2O)_n(CH_2)_mCH_3$, —$(CH_2CH_2O)_n(CH_2)_m$ $N_3$, —$(CH_2CH_2O)_n(CH_2)_mSH$, —$(CH_2CH_2O)_n(CH_2)_m$ OH, —$((CH_2)_nO)_m((CH_2)_pO)_q(CH_2)_rOH$, —$(CH_2CH_2O)_nH$, —$(CH_2)_nOH$, —$(CH_2)_nO(CH_2)_m$ OH, —$(CH_2CH_2OCH_2CH_2)_nOH$, —$(CH_2CH_2O)_n$ $CH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_p$ OH, —$((CH_2)_{1-8}C(O)O)_n(CH_2CH_2)_m(OC(O)$ $(CH_2)_{1-8})_pOH$, —$(CH_2C(O)O)_n(CH_2CH_2)_m(OC(O)$ $CH_2)_pOH$, —$(CH(CH_3)C(O)O)_n(CH_2CH_2)_m(OC(O)$ $CH(CH_3))_pOH$, —$((CH_2)_nOC(O)O)(CH_2CH_2)_mOH$, —$(CH_2)_nNHC(O)(CH_2)_mOH$, —$(CH_2)_nC(O)NH$ $(CH_2)_mOH$, $C_{1-n}$ alkenyl, $C_{1-n}$ alkynyl, $C_{6-10}$ aryl, or a compound containing acyl halide, alcohol, aldehyde, amide, amine, azo, anhydride, azide, hydrazide, toluene derivative, biotin, disulfide, carbonate, carboxylic acid, cyanate, haloalkane, ether, ester, hydroperoxide, hydrazone, isocyanide, imine, isocyanate, ketone, nitrate, nitrile, nitrite, nitro, nitroso, peroxide, benzyl, phosphodiester, vinylsulfone, thiol, hydroxyl, imidoester, pyridyldithiol, phosphonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester;

$R^9$ is O, NH, S, Se, $CH_2$, or —N=N—, $R^{10}$ is —H, —N, —$CH_3$, —$CH_2CH$=$CH_2$, —$(CH_2)_n$CH=$CH_2$, —$(CH_2)_n$CH=$CH_2(CH_2)_t$$CH_3$, —$CH_2C$≡CH, —$(CH_2)_n$C≡CH, —$(CH_2)_n$C≡C$(CH_2)_t$$CH_3$, —$(CH_2)_n$$CH_3$, —$(CH_2)_n$$CH_2N_3$, —$(CH_2CH_2O)_n$$CH_3$, —$(CH_2CH_2O)_n(CH_2)_m$$CH_3$, —$(CH_2CH_2O)_n(CH_2)_m$$N_3$, —$(CH_2CH_2O)_n(CH_2)_m$OH, —$((CH_2)_nO)_m$$((CH_2)_pO)_q(CH_2)_r$OH, —$(CH_2CH_2O)_n$H, —$(CH_2)_n$OH, —$(CH_2)_nO(CH_2)_m$OH, —$(CH_2CH_2OCH_2CH_2)_n$OH, —$(CH_2)_nO(CH_2CH_2OH)$, —$((CH_2)_{1-8}C(O)O)_n(CH_2)_m$OH, —$((CH_2)_{1-8}C(O)O)_n(CH_2CH_2O)_m(OC(O)(CH_2)_{1-8})_p$OH, —$((CH_2)_{1-8}C(O)O)_n(CH_2CH_2)_m(OC(O)(CH_2)_{1-8})_p$OH, —$(CH_2C(O)O)_n(CH_2CH_2)_m(OC(O)CH_2)_p$OH, —$(CH(CH_3)C(O)O)_n(CH_2CH_2)_m(OC(O)CH(CH_3))_p$OH, —$((CH_2)_nOC(O)O)(CH_2CH_2)_m$OH, —$(CH_2)_n$NHC(O)$(CH_2)_m$OH, —$(CH_2)_n$C(O)NH$(CH_2)_m$OH, vinyl sulfone, succinimidyl ester, pentafluorophenyl ester, —SH, —$(CH_2)_n$$NH_2$, —$(CH_2)_n$COOH, —$(CH_2)_n$SH, —$(CH_2)_n$NH$(CH_2)_m$$CH_3$, —$(CH_2)_n$NHCH_3, —$(CH_2CH_2O)_n(CH_2)_m$$NH_2$, —$(CH_2CH_2O)_n(CH_2)_m$SH, —$(CH_2CH_2O)_n(CH_2)_m$COOH, $C_{1-n}$ alkenyl, $C_{1-n}$ alkynyl, $C_{6-10}$ aryl, $C_{1-n}$ alkylene-SH,

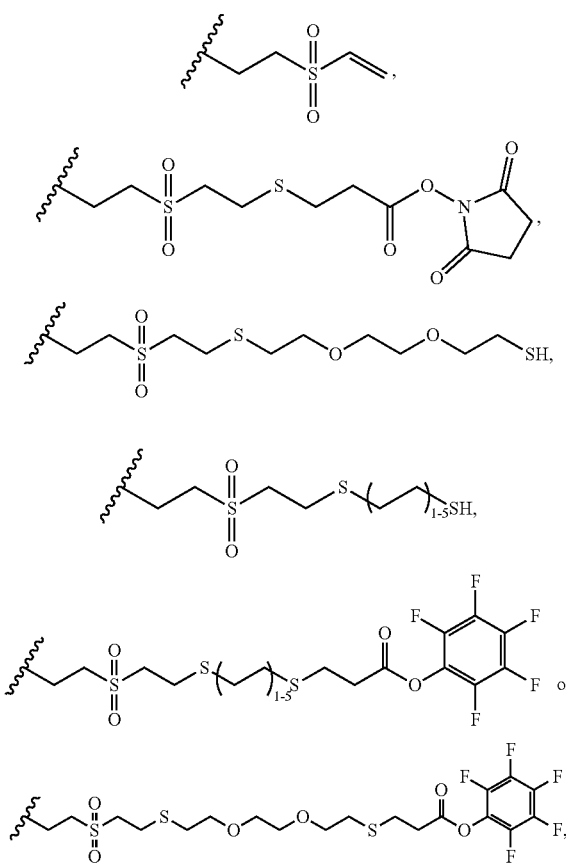

or a compound containing acyl halide, alcohol, aldehyde, amide, amine, azo, anhydride, azide, hydrazide, toluene derivative, biotin, disulfide, carbonate, carboxylic acid, cyanate, haloalkane, ether, ester, hydroperoxide, hydrazone, isocyanide, imine, isocyanate, ketone, nitrate, nitrile, nitrite, nitre, nitroso, peroxide, benzyl, phosphodiester, vinylsulfone, thiol, hydroxyl, imidoester, pyridyldithiol, phosphonic acid, phosphate, pyridinyl, sulfide, sulfone, sulfonic acid, sulfoxide, thiol, azide, alkene, alkyne, nitrone, hydrazide, maleimide, acrylate, methacrylate, acrylamide, methacrylamide, lipoamide, difluorobenzocyclooctyne, tetrazine, pentafluorophenyl ester, or succinimidyl ester; and, x is 1 to 10,000.

11. The biocompatible polymer of claim 10, wherein the polymer is hydrolyzed, and the hydrolyzed polymer has a structure of Formula (V):

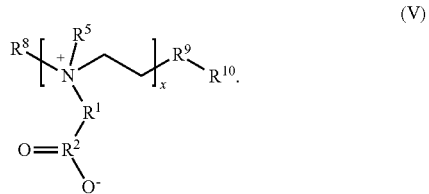

12. The biocompatible polymer of claim 10, wherein $R^8$ is $CH_3$, $R^9$ is O, and $R^{10}$ is H.

13. The biocompatible polymer of claim 10, wherein $R^8$ is $CH_3$, $R^9$ is O, and $R^{10}$ has a structure of:

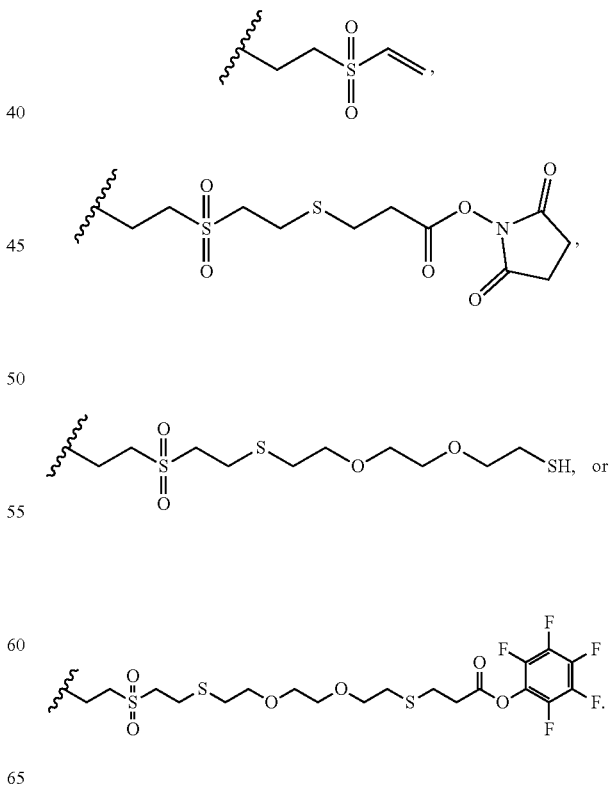

14. The biocompatible polymer of claim 1, wherein the polymer has a structure of:

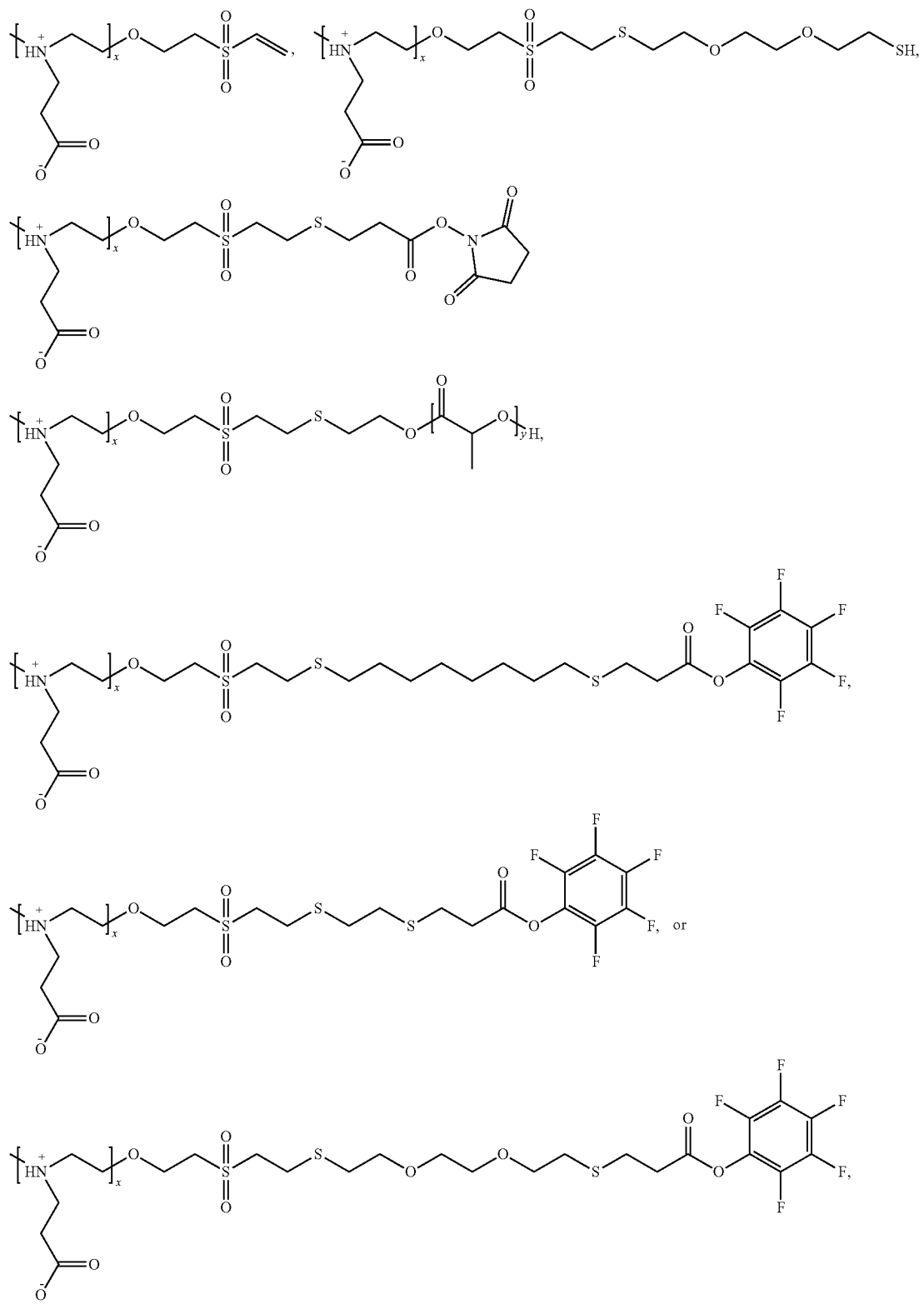

wherein y is 1 to 10,000.

15. The biocompatible polymer of claim 1, wherein the polymer is conjugated to a peptide, a protein, a monosaccharide, a disaccharide, an oligo/polysaccharide, a lipid, a nucleic acid, a polymer, a targeting ligand molecule, a prodrug, a small molecule drug, or any combination thereof.

16. The biocompatible polymer of claim 1, wherein the polymer has a solubility in water at 20-50° C. in a range of about 1 pg/mL to about 500 mg/mL.

17. A nanoparticle comprising:
the biocompatible polymer according to claim 1 and a drug,
wherein the drug is selected from the group consisting of a peptide, a protein, a nucleic acid, a small molecule drug, a prodrug, and any combination thereof.

18. A method comprising:
(i) reacting a polyethyleneimine having a structure of

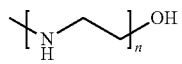

with an α,β-unsaturated ester having a structure of

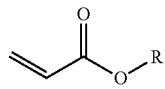

to form an N-alkylated polyethyleneimine having a structure of

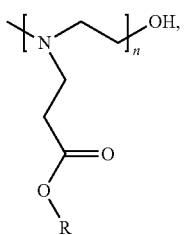

wherein n is from 1 to 10,000 and R is H, —CH$_3$, —(CH$_2$)$_n$CH$_3$, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —(CH$_2$)$_n$OH, —(CH$_2$)$_n$O(CH$_2$)$_m$OH, —(CH$_2$CH$_2$OCH$_2$CH$_2$)$_n$OH, —(CH$_2$CH$_2$O)$_n$CH$_2$CH$_2$OH, —((CH$_2$)$_{1-8}$C(O)O)$_n$(CH$_2$)$_m$OH, —((CH$_2$)$_{1-8}$C(O)O)$_n$(CH$_2$CH$_2$O)$_m$(OC(O)(CH$_2$)$_{1-8}$)$_p$OH, —((CH$_2$)$_{1-8}$C(O)O)n(CH$_2$CH$_2$)$_m$(OC(O)(CH$_2$)$_{1-8}$)$_p$OH, —(CH$_2$C(O)O)$_n$(CH$_2$CH$_2$)$_m$(OC(O)CH$_2$)$_p$OH, —(CH(CH$_3$)C(O)O)$_n$(CH$_2$CH$_2$)$_m$(OC(O)CH(CH$_3$))$_p$OH, —((CH$_2$)$_n$OC(O)O)(CH$_2$CH$_2$)$_m$OH, —(CH$_2$)$_n$NHC(O)(CH$_2$)$_m$OH, —(CH$_2$)$_n$C(O)NH(CH$_2$)$_m$OH, C$_{1-n}$ alkenyl, C$_{1-n}$ alkynyl, C$_{6-10}$ aryl, pentafluorophenyl ester or succinimidyl;
(ii) hydrolyzing the N-alkylated polyethyleneimine to provide a zwitterionic N-alkylated polyethyleneimine; and
(iii) reacting the zwitterionic N-alkylated polyethyleneimine with a compound having a functional group capable of conjugating to a peptide, a protein, a monosaccharide, a disaccharide, an oligo/polysaccharide, a lipid, a nucleic acid, a polymer, a targeting ligand molecule, a prodrug, a small molecule drug, or any combination thereof to form a biocompatible zwitterionic polymer.

19. A system for nucleic acid delivery comprising:
a cationic core comprising a cationic compound and nucleic acid; and,
a polysaccharide-anionic peptide conjugate comprising an anionic peptide physically bound to a polysaccharide, wherein the polysaccharide-anionic peptide conjugate is adsorbed to the cationic core,
and the biocompatible polymer of claim 1 is associated with the cationic core or the polysaccharide-anionic peptide conjugate.

20. A biocompatible polymer, comprising a polymer backbone comprising
one or more repeating units selected from a zwitterionic precursor repeating unit of Formula (I):

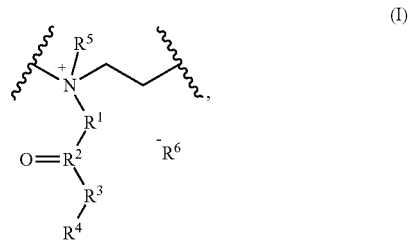

and
one or more repeating units selected from a zwitterionic repeating unit of Formula (II):

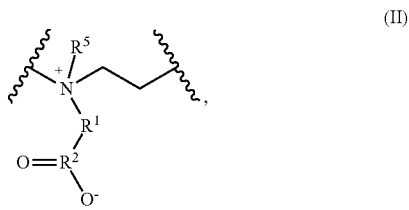

wherein each R$^1$ is independently —(CH$_2$)$_n$—, —(CH$_2$)$_n$O(CH$_2$)$_m$—, —(CH$_2$CH$_2$OCH$_2$CH$_2$)$_n$—, —(CH$_2$CH$_2$O)$_n$CH$_2$CH$_2$—, —(CH$_2$CH$_2$O)$_n$(CH$_2$)$_m$—, —(CH$_2$)$_n$(CH$_2$CH$_2$O)$_m$(CH$_2$)$_p$—, —((CH$_2$)$_{1-8}$C(O)O)$_n$(CH$_2$)$_m$—, —((CH$_2$)$_{1-8}$C(O)O)$_n$(CH$_2$CH$_2$O)$_m$(OC(O)(CH$_2$)$_{1-8}$)$_p$-, —((CH$_2$)$_{1-8}$C(O)O)$_n$(CH$_2$CH$_2$)$_m$(OC(O)(CH$_2$)$_{1-8}$)$_p$-, —(CH$_2$C(O)O)$_n$(CH$_2$)$_m$(OC(O)CH$_2$)$_p$—, —(CH(CH$_3$)C(O)O)n(CH$_2$CH$_2$)$_m$(OC(O)CH(CH$_3$))$_p$—, —(CH(CH$_3$)C(O)O)$_n$(CH$_2$CH$_2$)$_m$(OC(O)CH(CH$_3$))$_p$—, —(CH$_2$)$_n$OC(O)(CH$_2$CH$_2$)$_m$, —(CH$_2$)$_n$NHC(O)(CH$_2$)$_m$—, —(CH$_2$)$_n$C(O)NH(CH$_2$)$_m$—, —(CH$_2$)$_n$S(O$_2$)(CH$_2$)$_m$—, —(CH$_2$)$_n$S(O$_2$)(CH$_2$)$_m$O(CH$_2$)$_t$—, —(CH$_2$)$_n$O—, —(CH$_2$)$_n$O(CH$_2$)$_m$O—, —(CH$_2$CH$_2$OCH$_2$CH$_2$)$_n$O—, —(CH$_2$CH$_2$O)$_n$CH$_2$CH$_2$O—, —(CH$_2$CH$_2$O)$_n$(CH$_2$)$_m$O—, —(CH$_2$)$_n$(CH$_2$CH$_2$O)$_m$(CH$_2$)$_p$O—, —((CH$_2$)$_{1-8}$C(O)O)$_n$(CH$_2$)$_m$O—, —((CH$_2$)$_{1-8}$C(O)O)$_n$(CH$_2$CH$_2$O)$_m$(OC(O)(CH$_2$)$_{1-8}$)$_p$O—, —((CH$_2$)$_{1-8}$C(O)O)$_n$(CH$_2$CH$_2$)$_m$(OC(O)(CH$_2$)$_{1-8}$)$_p$O—, —(CH$_2$C(O)O)$_n$(CH$_2$CH$_2$)$_m$(OC(O)CH$_2$)$_p$O—, —(CH(CH$_3$)C(O)O)$_n$(CH$_2$CH$_2$)$_m$(OC(O)CH(CH$_3$))$_p$O—, —(CH(CH$_3$)C(O)O)$_n$(CH$_2$CH$_2$)$_m$(OC(O)CH(CH$_3$))$_p$O—, —((CH$_2$)$_n$OC(O)O)(CH$_2$CH$_2$)$_m$O—, —(CH$_2$)$_n$NHC(O)(CH$_2$)$_m$O—, —(CH$_2$)$_n$C(O)NH(CH$_2$)$_m$O—, —(CH$_2$)$_n$S(O$_2$)(CH$_2$)$_m$O—, or —(CH$_2$)$_n$S(O$_2$)(CH$_2$)$_m$O(CH$_2$)$_t$O—;
each R$^2$ is independently C, P(OR$^7$), or S(═O);
each R$^3$ is independently O, NH, or OC(═O);
each R$^4$, R$^5$ and R$^7$ is independently H, —CH$_3$, —(CH$_2$)$_n$CH$_3$, —(CH$_2$CH$_2$O)$_n$CH$_3$, —(CH$_2$CH$_2$O)$_n$(CH$_2$)$_m$CH$_3$, —(CH$_2$CH$_2$O)$_n$(CH$_2$)$_m$OH, —((CH$_2$)$_n$O)$_m$((CH$_2$)$_p$O)$_q$(CH$_2$)$_r$OH, —(CH$_2$CH$_2$O)$_n$H, —$(CH_2)_nOH$, —$(CH_2)_nO(CH_2)_mOH$, —$(CH_2CH_2OCH_2CH_2)_nOH$, —$(CH_2CH_2O)_nCH_2CH_2OH$, —$((CH_2)_{1-8}C(O)O)_n(CH_2)_mOH$, —$((CH_2)_{1-8}C(O)O)_n(CH_2CH_2O)_m(OC(O)(CH_2)_{1-8})_p$ OH, —$((CH_2)_{1-8}C(O)O)_n(CH_2CH_2)_m(OC(O)(CH_2)_{1-8})_pOH$, —$(CH_2C(O)O)_n(CH_2CH_2)_m(OC(O)CH_2)_pOH$, —$(CH(CH_3)C(O)O)_n(CH_2CH_2)_m(OC(O)CH(CH_3))pOH$, —$((CH_2)_nOC(O)O)(CH_2CH_2)_mOH$, —$(CH_2)_nNHC(O)(CH_2)_mOH$, —$(CH_2)_nC(O)NH(CH_2)_mOH$, $C_{1-n}$ alkenyl, $C_{1-n}$ alkynyl, $C_{6-10}$ aryl, pentafluorophenyl, or succinimidyl;

$R^6$ is F, Cl, Br, I, acetate, citrate, bicarbonate, carbonate, chlorate, dihydrogen phosphate, hydrogen phosphate, hydrogen sulfate, hydroxide, nitrate, nitride, nitrite, phosphate, sulfate, sulfide, sulfite, thiocyanate, thiosulfate, oxalate, perchlorate, chlorite, hypochlorite, periodate, iodate, hypoiodate, bromate, hypobromate, hypobromite, hydrogen carbonate, hydrogen sulfate, hydrogen sulfite, hydrogen oxalate, borate, tetraborate, hexfluorosilicate, tartrate, silicate, selenite, arsenate, ethanedioate, oxoethanoate, 2-hydroxyethanoate, propanoate, butanoate, pentanoate, butyrate, formate, lactate, maleate, oleate, oxalate, stearate, tartrate, urate, acrylate, glutamate, malonate, phthalate, barbiturate, cinnamate, hexanoate, folate, propionate, stearate, ascorbate, glutarate, azelate, benzilate, fumarate, gluconate, propiolate, tannate, gallate, titanate, trifluoroacetate, or diuranate;

each n, m, p, q, and r is independently 1 to 10,000; and, t is 0 to 10,000.

* * * * *